U S011299526B2

(12) United States Patent
Lim et al.

(10) Patent No.: US 11,299,526 B2
(45) Date of Patent: Apr. 12, 2022

(54) P53-BAD FUSION PROTEINS

(71) Applicant: University of Utah Research Foundation, Salt Lake City, UT (US)

(72) Inventors: Carol S. Lim, Salt Lake City, UT (US); Phong Lu, Salt Lake City, UT (US)

(73) Assignee: UNIVERSITY OF UTAH RESEARCH FOUNDATION, Salt Lake City, UT (US)

( * ) Notice: Subject to any disclaimer, the term of this patent is extended or adjusted under 35 U.S.C. 154(b) by 0 days.

(21) Appl. No.: 16/414,683

(22) Filed: May 16, 2019

(65) Prior Publication Data
US 2019/0367573 A1   Dec. 5, 2019

Related U.S. Application Data

(60) Provisional application No. 62/672,372, filed on May 16, 2018.

(51) Int. Cl.
C07K 14/47 (2006.01)
A61K 38/00 (2006.01)
A61P 35/00 (2006.01)

(52) U.S. Cl.
CPC .......... *C07K 14/4747* (2013.01); *A61P 35/00* (2018.01); *C07K 14/4746* (2013.01); *A61K 38/00* (2013.01); *C07K 2319/00* (2013.01)

(58) Field of Classification Search
None
See application file for complete search history.

(56) References Cited

PUBLICATIONS

Polzien et al.—Identification of novel in vivo phosphorylation sites of the human proapoptotic protein BAD. J. Biol. Chem. 284, 28004-28020, 2009. (Year: 2009).*
G-D Chen et al. Requirement of nuclear localization and transcriptional activity of p53 for its targeting to the yolk syncytial layer (YSL) nuclei in zebrafish embryo and its use for apoptosis assay. Biochem. Biophys. Res. Comm. 344, 272-282, 2006. (Year: 2006).*
Lu et al. Mitochondrially targeted p53 domains as a stand alone or adjunct to paclitaxel for the treatment of ovarian cancer. [abstract]. In: Proc. of the 107th Annual Meeting of the AACR; Apr. 16-20, 2016; New Orleans, LA. Philadelphia (PA): AACR; Cancer Res 2016;76(14 Suppl): Abstract nr 3500. (Year: 2016).*
X Chen et al. Fusion protein linkers: Property, design and functionality. Adv. Drug Del. Rev. 65, 1357-1369, 2013. (Year: 2013).*
Chène P., The role of the tetramerization domain in p53 function. Oncogene, 20, 2611-2617, 2001. (Year: 2001).*
Zilfou et al., The corepressor mSin3a interacts with the proline rich domain of p53 and protects p53 from proteasome-mediated degradation. Mol. Cel. Biol. 3974-3985, 2001. (Year: 2001).*
Shimizu et al. ,The conformationally flexible S9-S10 linker region in the core domain of p53 contains a novel MDM2 binding site whose mutation increases ubiquitination of p53 in vivo. J. Biol. Chem., 277, 28446-28458, 2002. (Year: 2002).*
Search of Conserved domains for SEQ ID No. 3, NCBI Website. Accessed Jul. 1, 2020. https://www.ncbi.nlm.nih.gov/Structure/cdd/wrpsb.cgi (Year: 2020).*
Erster, S., et al., In vivo mitochondrial p53 translocation triggers a rapid first wave of cell death in response to DNA damage that can precede p53 target gene activation. Mol Cell Biol, 2004. 24(15): p. 6728-41.
Mossalam, M., et al., Direct induction of apoptosis using an optimal mitochondrially targeted p53. Mol Pharm, 2012. 9(5): p. 1449-58.
Vaseva, A.V. and U.M. Moll, The mitochondrial p53 pathway. Biochim Biophys Acta, 2009. 1787(5): p. 414-20.
Matissek, K.J., et al., Delivery of a monomeric p53 subdomain with mitochondrial targeting signals from pro-apoptotic Bak or Bax. Pharm Res, 2014. 31(9): p. 2503-15.
Danial, N.N., BAD: undertaker by night, candyman by day. Oncogene, 2008. 27 Suppl 1: p. S53-70.
Cong, Y.S., J. Wen, and S. Bacchetti, The human telomerase catalytic subunit hTERT: organization of the gene and characterization of the promoter. Hum Mol Genet, 1999. 8(1): p. 137-42.
Davis, J.J., et al., Oncolysis and suppression of tumor growth by a GFP-expressing oncolytic adenovirus controlled by an hTERT and CMV hybrid promoter. Cancer Gene Ther, 2006. 13(7): p. 720-3.
Kyo, S., et al., Understanding and exploiting hTERT promoter regulation for diagnosis and treatment of human cancers. Cancer Sci, 2008. 99(8): p. 1528-38.
Li, Y.H., et al., Enhancing HSP70-ShRNA transfection in 22RV1 prostate cancer cells by combination of sonoporation, liposomes and HTERT/CMV chimeric promoter. Int J Oncol, 2013. 43(1): p. 151-8.
Takakura, M., et al., Cloning of human telomerase catalytic subunit (hTERT) gene promoter and identification of proximal core promoter sequences essential for transcriptional activation in immortalized and cancer cells. Cancer Res, 1999. 59(3): p. 551-7.
Xie, X., et al., A novel hTERT promoter-driven E1A therapeutic for ovarian cancer. Mol Cancer Ther, 2009. 8(8): p. 2375-82.
Chen, X., et al., Cancer-specific promoters for expression-targeted gene therapy: ran, brms1 and mcm5. J Gene Med, 2016. 18(7): p. 89-101.
Kim, J., et al., Enhancing the therapeutic efficacy of adenovirus in combination with biomaterials. Biomaterials, 2012. 33(6): p. 1838-50.

(Continued)

*Primary Examiner* — Elly-Gerald Stoica
(74) *Attorney, Agent, or Firm* — Ballard Spahr LLP

(57) ABSTRACT

Disclosed are peptides comprising a p53 peptide and a BH3-only protein. In some aspects, wherein the BH3-only protein is BAD, BID, BIM, NOXA. Disclosed are nucleic acid sequences comprising a sequence capable of encoding a p53 peptide operably linked to a nucleic acid sequence capable of encoding a BH3-only protein. Disclosed are nucleic acid sequences comprising a sequence capable of encoding one or more of the peptides disclosed herein. Disclosed are vectors comprising a nucleic acid sequence, wherein the nucleic acid sequence is capable of encoding one or more of the peptides disclosed herein. Also disclosed are methods of using the disclosed peptides, nucleic acid sequences, and vectors.

15 Claims, 14 Drawing Sheets
Specification includes a Sequence Listing.

(56) References Cited

PUBLICATIONS

Kim, J., et al., Efficient lung orthotopic tumor-growth suppression of oncolytic adenovirus complexed with RGD-targeted bioreducible polymer. Gene Ther, 2014. 21(5): p. 476-83.

Kim, J., et al., Active targeting of RGD-conjugated bioreducible polymer for delivery of oncolytic adenovirus expressing shRNA against IL-8 mRNA. Biomaterials, 2011. 32(22): p. 5158-66.

Marchenko, N.D., A. Zaika, and U.M. Moll, Death signal-induced localization of p53 protein to mitochondria. A potential role in apoptotic signaling. J Biol Chem, 2000. 275(21): p. 16202-12.

Mihara, M., et al., p53 has a direct apoptogenic role at the mitochondria. Mol Cell, 2003. 11(3): p. 577-90.

Palacios, G., et al., Mitochondrially targeted wild-type p53 induces apoptosis in a solid human tumor xenograft model. Cell Cycle, 2008. 7(16): p. 2584-90.

Talos, F., et al., Mitochondrially targeted p53 has tumor suppressor activities in vivo. Cancer Res, 2005. 65(21): p. 9971-81.

Palacios, G. and U.M. Moll, Mitochondrially targeted wild-type p53 suppresses growth of mutant p53 lymphomas in vivo. Oncogene, 2006. 25(45): p. 6133-9.

Zang, G., et al., Adenoviral mediated transduction of adenoid cyctic carcinoma by human TRAIL gene driven with hTERT tumor specific promoter induces apoptosis. Cancer Biol Ther, 2009. 8(10): p. 966-72.

Fang, X., et al., Regulation of BAD phosphorylation at serine 112 by the Ras-mitogen-activated protein kinase pathway. Oncogene, 1999. 18(48): p. 6635-40.

Virdee, K., P.A. Parone, and A.M. Tolkovsky, Phosphorylation of the pro-apoptotic protein BAD on serine 155, a novel site, contributes to cell survival. Current biology: CB, 2000. 10(18): p. 1151-4.

Fewell, J.G., et al., Treatment of disseminated ovarian cancer using nonviral interleukin-12 gene therapy delivered intraperitoneally. J Gene Med, 2009. 11(8): p. 718-28.

Kim, J., et al., Intraperitoneal gene therapy with adenoviral-mediated p53 tumor suppressor gene for ovarian cancer model in nude mouse. Cancer Gene Ther, 1999. 6(2): p. 172-8.

Perfettini, J.L., R.T. Kroemer, and G. Kroemer, Fatal liaisons of p53 with Bax and Bak. Nat Cell Biol, 2004. 6(5): p. 386-8.

Matissek, K.J., et al., The DNA binding domain of p53 is sufficient to trigger a potent apoptotic response at the mitochondria. Mol Pharm, 2013. 10(10): p. 3592-602.

Kim, J., et al., Therapeutic efficacy of a systemically delivered oncolytic adenovirus—biodegradable polymer complex. Biomaterials, 2013. 34(19): p. 4622-31.

Kim, P.H., et al., Bioreducible polymer-conjugated oncolytic adenovirus for hepatoma-specific therapy via systemic administration. Biomaterials, 2011. 32(35): p. 9328-42.

Kim, P.H., et al., The effect of surface modification of adenovirus with an arginine-grafted bioreducible polymer on transduction efficiency and immunogenicity in cancer gene therapy. Biomaterials, 2010. 31(7): p. 1865-74.

Lu, P., et al., Delivery of drugs and macromolecules to the mitochondria for cancer therapy. J Control Release, 2016. 240: p. 38-51.

Gu, J., et al., hTERT promoter induces tumor-specific Bax gene expression and cell killing in syngenic mouse tumor model and prevents systemic toxicity. Gene Ther, 2002. 9(1): p. 30-7.

Kim, T.I. and S.W. Kim, Bioreducible polymers for gene delivery. React Funct Polym, 2011. 71(3): p. 344-349.

Danhier, F., A. Le Breton, and V. Preat, RGD-based strategies to target alpha(v) beta(3) integrin in cancer therapy and diagnosis. Mol Pharm, 2012. 9(11): p. 2961-73.

* cited by examiner

SEQUENCE LISTING

<160> NUMBER OF SEQ ID NOS: 12

<210> SEQ ID NO 1
<211> LENGTH: 168
<212> TYPE: PRT
<213> ORGANISM: Homo sapiens

<400> SEQUENCE: 1

```
Met Phe Gln Ile Pro Glu Phe Glu Pro Ser Glu Gln Glu Asp Ser Ser
1               5                   10                  15

Ser Ala Glu Arg Gly Leu Gly Pro Ser Pro Ala Gly Asp Gly Pro Ser
            20                  25                  30

Gly Ser Gly Lys His His Arg Gln Ala Pro Gly Leu Leu Trp Asp Ala
        35                  40                  45

Ser His Gln Gln Glu Gln Pro Thr Ser Ser Ser His His Gly Gly Ala
    50                  55                  60

Gly Ala Val Glu Ile Arg Ser Arg His Ser Ser Tyr Pro Ala Gly Thr
65                  70                  75                  80
```

Glu Asp Asp Glu Gly Met Gly Glu Glu Pro Ser Pro Phe Arg Gly Arg
                85                  90                  95

Ser Arg Ser Ala Pro Pro Asn Leu Trp Ala Ala Gln Arg Tyr Gly Arg
            100                 105                 110

Glu Leu Arg Arg Met Ser Asp Glu Phe Val Asp Ser Phe Lys Lys Gly
        115                 120                 125

Leu Pro Arg Pro Lys Ser Ala Gly Thr Ala Thr Gln Met Arg Gln Ser
    130                 135                 140

Ser Ser Trp Thr Arg Val Phe Gln Ser Trp Trp Asp Arg Asn Leu Gly
145                 150                 155                 160

Arg Gly Ser Ser Ala Pro Ser Gln
                165

<210> SEQ ID NO 2
<211> LENGTH: 168
<212> TYPE: PRT
<213> ORGANISM: Artificial Sequence
<220> FEATURE:
<223> OTHER INFORMATION: synthetic construct; mutated BAD peptide

<400> SEQUENCE: 2

Met Phe Gln Ile Pro Glu Phe Glu Pro Ser Glu Gln Glu Asp Ser Ser
1               5                   10                  15

Ser Ala Glu Arg Gly Leu Gly Pro Ser Pro Ala Gly Asp Gly Pro Ser
            20                  25                  30

Gly Ser Gly Lys His His Arg Gln Ala Pro Gly Leu Leu Trp Asp Ala
        35                  40                  45

Ser His Gln Gln Glu Gln Pro Thr Ser Ser Ser His His Gly Gly Ala
    50                  55                  60

Gly Ala Val Glu Ile Arg Ser Arg His Ser Ala Tyr Pro Ala Gly Thr
65                  70                  75                  80

Glu Asp Asp Glu Gly Met Gly Glu Glu Pro Ser Pro Phe Arg Gly Arg
                85                  90                  95

Ser Arg Ala Ala Pro Pro Asn Leu Trp Ala Ala Gln Arg Tyr Gly Arg
            100                 105                 110

Glu Leu Arg Arg Met Ser Asp Glu Phe Val Asp Ser Phe Lys Lys Gly
        115                 120                 125

Leu Pro Arg Pro Lys Ser Ala Gly Thr Ala Thr Gln Met Arg Gln Ser
    130                 135                 140

Ser Ser Trp Thr Arg Val Phe Gln Ser Trp Trp Asp Arg Asn Leu Gly
145                 150                 155                 160

Arg Gly Ser Ser Ala Pro Ser Gln
                165

<210> SEQ ID NO 3
<211> LENGTH: 393
<212> TYPE: PRT
<213> ORGANISM: Homo sapiens

<400> SEQUENCE: 3

Met Glu Glu Pro Gln Ser Asp Pro Ser Val Glu Pro Pro Leu Ser Gln
1               5                   10                  15

Glu Thr Phe Ser Asp Leu Trp Lys Leu Leu Pro Glu Asn Asn Val Leu
            20                  25                  30

Ser Pro Leu Pro Ser Gln Ala Met Asp Asp Leu Met Leu Ser Pro Asp
        35                  40                  45

```
Asp Ile Glu Gln Trp Phe Thr Glu Asp Pro Gly Pro Asp Glu Ala Pro
 50                  55                  60
Arg Met Pro Glu Ala Ala Pro Pro Val Ala Pro Ala Pro Ala Ala Pro
 65                  70                  75                  80
Thr Pro Ala Ala Pro Ala Pro Ala Pro Ser Trp Pro Leu Ser Ser Ser
             85                  90                  95
Val Pro Ser Gln Lys Thr Tyr Gln Gly Ser Tyr Gly Phe Arg Leu Gly
            100                 105                 110
Phe Leu His Ser Gly Thr Ala Lys Ser Val Thr Cys Thr Tyr Ser Pro
            115                 120                 125
Ala Leu Asn Lys Met Phe Cys Gln Leu Ala Lys Thr Cys Pro Val Gln
130                 135                 140
Leu Trp Val Asp Ser Thr Pro Pro Pro Gly Thr Arg Val Arg Ala Met
145                 150                 155                 160
Ala Ile Tyr Lys Gln Ser Gln His Met Thr Glu Val Val Arg Arg Cys
                165                 170                 175
Pro His His Glu Arg Cys Ser Asp Ser Asp Gly Leu Ala Pro Pro Gln
            180                 185                 190
His Leu Ile Arg Val Glu Gly Asn Leu Arg Val Glu Tyr Leu Asp Asp
            195                 200                 205
Arg Asn Thr Phe Arg His Ser Val Val Val Pro Tyr Glu Pro Pro Glu
210                 215                 220
Val Gly Ser Asp Cys Thr Thr Ile His Tyr Asn Tyr Met Cys Asn Ser
225                 230                 235                 240
Ser Cys Met Gly Gly Met Asn Arg Arg Pro Ile Leu Thr Ile Ile Thr
                245                 250                 255
Leu Glu Asp Ser Ser Gly Asn Leu Leu Gly Arg Asn Ser Phe Glu Val
            260                 265                 270
Arg Val Cys Ala Cys Pro Gly Arg Asp Arg Arg Thr Glu Glu Glu Asn
            275                 280                 285
Leu Arg Lys Lys Gly Glu Pro His His Glu Leu Pro Pro Gly Ser Thr
290                 295                 300
Lys Arg Ala Leu Pro Asn Asn Thr Ser Ser Ser Pro Gln Pro Lys Lys
305                 310                 315                 320
Lys Pro Leu Asp Gly Glu Tyr Phe Thr Leu Gln Ile Arg Gly Arg Glu
                325                 330                 335
Arg Phe Glu Met Phe Arg Glu Leu Asn Glu Ala Leu Glu Leu Lys Asp
            340                 345                 350
Ala Gln Ala Gly Lys Glu Pro Gly Gly Ser Arg Ala His Ser Ser His
            355                 360                 365
Leu Lys Ser Lys Lys Gly Gln Ser Thr Ser Arg His Lys Lys Leu Met
370                 375                 380
Phe Lys Thr Glu Gly Pro Asp Ser Asp
385                 390

<210> SEQ ID NO 4
<211> LENGTH: 191
<212> TYPE: PRT
<213> ORGANISM: Homo sapiens

<400> SEQUENCE: 4

Thr Tyr Gln Gly Ser Tyr Gly Phe Arg Leu Gly Phe Leu His Ser Gly
 1               5                  10                  15
Thr Ala Lys Ser Val Thr Cys Thr Tyr Ser Pro Ala Leu Asn Lys Met
                20                  25                  30
```

```
Phe Cys Gln Leu Ala Lys Thr Cys Pro Val Gln Leu Trp Val Asp Ser
         35                  40                  45

Thr Pro Pro Gly Thr Arg Val Arg Ala Met Ala Ile Tyr Lys Gln
 50                  55                  60

Ser Gln His Met Thr Glu Val Val Arg Arg Cys Pro His His Glu Arg
 65                  70                  75                  80

Cys Ser Asp Ser Asp Gly Leu Ala Pro Pro Gln His Leu Ile Arg Val
                 85                  90                  95

Glu Gly Asn Leu Arg Val Glu Tyr Leu Asp Asp Arg Asn Thr Phe Arg
                 100                 105                 110

His Ser Val Val Val Pro Tyr Glu Pro Pro Glu Val Gly Ser Asp Cys
                 115                 120                 125

Thr Thr Ile His Tyr Asn Tyr Met Cys Asn Ser Ser Cys Met Gly Gly
                 130                 135                 140

Met Asn Arg Arg Pro Ile Leu Thr Ile Ile Thr Leu Glu Asp Ser Ser
145                 150                 155                 160

Gly Asn Leu Leu Gly Arg Asn Ser Phe Glu Val Arg Val Cys Ala Cys
                 165                 170                 175

Pro Gly Arg Asp Arg Arg Thr Glu Glu Glu Asn Leu Arg Lys Lys
                 180                 185                 190

<210> SEQ ID NO 5
<211> LENGTH: 507
<212> TYPE: DNA
<213> ORGANISM: Homo sapiens

<400> SEQUENCE: 5
atgttccaga tcccagagtt tgagccgagt gagcaggaag actccagctc tgcagagagg    60
ggcctgggcc ccagccccgc aggggacggg ccctcaggct ccggcaagca tcatcgccag   120
gccccaggcc tcctgtggga cgccagtcac cagcaggagc agccaaccag cagcagccat   180
catggaggcg ctggggctgt ggagatccgg agtcgccaca gctcctaccc cgcggggacg   240
gaggacgacg aagggatggg ggaggagccc agccccttc ggggccgctc gcgctcggcg   300
ccccccaacc tctgggcagc acagcgctat ggccgcgagc tccggaggat gagtgacgag   360
tttgtggact cctttaagaa gggacttcct cgcccgaaga gcgcgggcac agcaacgcag   420
atgcggcaaa gctccagctg gacgcgagtc ttccagtcct ggtgggatcg aacttgggc    480 agggggaagct ccgccccctc ccagtga                                      507

<210> SEQ ID NO 6
<211> LENGTH: 1695
<212> TYPE: DNA
<213> ORGANISM: Artificial Sequence
<220> FEATURE:
<223> OTHER INFORMATION: synthetic construct; p53 operably linked to BAD

<400> SEQUENCE: 6
atggaggagc cgcagtcaga tcctagcgtc gagccccctc tgagtcagga aacattttca    60
gacctatgga aactacttcc tgaaaacaac gttctgtccc ccttgccgtc ccaagcaatg   120
gatgatttga tgctgtcccc ggacgatatt gaacaatggt tcactgaaga cccaggtcca   180
gatgaagctc ccagaatgcc agaggctgct ccccccgtgg ccctgcacc agcagctcct   240 acaccggcgg cccctgcacc agccccctcc tggcccctgt catcttctgt cccttcccag   300
aaaacctacc agggcagcta cggtttccgt ctgggcttct gcattctggg acagccaag   360
```

```
tctgtgactt gcacgtactc ccctgccctc aacaagatgt tttgccaact ggccaagacc    420
tgccctgtgc agctgtgggt tgattccaca ccccgcccg gcacccgcgt ccgcgccatg     480
gccatctaca agcagtcaca gcacatgacg gaggttgtga ggcgctgccc ccaccatgag    540
cgctgctcag atagcgatgg tctggcccct cctcagcatc ttatccgagt ggaaggaaat    600
ttgcgtgtgg agtatttgga tgacagaaac acttttcgac atagtgtggt ggtgccctat    660
gagccgcctg aggttggctc tgactgtacc accatccact acaactacat gtgtaacagt    720
tcctgcatgg gcggcatgaa ccggaggccc atcctcacca tcatcacact ggaagactcc    780
agtggtaatc tactgggacg gaacagcttt gaggtgcgtg tttgtgcctg tcctgggaga    840
gaccggcgca cagaggaaga gaatctccgc aagaaagggg agcctcacca cgagctgccc    900
ccagggagca ctaagcgagc actgcccaac aacaccagct cctctcccca gccaaagaag    960
aaaccactgg atggagaata tttcaccctt cagatccgtg ggcgtgagcg cttcgagatg    1020 ttccagagc tgaatgaggc cttggaactc aaggatgccc aggctgggaa ggagccaggg     1080
gggagcaggg ctcactccag ccacctgaag tccaaaaagg gtcagtctac ctcccgccat    1140
aaaaaactca tgttcaagac agaagggcct gactcagact taggtaccat gttccagatc    1200
ccagagtttg agccgagtga gcaggaagac tccagctctg cagagagggg cctgggcccc    1260
agccccgcag gggacgggcc ctcaggctcc ggcaagcatc atcgccaggc cccaggcctc    1320
ctgtgggacg ccagtcacca gcaggagcag ccaaccagca gcagccatca tggaggcgct    1380
ggggctgtgg agatccggag tcgccacagc tcctaccccg cggggacgga ggacgacgaa    1440
gggatggggg aggagcccag ccccttcgg ggccgctcgc gctcggcgcc ccccaacctc     1500
tgggcagcac agcgctatgg ccgcgagctc cggaggatga gtgacgagtt tgtggactcc    1560
tttaagaagg gacttcctcg cccgaagagc gcgggcacag caacgcagat gcggcaaagc    1620
tccagctgga cgcgagtctt ccagtcctgg tgggatcgga acttgggcag gggaagctcc    1680
gccccctccc agtga                                                    1695
```

<210> SEQ ID NO 7
<211> LENGTH: 507
<212> TYPE: DNA
<213> ORGANISM: Artificial Sequence
<220> FEATURE:
<223> OTHER INFORMATION: synthetic construct; mutated BAD

<400> SEQUENCE: 7

```
atgttccaga tcccagagtt tgagccgagt gagcaggaag actccagctc tgcagagagg     60
ggcctgggcc ccagccccgc aggggacggg ccctcaggct ccggcaagca tcatcgccag    120
gccccaggcc tcctgtggga cgccagtcac cagcaggagc agccaaccag cagcagccat    180
catggaggcg ctggggctgt ggagatccgg agtcgccaca gcgcctaccc cgcggggacg    240
gaggacgacg aagggatggg ggaggagccc agccccttc ggggccgctc gcgcgcagcg     300 cccccccaacc tctgggcagc acagcgctat ggccgcgagc tccggaggat gagtgacgag    360
tttgtggact ccttttaagaa gggacttcct cgcccgaaga gcgcgggcac agcaacgcag    420
atgcggcaaa gctccagctg gacgcgagtc ttccagtcct ggtgggatcg gaacttgggc    480
aggggaagct ccgccccctc ccagtga                                       507
```

<210> SEQ ID NO 8
<211> LENGTH: 1695
<212> TYPE: DNA
<213> ORGANISM: Artificial Sequence

```
<220> FEATURE:
<223> OTHER INFORMATION: synthetic construct; p53 operably linked to
      mutated BAD

<400> SEQUENCE: 8
atggaggagc cgcagtcaga tcctagcgtc gagccccctc tgagtcagga aacattttca      60
gacctatgga aactacttcc tgaaaacaac gttctgtccc ccttgccgtc ccaagcaatg     120
gatgatttga tgctgtcccc ggacgatatt gaacaatggt tcactgaaga cccaggtcca     180
gatgaagctc ccagaatgcc agaggctgct ccccccgtgg cccctgcacc agcagctcct     240
acaccggcgg cccctgcacc agccccctcc tggcccctgt catcttctgt cccttcccag     300
aaaacctacc agggcagcta cggtttccgt ctgggcttct gcattctggg acagccaag     360
tctgtgactt gcacgtactc ccctgccctc aacaagatgt tttgccaact ggccaagacc     420
tgccctgtgc agctgtgggt tgattccaca ccccgcccg caccgcgt ccgcgccatg       480
gccatctaca gcagtcaca gcacatgacg gaggttgtga ggcgctgccc ccaccatgag     540
cgctgctcag atagcgatgg tctggcccct cctcagcatc ttatccgagt ggaaggaaat     600
ttgcgtgtgg agtatttgga tgacagaaac acttttcgac atagtgtggt ggtgccctat     660
gagccgcctg aggttggctc tgactgtacc accatccact acaactacat gtgtaacagt     720
tcctgcatgg gcggcatgaa ccggaggccc atcctcacca tcatcacact ggaagactcc     780
agtggtaatc tactgggacg gaacagcttt gaggtgcgtg tttgtgcctg tcctgggaga     840
gaccggcgca cagaggaaga gaatctccgc aagaaggggg agcctcacca cgagctgccc     900
ccagggagca ctaagcgagc actgcccaac aaccagct cctctcccca gccaaagaag       960
aaaccactgg atggagaata tttcaccctt cagatccgtg ggcgtgagcg cttcgagatg    1020
ttccgagagc tgaatgaggc cttggaactc aaggatgccc aggctgggaa ggagccaggg    1080
gggagcaggg ctcactccag ccacctgaag tccaaaaagg gtcagtctac ctcccgccat    1140
aaaaaactca tgttcaagac agaagggcct gactcagact taggtaccat gttccagatc    1200
ccagagtttg agccgagtga gcaggaagac tccagctctg cagagagggg cctgggcccc    1260
agccccgcag gggacgggcc ctcaggctcc ggcaagcatc atcgccaggc cccaggcctc    1320
ctgtgggacg ccagtcacca gcaggagcag ccaaccagca gcagccatca tggaggcgct    1380
ggggctgtgg agatccggag tcgccacagc gcctaccccg cggggacgga ggacgacgaa    1440
gggatggggg aggagcccag ccccttcggg ggccgctcgc gcgcagcgcc ccccaacctc    1500
tgggcagcac agcgctatgg ccgcgagctc cggaggatga gtgacgagtt tgtggactcc    1560
tttaagaagg gacttcctcg cccgaagagc gcgggcacag caacgcagat gcggcaaagc    1620
tccagctgga cgcgagtctt ccagtcctgg tgggatcgga acttgggcag gggaagctcc    1680
gcccctccc agtga                                                      1695

<210> SEQ ID NO 9
<211> LENGTH: 15
<212> TYPE: PRT
<213> ORGANISM: Artificial Sequence
<220> FEATURE:
<223> OTHER INFORMATION: synthetic construct; linker

<400> SEQUENCE: 9

Gly Gly Gly Gly Ser Gly Gly Gly Gly Ser Gly Gly Gly Gly Ser
1               5                   10                  15

<210> SEQ ID NO 10
```

```
<211> LENGTH: 18
<212> TYPE: PRT
<213> ORGANISM: Artificial Sequence
<220> FEATURE:
<223> OTHER INFORMATION: synthetic construct; linker

<400> SEQUENCE: 10

Pro Ala Pro Ala Pro Ala Pro Ala Pro Ala Pro Ala Pro Ala Pro Ala
1               5                   10                  15

Pro Ala

<210> SEQ ID NO 11
<211> LENGTH: 15
<212> TYPE: PRT
<213> ORGANISM: Artificial Sequence
<220> FEATURE:
<223> OTHER INFORMATION: synthetic construct; linker

<400> SEQUENCE: 11

Glu Ala Ala Ala Lys Glu Ala Ala Ala Lys Glu Ala Ala Ala Lys
1               5                   10                  15

<210> SEQ ID NO 12
<211> LENGTH: 48
<212> TYPE: PRT
<213> ORGANISM: Artificial Sequence
<220> FEATURE:
<223> OTHER INFORMATION: synthetic construct; linker

<400> SEQUENCE: 12

Leu Glu Ala Glu Ala Ala Ala Lys Glu Ala Ala Ala Lys Glu Ala Ala
1               5                   10                  15

Ala Lys Glu Ala Ala Ala Lys Leu Glu Ala Glu Ala Ala Ala Lys Glu
                20                  25                  30

Ala Ala Ala Lys Glu Ala Ala Ala Lys Glu Ala Ala Ala Lys Leu Glu
            35                  40                  45
```

P53-BAD FUSION PROTEINS

CROSS-REFERENCE TO RELATED APPLICATIONS

This application claims benefit of U.S. Provisional Application No. 62/672,372, filed May 16, 2018, and is hereby incorporated herein by reference in its entirety.

STATEMENT REGARDING FEDERALLY SPONSORED RESEARCH

This invention was made with government support under Grant Number R21 CA187289 awarded by The National Institutes of Health. The government has certain rights in the invention.

REFERENCE TO SEQUENCE LISTING

The Sequence Listing submitted Aug. 16, 2019 as a text file named "21101_0393U2_Sequence_Listing.txt," created on Aug. 1, 2019, and having a size of 16,194 bytes is hereby incorporated by reference pursuant to 37 C.F.R. § 1.52(e)(5).

BACKGROUND

Genetic heterogeneity and drug resistance are unresolved fundamental problems for cancer therapy that make personalized medicine for cancer elusive. Inter- and intra-tumoral genetic variations, as well as tumor evolution due to pressure from various treatments keep cancer as a "moving target," squelching the success of new drugs targeted to specific pathways implicated in cancer. This disclosure reports a gene therapy construct that combines the power of mitochondrial p53 with BH3 apoptotic sensitizer proteins. p53 can bind to and activate pro-apoptotic proteins Bak and Bax and neutralize anti-apoptotic proteins Mcl-1, Bcl-XL, Bcl-2, and BclW. Pro- and anti-apoptotic Bcl-2 family members contain various Bcl-2 homology (BH) domains, named BH1-4. Pro-apoptotic factors Bim, Bad, Bid, Noxa, and Puma are so-called "BH3 only proteins," and are considered to be death effector molecules. P53-BH3 is a gene therapy construct that indicates robust killing of cancer cells with the p53-BH3 construct driven by a CMV promoter.

The "moving target" of inter- and intra-tumoral genetic variations exist for ovarian cancer patients, who initially respond to chemotherapy, but eventually relapse and develop drug resistance. Because of its high heterogeneity with 15+ implicated oncogenes and 168 epigenetic alterations, targeted therapy for ovarian cancer has not succeeded. Whole genome sequencing found that 96% of high grade serous carcinoma (HGSC) patients have mutation/loss of function of p53 tumor suppressor. p53 tumor suppressor gene therapy was attempted in the late 1990's as a potent inducer of apoptosis. However, in clinical trials, wild-type (wt) p53 gene therapy failed for ovarian cancer treatment due to: multiple genetic changes in cancer, dominant negative inhibition (dimerization and inactivation) of p53 by mutant p53 in cancer cells, lack of tumor targeting, and immunogenicity with adenoviral delivery of the gene. p53 has been used to exploit apoptosis via nuclear gene activation including the past failed clinical trials, the intrinsic mitochondrial apoptotic pathway may be more appealing due to its rapid, direct apoptotic effects at the mitochondria and absence of dominant negative inhibition. p53 directed to the mitochondria functions as a monomer, and its rapid effects are the shortest pathway for executing p53 death signaling, which triggers a wave of caspase activation and apoptosis. p53 can bind to pro-apoptotic Bak and Bax, allowing for their homo-oligomerization, leading to mitochondrial outer membrane permeabilization (pore formation), cytochrome C release, and activation of the caspase cascade.

High grade serous carcinoma (HGSC) is the most common type of ovarian cancer, and accounts for 70-80% of ovarian cancer deaths. While most patients initially respond to standard-of-care platinum-based chemotherapy, resistance usually emerges. Ovarian cancer is the most lethal gynecological malignancy with 70% of patients succumbing to their disease. Although newer drugs are being tested, their success may depend on patient-specific heterogeneous genomic factors.

BRIEF SUMMARY

Disclosed are peptides comprising a p53 peptide and a BH3-only protein. In some aspects, wherein the BH3-only protein is BAD, BID, BIM, NOXA.

Disclosed are nucleic acid sequences comprising a sequence capable of encoding a p53 peptide operably linked to a nucleic acid sequence capable of encoding a BH3-only protein.

Disclosed are nucleic acid sequences comprising a sequence capable of encoding one or more of the peptides disclosed herein.

Disclosed are vectors comprising a nucleic acid sequence, wherein the nucleic acid sequence is capable of encoding one or more of the peptides disclosed herein.

Disclosed are methods of inducing apoptosis comprising administering one or more of the peptides or a nucleic acid sequences disclosed herein.

Disclosed are methods of targeting a peptide to mitochondria comprising introducing a peptide to a cell, wherein the peptide is one or more of the peptides disclosed herein.

Disclosed are methods of inducing homo-oligomerization of Bak or Bax comprising administering a peptide or a nucleic acid sequences of any one of those disclosed herein.

Disclosed are methods of treating a hyperproliferative disorder in a patient comprising administering to the patient a peptide or a nucleic acid sequence disclosed herein.

Disclosed are methods of treating a hyperproliferative disorder in a patient comprising administering to the patient a nucleic acid sequence disclosed herein.

Disclosed are cells comprising a peptide, a nucleic acid or a vector disclosed herein.

Disclosed are subjects comprising the peptide, the nucleic acid, or the vector disclosed herein.

Disclosed are transgenic, non-human subjects comprising the peptide, the nucleic acid, or the vector disclosed herein.

Additional advantages of the disclosed method and compositions will be set forth in part in the description which follows, and in part will be understood from the description, or may be learned by practice of the disclosed method and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed method and compositions and together with the description, serve to explain the principles of the disclosed method and compositions.

DETAILED DESCRIPTION

Figure 1:
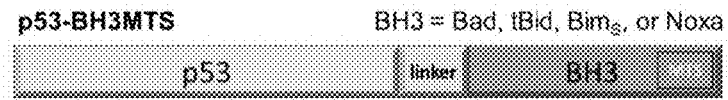
FIG. 1 shows a representation of a p53-BH3 fusion. The p53 and BH3 domains have apoptotic activity; the embedded MTS in BH3 directs it to the mitochondria. The BH3-only protein must be attached to the C-terminus of p53 to maintain its C-terminal tail-anchored mitochondrial targeting signal (MTS) activity.

The disclosed method and compositions may be understood more readily by reference to the following detailed description of particular embodiments and the Example included therein and to the Figures and their previous and following description.

It is to be understood that the disclosed method and compositions are not limited to specific synthetic methods, specific analytical techniques, or to particular reagents unless otherwise specified, and, as such, may vary. It is also to be understood that the terminology used herein is for the purpose of describing particular embodiments only and is not intended to be limiting.

Disclosed are materials, compositions, and components that can be used for, can be used in conjunction with, can be used in preparation for, or are products of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a peptide is disclosed and discussed and a number of modifications that can be made to a number of molecules including the amino acids are discussed, each and every combination and permutation of the peptide and the modifications that are possible are specifically contemplated unless specifically indicated to the contrary. Thus, if a class of molecules A, B, and C are disclosed as well as a class of molecules D, E, and F and an example of a combination molecule, A-D is disclosed, then even if each is not individually recited, each is individually and collectively contemplated. Thus, is this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

A. Definitions

It is understood that the disclosed method and compositions are not limited to the particular methodology, protocols, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a peptide" includes a plurality of such peptides, reference to "the nucleic acid sequence" is a reference to one or more nucleic acid sequences and equivalents thereof known to those skilled in the art, and so forth.

"Peptide" as used herein refers to any polypeptide, oligopeptide, gene product, expression product, or protein. A peptide is comprised of consecutive amino acids. The term "peptide" encompasses recombinant, naturally occurring and synthetic molecules.

In addition, as used herein, the term "peptide" refers to amino acids joined to each other by peptide bonds or modified peptide bonds, e.g., peptide isosteres, etc. and may contain modified amino acids other than the 20 gene-encoded amino acids. The peptides can be modified by either natural processes, such as post-translational processing, or by chemical modification techniques which are well known in the art. Modifications can occur anywhere in the polypeptide, including the peptide backbone, the amino acid side-chains and the amino or carboxyl termini. The same type of modification can be present in the same or varying degrees at several sites in a given peptide. Also, a given peptide can have many types of modifications. Modifications include, without limitation, acetylation, acylation, ADP-ribosylation, amidation, covalent cross-linking or cyclization, covalent attachment of flavin, covalent attachment of a heme moiety, covalent attachment of a nucleotide or nucleotide derivative, covalent attachment of a lipid or lipid derivative, covalent attachment of a phosphytidylinositol, disulfide bond formation, demethylation, formation of cysteine or pyroglutamate, formylation, gamma-carboxylation, glycosylation, GPI anchor formation, hydroxylation, iodination, methylation, myristolyation, oxidation, pergy- lation, proteolytic processing, phosphorylation, prenylation, racemization, selenoylation, sulfation, and transfer-RNA mediated addition of amino acids to protein such as arginylation. (See Proteins—Structure and Molecular Properties 2nd Ed., T. E. Creighton, W.H. Freeman and Company, New York (1993); Posttranslational Covalent Modification of Proteins, B. C. Johnson, Ed., Academic Press, New York, pp. 1-12 (1983)).

As used herein, the term "amino acid sequence" refers to a list of abbreviations, letters, characters or words representing amino acid residues.

The amino acid abbreviations used herein are conventional one letter codes for the amino acids and are expressed as follows: A, alanine; B, asparagine or aspartic acid; C, cysteine; D aspartic acid; E, glutamate, glutamic acid; F, phenylalanine; G, glycine; H histidine; I isoleucine; K, lysine; L, leucine; M, methionine; N, asparagine; P, proline; Q, glutamine; R, arginine; S, serine; T, threonine; V, valine; W, tryptophan; Y, tyrosine; Z, glutamine or glutamic acid.

The phrase "nucleic acid" as used herein refers to a naturally occurring or synthetic oligonucleotide or polynucleotide, whether DNA or RNA or DNA-RNA hybrid, single-stranded or double-stranded, sense or antisense, which is capable of hybridization to a complementary nucleic acid by Watson-Crick base-pairing. Nucleic acids of the invention can also include nucleotide analogs (e.g., BrdU), and non-phosphodiester internucleoside linkages (e.g., peptide nucleic acid (PNA) or thiodiester linkages). In particular, nucleic acids can include, without limitation, DNA, RNA, cDNA, gDNA, ssDNA, dsDNA or any combination thereof By "sample" is meant an animal; a tissue or organ from an animal; a cell (either within a subject, taken directly from a subject, or a cell maintained in culture or from a cultured cell line); a cell lysate (or lysate fraction) or cell extract; or a solution containing one or more molecules derived from a cell or cellular material (e.g. a polypeptide or nucleic acid), which is assayed as described herein. A sample may also be any body fluid or excretion (for example, but not limited to, blood, urine, stool, saliva, tears, bile) that contains cells or cell components.

By an "effective amount" of a composition as provided herein is meant a sufficient amount of the composition to provide the desired effect. The exact amount required will vary from subject to subject, depending on the species, age, and general condition of the subject, the severity of disease (or underlying genetic defect) that is being treated, the particular composition used, its mode of administration, and the like. Thus, it is not possible to specify an exact "effective amount." However, an appropriate "effective amount" may be determined by one of ordinary skill in the art using only routine experimentation.

By "transgenic animal" is meant an animal comprising a transgene as described above. Transgenic animals are made by techniques that are well known in the art.

By "treat" is meant to administer a peptide, nucleic acid, vector, or composition of the invention to a subject, such as a human or other mammal (for example, an animal model), that has an increased susceptibility for developing a hyperproliferative disorder, or that has a hyperproliferative disorder, in order to prevent or delay a worsening of the effects of the disease or condition, or to partially or fully reverse the effects of the disease. For example, the hyperproliferative disorder can be cancer.

By "prevent" is meant to minimize the chance that a subject who has an increased susceptibility for developing a disease will develop the disease.

By "specifically binds" is meant that an antibody recognizes and physically interacts with its cognate antigen (for example, a p53 peptide) and does not significantly recognize and interact with other antigens; such an antibody may be a polyclonal antibody or a monoclonal antibody, which are generated by techniques that are well known in the art.

Throughout the description and claims of this specification, the word "comprise" and variations of the word, such as "comprising" and "comprises," means "including but not limited to," and is not intended to exclude, for example, other additives, components, integers or steps. In particular, in methods stated as comprising one or more steps or operations it is specifically contemplated that each step comprises what is listed (unless that step includes a limiting term such as "consisting of"), meaning that each step is not intended to exclude, for example, other additives, components, integers or steps that are not listed in the step.

The term "wild type p53 (wt p53)" refers to the p53 sequence of.

(SEQ ID NO: 3)

```
MEEPQSDPSV EPPLSQETFS DLWKLLPENN VLSPLPSQAM

DDLMLSPDDI EQWFTEDPGP DEAPRMPEAA PPVAPAPAAP

TPAAPAPAPS WPLSSSVPSQ KTYQGSYGFR LGFLHSGTAK

SVTCTYSPAL NKMFCQLAKT CPVQLWVDST PPPGTRVRAM

AIYKQSQHMT EVVRRCPHHE RCSDSDGLAP PQHLIRVEGN

LRVEYLDDRN TFRHSVVVPY EPPEVGSDCT TIHYNYMCNS

SCMGGMNRRP ILTIITLEDS SGNLLGRNSF EVRVCACPGR

DRRTEEENLR KKGEPHHELP PGSTKRALPN NTSSSPQPKK

KPLDGEYFTL QIRGRERFEM FRELNEALEL KDAQAGKEPG

GSRAHSSHLK SKKGQSTSRH KKLMFKTEGP DSD
```

Wild type p53 can be divided into three regions: an acidic N-terminal region (amino acids 1-101 of SEQ ID NO:3), a DNA binding domain (DBD, amino acids 102-292 of SEQ ID NO:3), and a basic C-terminal region (amino acids 293-393 of SEQ ID NO:3). The acidic N-terminal region contains a transactivation acidic domain (amino acids 1-42 of SEQ ID NO:3), a MDM2 binding domain (MBD, amino acids 17-28 of SEQ ID NO:3), and a proline-rich domain (PRD, amino acids 63-97 of SEQ ID NO:3). The basic C terminal region contains three nuclear localization signals (NLS, acids 305-322 most active NLS of SEQ ID NO:3), a tetramerization domain (TD, amino acids 323-356 of SEQ ID NO:3), and a negative regulatory region (amino acids 363-393 of SEQ ID NO:3).

The term "full-length p53 peptide" refers to the full length wild type p53 peptide. A full-length p53 peptide comprises all of the functional domains of wild type p53. For example, a full-length p53 peptide comprises the DNA binding domain, MDM2 binding domain, proline-rich domain, tetramerization domain, and transactivation domain of wt p53. A full-length p53 peptide can comprise the acidic N-terminal region (amino acids 1-101) of SEQ ID NO:3, a DNA binding domain (DBD, amino acids 102-292) of SEQ ID NO:3, and a basic C-terminal region (amino acids 293-393) of SEQ ID NO:3. The acidic N-terminal region contains a transactivation acidic domain (amino acids 1-42 of SEQ ID NO:3), a MDM2 binding domain (MBD, amino acids 17-28 of SEQ ID NO:3), and a proline-rich domain (PRD, amino acids 63-97 of SEQ ID NO:3). The basic C terminal region contains three nuclear localization signals (NLS, acids 305-322 most active NLS of SEQ ID NO:3), a tetramerization domain (TD, amino acids 323-356 of SEQ ID NO:3), and a negative regulatory region (amino acids 363-393 of SEQ ID NO:3).

The term "partial p53 peptide" refers to a p53 sequence peptide that has less than the full length wild type p53 peptide sequence. In some instances, a partial p53 peptide can lack one or more of the wild type p53 domains. Thus, a partial p53 peptide can comprise one or more domains of p53 without comprising all of the domains of wild type p53. For example, a partial p53 peptide can be a peptide comprising only the DNA binding domain of p53 (amino acids 102-292 of SEQ ID NO:3) or a combination of the DNA binding domain of p53 with one or more of the other p53 peptide domains, but not all of the p53 peptide domains. A partial p53 peptide comprising the DNA binding domain of p53 with one or more of the other p53 peptide domains, but not all of the p53 peptide domains, can comprise a DNA binding domain and at least one other p53 peptide domain wherein the at least one other p53 peptide domain comprises the transactivation domain (amino acids 1-42 of SEQ ID NO:3), MDM2 binding domain (MBD, amino acids 17-28 of SEQ ID NO:3), proline-rich domain (PRD, amino acids 63-97 of SEQ ID NO:3), tetramerization domain (TD, amino acids 323-356 of SEQ ID NO:3) of wt p$53$. In some aspects the DNA binding domain and the other p53 peptide domain comprise one, two, three, four, five, six, seven, eight, or nine additional amino acids on the C-terminal end of the domain, N-terminal end of the domain, or a combination.

"Optional" or "optionally" means that the subsequently described event, circumstance, or material may or may not occur or be present, and that the description includes instances where the event, circumstance, or material occurs or is present and instances where it does not occur or is not present.

Ranges may be expressed herein as from "about" one particular value, and/or to "about" another particular value. When such a range is expressed, also specifically contemplated and considered disclosed is the range from the one particular value and/or to the other particular value unless the context specifically indicates otherwise. Similarly, when values are expressed as approximations, by use of the antecedent "about," it will be understood that the particular value forms another, specifically contemplated embodiment that should be considered disclosed unless the context specifically indicates otherwise. It will be further understood that the endpoints of each of the ranges are significant both in relation to the other endpoint, and independently of the other endpoint unless the context specifically indicates otherwise. Finally, it should be understood that all of the individual values and sub-ranges of values contained within an explicitly disclosed range are also specifically contemplated and should be considered disclosed unless the context specifically indicates otherwise. The foregoing applies regardless of whether in particular cases some or all of these embodiments are explicitly disclosed.

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinency of the cited documents. It will be clearly understood that, although a number of publications are referred to herein, such reference does not constitute an admission that any of these documents forms part of the common general knowledge in the art.

Throughout the description and claims of this specification, the word "comprise" and variations of the word, such as "comprising" and "comprises," means "including but not limited to," and is not intended to exclude, for example, other additives, components, integers or steps. In particular, in methods stated as comprising one or more steps or operations it is specifically contemplated that each step comprises what is listed (unless that step includes a limiting term such as "consisting of"), meaning that each step is not intended to exclude, for example, other additives, components, integers or steps that are not listed in the step.

B. Peptides

Disclosed are peptides comprising a p53 peptide and a BH3-only protein.

In some aspects, the BH3-only protein can be BAD, BID, BIM, NOXA. In some aspects, the BH3-only protein is BAD. In some aspects, BAD comprises the amino acid sequence of MFQIPEFEPSEQEDSSSAER-GLGPSPAGDGPSGSGKHHRQAPGLLW-DASHQQEQPTSSSH HGGAGAVEIRSRHSSYPAGTED-DEGMGEEPSPFRGRSRSAPPNLWAAQRYGRELRRMS DEFVDSFKKGLPRPKSAGTATQMRQSSS-WTRVFQSWWDRNLGRGSSAPSQ (SEQ ID NO: 1). In some aspects, BAD consists of the amino acid sequence of SEQ ID NO: 1.

In some aspects, the BH3-only protein can be mutated. In some aspects, the BH3-only protein that is mutated can be a mutated BAD. For example, the mutated BAD can have a serine to alanine substitution at one or more of positions 112, 136, and 155. In some aspects, the mutated BAD has a serine to alanine substitution at positions 112 and 136. Thus, in some aspects, the mutated BAD comprises an amino acid sequence of MFQIPEFEPSEQEDSSSAER-GLGPSPAGDGPSGSGKHHRQAPGLLW-DASHQQEQPTSSSH HGGAGAVEIRSRHSAYPAGTED-DEGMGEEPSPFRGRSRAAPPNLWAAQRYGRELRRMS DEFVDSFKKGLPRPKSAGTATQMRQSSS-WTRVFQSWWDRNLGRGSSAPSQ (SEQ ID NO:2). In some aspects, the mutated BAD consists of an amino acid sequence of SEQ ID NO:2.

In some aspects, the p53 peptide is a full length p53. Full length p53 can comprise the sequence of MEEPQSDPSV EPPLSQETFS DLWKLLPENN VLSPLPSQAM DDLML-SPDDI EQWFTEDPGP DEAPRMPEAA PPVAPAPAAP TPAAPAPAPS WPLSSSVPSQ KTYQGSYGFR LGFLHSGTAK SVTCTYSPAL NKMFCQLAKT CPVQLWVDST PPPGTRVRAM AIYKQSQHMT EVVRRCPHHE RCSDSDGLAP PQHLIRVEGN LRVEY-LDDRN TFRHSVVVPY EPPEVGSDCT TIHYNYMCNS SCMGGMNRRP ILTIITLEDS SGNLLGRNSF EVRVCACPGR DRRTEEENLR KKGEPHHELP PGSTKRALPN NTSSSPQPKK KPLDGEYFTL QIRGR-ERFEM FRELNEALEL KDAQAGKEPG GSRAHSSHLK SKKGQSTSRH KKLMFKTEGP DSD (SEQ ID NO:3). In some aspects, full length p53 consists of the sequence of SEQ ID NO:3. In some aspects, the p53 peptide can be a partial p53 peptide, wherein the partial p53 peptide retains pro-apoptotic function. For example, the partial p53 peptide can be a fragment of SEQ ID NO:3. In some aspects, the fragment of SEQ ID NO:3 can be any amino acid sequence of SEQ ID NO:3 that is less than the full length that retains pro-apoptotic function. In some aspects, the partial p53 peptide consists of the DNA binding domain of p53. In some aspects, the partial p53 peptide comprises the DNA binding domain of p53. In some aspects, the partial p53 peptide consists of amino acids 102-292 of SEQ ID NO:3. In some aspects, amino acids 102-292 of SEQ ID NO:3 are TYQGSYGFRLGFLHSGTAKSVTCTYSPAL-NKMFCQLAKTCPVQLWVDSTPPPGTRVRA MAIYKQSQHMTEVVRRCPHHERCSDSDGLAPPQH-LIRVEGNLRVEYLDDRNTFRHSVV VPYEPPE-VGSDCTTIHYNYMCNSSCMGGMNRRPILTIITLED-SSGNLLGRNSFEVRVCAC PGRDRRTEEENLRKK (SEQ ID NO:4). In some aspects, the partial p53 peptide comprises the DNA binding domain of p53 and further comprises a MDM2 binding domain, a proline-rich domain, a tetramerization domain, or a transactivation domain of p53.

In some aspects, the disclosed peptides can further comprise a linker between the p53 peptide and the BH3-only protein. For example, the linker can be (GGGGS)$_3$ (SEQ ID NO:9), (PAPAPA)$_3$ (SEQ ID NO: 10), (EAAAK)$_3$ (SEQ ID NO: 11), or [LEA(EAAAK)$_4$]$_2$LE (SEQ ID NO: 12).

Protein variants and derivatives are well understood to those of skill in the art and can involve amino acid sequence modifications. For example, amino acid sequence modifications typically fall into one or more of three classes: substitutional, insertional or deletional variants. Polypeptide variants or derivatives generally encompassed by the present invention will typically exhibit at least about 70%, 75%, 80%, 85%, 90%, 91%, 92%, 93%, 94%, 95%, 96%, 97%, 98%, or 99% or more identity (determined as described below), along its length, to a polypeptide sequences set forth herein.

In some aspects, disclosed are protein variants and derivatives that comprise one or more of the sequences disclosed herein and vary from those sequences by one or more amino acids. For example, disclosed herein are protein variants and derivatives that comprise one or more of the sequences disclosed herein, wherein 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acids differ from the sequences disclosed herein.

1. Compositions Comprising Peptides

Disclosed are compositions comprising one or more of the peptides described herein. For example, disclosed are compositions comprising a peptide, wherein the peptide comprises a p53 peptide and a BH3-only protein. In some aspects, the BH3-only protein can be BAD, BID, BIM, NOXA. In some aspects, the BH3-only protein is BAD. For example, BAD can comprise the amino acid sequence of SEQ ID NO: 1.

Disclosed are compositions comprising a peptide, wherein the peptide comprises a p53 peptide and a BH3-only protein, wherein the BH3-only protein can be mutated. In some aspects, the BH3-only protein that is mutated can be a mutated BAD. For example, the mutated BAD can have a serine to alanine substitution at one or more of positions 112, 136, and 155. In some aspects, the mutated BAD has a serine to alanine substitution at positions 112 and 136. Thus, in some aspects, the mutated BAD has an amino acid sequence of SEQ ID NO:2.

In some aspects, the compositions comprising a peptide, wherein the peptide comprises a p53 peptide and a BH3- only protein can have either a full length p53 or a partial p53 peptide that retains pro-apoptotic function. In some aspects, a full length p53 can have the sequence of SEQ ID NO:3. In some aspects, the partial p53 peptide can be a fragment of SEQ ID NO:3. In some aspects, the fragment of SEQ ID NO:3 can be any amino acid sequence of SEQ ID NO:3 that is less than the full length that retains pro-apoptotic function. In some aspects, the partial p53 peptide consists of the DNA binding domain of p53. In some aspects, the partial p53 peptide comprises the DNA binding domain of p53. In some aspects, the partial p53 peptide consists of amino acids 102-292 of SEQ ID NO:3. In some aspects, the partial p53 peptide comprises the DNA binding domain of p53 and further comprises a MDM2 binding domain, a proline-rich domain, a tetramerization domain, or a transactivation domain of p53.

Disclosed are compositions comprising a peptide, wherein the peptide comprises a p53 peptide and a BH3-only protein and wherein the peptides can further comprise a linker between the p53 peptide and the BH3-only protein. For example, the linker can be (GGGGS)$_3$ (SEQ ID NO:9), (PAPAPA)$_3$ (SEQ ID NO: 10), (EAAAK)$_3$ (SEQ ID NO: 11), or [LEA(EAAAK)$_4$]$_2$LE (SEQ ID NO: 12).

2. Peptide Variants

Also disclosed herein are peptide variants of the peptides disclosed herein. Peptide variants and derivatives are well understood by those of skill in the art and can involve amino acid sequence modifications. For example, amino acid sequence modifications typically fall into one or more of three classes: substitutional, insertional or deletional variants. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Deletions are characterized by the removal of one or more amino acid residues from the peptide sequence. These variants ordinarily are prepared by site specific mutagenesis of nucleotides in the DNA encoding the protein, thereby producing DNA encoding the variant, and thereafter expressing the DNA in recombinant cell culture. Techniques for making substitution mutations at predetermined sites in DNA having a known sequence are well known, for example M13 primer mutagenesis and PCR mutagenesis. Amino acid substitutions are typically of single residues, but can occur at a number of different locations at once; insertions usually will be on the order of about from 1 to 10 amino acid residues; and deletions will range about from 1 to 30 residues. Deletions or insertions preferably are made in adjacent pairs, i.e. a deletion of 2 residues or insertion of 2 residues. Substitutions, deletions, insertions or any combination thereof may be combined to arrive at a final construct. The mutations must not place the sequence out of reading frame and preferably will not create complementary regions that could produce secondary mRNA structure. Substitutional variants are those in which at least one residue has been removed and a different residue inserted in its place.

Conservative and non-conservative substitutions can be made. For example, the replacement of one amino acid residue with another that is biologically and/or chemically similar is known to those skilled in the art as a conservative substitution. For example, a conservative substitution would be replacing one hydrophobic residue for another, or one polar residue for another. The substitutions include combinations such as, for example, Gly, Ala; Val, Ile, Leu; Asp, Glu; Asn, Gin; Ser, Thr; Lys, Arg; and Phe, Tyr. Such conservatively substituted variations of each explicitly disclosed sequence are included within the mosaic polypeptides provided herein.

Substitutional or deletional mutagenesis can be employed to insert sites for N-glycosylation (Asn-X-Thr/Ser) or O-glycosylation (Ser or Thr). Deletions of cysteine or other labile residues also may be desirable. Deletions or substitutions of potential proteolysis sites, e.g. Arg, is accomplished for example by deleting one of the basic residues or substituting one by glutaminyl or histidyl residues.

Certain post-translational derivatizations are the result of the action of recombinant host cells on the expressed polypeptide. Glutaminyl and asparaginyl residues are frequently post-translationally deamidated to the corresponding glutamyl and asparyl residues. Alternatively, these residues are deamidated under mildly acidic conditions. Other post-translational modifications include hydroxylation of proline and lysine, phosphorylation of hydroxyl groups of seryl or threonyl residues, methylation of the o-amino groups of lysine, arginine, and histidine side chains (T. E. Creighton, Proteins: Structure and Molecular Properties, W.H. Freeman & Co., San Francisco pp 79-86 [1983]), acetylation of the N-terminal amine and, in some instances, amidation of the C-terminal carboxyl.

It is understood that one way to define the variants and derivatives of the disclosed peptides herein is through defining the variants and derivatives in terms of homology/identity to specific known sequences. For example, the sequence of wild type p53 is known. For example, wild type p53 is provided herein as SEQ ID NO:3. Specifically disclosed are variants of these and other peptides herein disclosed which have at least, 70% or 75% or 80% or 85% or 90% or 95% homology to the full length or a fragment of wild type sequence. Wherein a sequence is said to have at least about 70% sequence identity, it is understood to also have at least about 75%, 80%, 85%, 90%, 92%, 92%, 93%, 94%, 95%, 96%, 97%, 98%, 99%, or 100% sequence identity.

C. Nucleic Acid Sequences

Also disclosed herein are nucleic acid sequences capable of encoding the peptides disclosed herein. For example, disclosed are nucleic acid sequences comprising a sequence capable of encoding a p53 peptide operably linked to a nucleic acid sequence capable of encoding a BH3-only protein.

Disclosed are nucleic acid sequences comprising a sequence capable of encoding a p53 peptide operably linked to a nucleic acid sequence capable of encoding a BH3-only protein wherein the BH3-only protein is BAD, BID, BIM, NOXA. In some aspects, the BH3-only protein can be BAD. In some aspects, the nucleic acid sequence capable of encoding BAD as the BH3-only protein can comprise the nucleic acid sequence of ATGTTCCAGATCCCAGAGTTT-GAGCCGAGTGAGCAGGAA-GACTCCAGCTCTGCAGA GAGGGGCCTGGGCCCCAGCCCCGCAGGGGACGGG CCCTCAGGCTCCGGCAAGCATC ATCGCCAGGCCCCAGGCCTCCTGTGGGACGCCAGT-CACCAGCAGGAGCAGCCAACC AGCAGCAGCCAT-CATGGAGGCGCTGGGGCTGTGGAGATCCG-GAGTCGCCACAGCTC CTACCCCGCGGGGACGGAGGACGACGAAGG-GATGGGGAGGAGCCCAGCCCCT CGGGGCCGCTCGCGCTCGGCGCCCCC-CAACCTCTGGGCAGCACAGCGCTATGGCCG CGAGCTCCGGAGGAT-GAGTGACGAGTTTGTGGACTCCTAAGAAGGGACTC CTC GCCCGAAGAGCGCGGGCACAGCAACGCA- GATGCGGCAAAGCTCCAGCTGGACGCGAGTCTFCCAGTCCTGGTGGGATCG-GAACTFGGGCAGGGGAAGCTCCGCCCCCTCCCAGTGA (SEQ ID NO:5). In some aspects, the nucleic acid sequence of BAD consists of SEQ ID NO:5.

Disclosed are nucleic acid sequences comprising a sequence capable of encoding a p53 peptide operably linked to a nucleic acid sequence capable of encoding a BH3-only protein, wherein the BH3-only protein is BAD, wherein the nucleic acid sequence comprises the sequence of ATGGAGGAGCCGCAGTCA-GATCCTAGCGTTCGAGCCCCCTCTGAGTCAGGAAACATT TCAGACCTATGGAAACTACTCCT-GAAAACAACGTCTGTCCCCCTTGCCGTCCCA AGCAATGGATGATGATGCTGTCCCCGGACGATATT-GAACAATGGTTCACTGAAG ACCCAGGTCCAGAT-GAAGCTCCCAGAATGCCAGAGGCTGCTCCCCCGT GGCCCCT GCACCAGCAGCTCCTA-CACCGGCGGCCCCTGCACCAGCCCCTCCTGGCC CCTGTCA TCTCTGTCCCTCCCAGAAAACC-TACCAGGGCAGCTACGGTTCCGTCTGGGCTC TTG-CATTCTGGGACAGC-CAAGTCTGTGACTTGCACGTACTCCCCTGCCCTCA ACAAG ATGTTTTGCCAACTGGCCAA-GACCTGCCCTGTGCAGCTGTGGGTTGATTrC-CACACCC CCGCCCGGCACCCGCGTCCGCGC-CATGGCCATCTACAAGCAGTCACAGCACATGAC GGAGGTTGTGAGGCGCTGCCCCCACCAT-GAGCGCTGCTCAGATAGCGATGGTCTGG CCCCTCCTCAGCATCTTATCCGAGTG-GAAGGAAATGCGTGTGGAGTATTTGGATG ACAGAAACACTTTTCGACATAGTGTGGTGGTGCCC-TATGAGCCGCCTGAGGTGGCT CTGACTGTACCAC-CATCCACTACAACTACATGTGTAACAGTTCCTG-CATGGGCGGCA TGAACCGGAGGCCCATCCTCACCATCATCACACTG-GAAGACTCCAGTGGTAATCTA CTGGGACG-GAACAGCTTGAGGTGCGTGTTTGTGCCTGTCCTGG-GAGAGACCGGCG CACAGAGGAAGAGAATCTCCGCAAGAAAGGG-GAGCCTCACCACGAGCTGCCCCCA GGGAGCACTAAGCGAGCACTGCC-CAACAACACCAGCTCCTCTCCCCAGCCAAAGAA GAAACCACTGGATGGAGAATATTTCACCCTCA-GATCCGTGGGCGTGAGCGCTCG AGATGTTCCGAGAGCTGAATGAGGCCTTGGAACT-CAAGGATGCCCAGGCTGGGAAG GAGCCAGGGGG-GAGCAGGGCTCACTCCAGCCACCTGAAGTC-CAAAAAGGGTCAGT CTACCTCCCGCCATAAAAAACTCATGTCAA-GACAGAAGGGCCTGACTCAGAC
<u>TTAGGTACC</u>ATGTTCCAGATCCCAGAGTTTGAGCCGAGTGAGCAGGAAGACTCCAGCT TGCAGAGAGGGCCTGGGCCCCAGCCCCGCAGG GGACGGGCCCTCAGGCTCCGGC AAGCAT-CATCGCCAGGCCCCAGGCCTCCTGTGGGACGCCA GTCACCAGCAGGAGCA GCCAACCAGCAGCAGC-CATCATGGAGGCGCTGGGGCTGTGGAGATCCG-GAGTCGCC ACAGCTCCTACCCCGCGGGACG-GAGGACGACGAAGGGATGGGGGAGGAGCCCAG CCCCTTCGGGGCCGCTCGCGCTCGGCGCCCC-CAACCTCTGGGCAGCACAGCGCTA TGGCCGCGAGCTCCGGAGGAT-GAGTGACGAGTTTGTGGACTCCTTTAAGAAGGGAC TTCCTCGCCCGAAGAGCGCGGGCACAGCAACGCA-GATGCGGCAAAGCTCCAGCTGG ACGCGAGTCTTCCAGTCCTGGTGGGATCG-
GAACTTGGGCAGGGGAAGCTCCGCCCC CTCCCAGTGA (SEQ ID NO:6). The bold sequence is the p53 sequence. The underlined sequence is a linker. The regular font is the BAD.

Disclosed are nucleic acid sequences comprising a sequence capable of encoding a p53 peptide operably linked to a nucleic acid sequence capable of encoding a BH3-only protein, wherein the BH3-only protein is a mutated BAD, wherein the nucleic acid sequence comprises the sequence of ATGTTCCAGATCCCAGAGTTGAGCCGAGT-GAGCAGGAAGACTCCAGCTCTGCAGA GAGGGGCCTGGGCCCCAGCCCCGCAGGGGACGGG CCCTCAGGCTCCGGCAAGCATC ATCGCCAGGCCCCAGGCCTCCTGTGGGACGCCAGT-CACCAGCAGGAGCAGCCAACC AGCAGCAGCCAT-CATGGAGGCGCTGGGGCTGTGGAGATCCG-GAGTCGCCACAGC <u>GCC</u>TACCCCGCGGGGACGGAGGACGACGAAGGGA TGGGGGAGGAGCCCAGCCCCT CGGGGCCGCTCGCGC <u>GCA</u>GCGCCCCCAACCTCTGGGCAGCACAGCGCTA TGGCCG CGAGCTCCGGAGGAT-GAGTGACGAGGGTGGACTCCTAAGAAGGGACTCC CTC GCCCGAAGAGCGCGGGCACAGCAACGCA-GATGCGGCAAAGCTCCAGCTGGACGCG AGTCTTCCAGTCCTGGTGGGATCG-GAACTGGGCAGGGGAAGCTCCGCCCCCTCCC AGTGA (SEQ ID NO:7). The underlined sequences represent the mutations compared to the sequence of SEQ ID NO:5.

Disclosed are nucleic acid sequences comprising a sequence capable of encoding a p53 peptide operably linked to a nucleic acid sequence capable of encoding a BH3-only protein, wherein the BH3-only protein is a mutated BAD, wherein the nucleic acid sequence comprises the sequence of ATGGAGGAGCCGCAGTCA-GATCCTAGCGTCGAGCCCCCTCTGAGTCAGGAAA-CATT TTCAGACCTATGGAAACTACTTCCT-GAAAACAACGTTCTGTCCCCCTTGCCGTCCCA AGCAATGGATGATTGATGCTGTCCCCGGACGATATT-GAACAATGGTTCACTGAAG ACCCAGGTCCAGAT-GAAGCTCCCAGAATGCCAGAGGCTGCTCCCCCGT GGCCCCT GCACCAGCAGCTCCTA-CACCGGCGGCCCCTGCACCAGCCCCTCCTGGCC CTGTCA TCTTCTGTCCCTTCCCAGAAAACC-TACCAGGGCAGCTACGGTTTCCGTCTGGGCTC TTG-CATTCTGGGACAGC-CAAGTCTGTGACTTGCACGTACTCCCCTGCCCTCA ACAAG ATGTTTGCCAACTGGCCAA-GACCTGCCCTGTGCAGCTGTGGGTTGATTC-CACACCC CCGCCCGGCACCCGCGTCCGCGC-CATGGCCATCTACAAGCAGTCACAGCACATGAC GGAGGTTGTGAGGCGCTGCCCCCACCAT-GAGCGCTGCTCAGATAGCGATGGTCTGG CCCCTCCTCAGCATCTTATCCGAGTGGAAGGAAAT-TTGCGTGTGGAGTATTTGGATG ACAGAAACACTTTCGACATAGTGTGGTGGTGCCC-TATGAGCCGCCTGAGGTTGGCT CTGACTGTACCAC-CATCCACTACAACTACATGTGTAACAGTTCCTG-CATGGGCGGCA TGAACCGGAGGCCCATCCTCACCATCATCACACTG-GAAGACTCCAGTGGTAATCTA CTGGGACG-GAACAGCTTGAGGTGCGTGTTGTGCCTGTCCTGG-GAGAGACCGGCG CACAGAGGAAGAGAATCTCCGCAAGAAAGGG-GAGCCTCACCACGAGCTGCCCCCA GGGAGCACTAAGCGAGCACTGCC-CAACAACACCAGCTCCTCTCCCCAGCCAAAGAA GAAACCACTGGATGGAGAATATTTCACCCTTCA- GATCCGTGGGCGTGAGCGCTTCG AGATGTCCGAGAGCTGAATGAGGCCTTGGAACT- CAAGGATGCCCAGGCTGGGAAG GAGCCAGGGGG- GAGCAGGGCTCACTCCAGCCACCTGAAGTC- CAAAAAGGGTCAGT CTACCTCCCGCCATAAAAAACTCATGTTCAA- GACAGAAGGGCCTGACTCAGAC TTAGGTACCATGTTCCAGATCCCAGAGTTTGAGCC GAGTGAGCAGGAAGACTCCAGCTC TGCAGAGAGGGGCCTGGGCCCCAGCCCCGCAGGG GACGGGCCCTCAGGCTCCGGC AAGCAT- CATCGCCAGGCCCCAGGCCTCCTGTGGGACGCCA GTCACCAGCAGGAGCA GCCAACCAGCAGCAGC- CATCATGGAGGCGCTGGGGCTGTGGAGATCCG- GAGTC GCC ACAGCGCCTACCCCGCGGGGACG- GAGGACGACGAAGGGATGGGGAGGAGCCCAG CCCCTTCGGGGCCGCTCGCGCGCAGCGCCCCC- CAACCTCTGGGCAGCACAGCGCT ATGGCCGCGAGCTCCGGAGGAT- GAGTGACGAGTGTGGACTCCTTTAAGAAGGGA CTTCCTCGCCCGAAGAGCGCGGGCACAGCAACG CAGATGCGGCAAAGCTCCAGCTG GACGCGAGTCTCCAGTCCTGGTGGGATCG- GAACTGGGCAGGGGAAGCTCCGCCC CCTCCCAGTGA (SEQ ID NO:8). The bold sequence is the p53 sequence. The underlined sequence is a linker. The regular font is the mutated BAD. It would be routine for one with ordinary skill in the art to make a nucleic acid that encodes the peptides disclosed herein since codons for each of the amino acids that make up the peptides are known.

Also, disclosed are compositions including primers and probes, which are capable of interacting with the polynucleotide sequences disclosed herein. For example, disclosed are primers/probes capable of amplifying a nucleic acid capable of encoding one or more of the disclosed peptides. The disclosed primers can used to support DNA amplification reactions. Typically the primers will be capable of being extended in a sequence specific manner. Extension of a primer in a sequence specific manner includes any methods wherein the sequence or composition of the nucleic acid molecule to which the primer is hybridized or otherwise associated directs or influences the composition or sequence of the product produced by the extension of the primer. Extension of the primer in a sequence specific manner therefore includes, but is not limited to, PCR, DNA sequencing, DNA extension, DNA polymerization, RNA transcription, or reverse transcription. Techniques and conditions that amplify the primer in a sequence specific manner are preferred. In certain embodiments the primers are used for the DNA amplification reactions, such as PCR or direct sequencing. It is understood that in certain embodiments the primers can also be extended using non-enzymatic techniques, where for example, the nucleotides or oligonucleotides used to extend the primer are modified such that they will chemically react to extend the primer in a sequence specific manner. Typically the disclosed primers hybridize with the polynucleotide sequences disclosed herein or region of the polynucleotide sequences disclosed herein or they hybridize with the complement of the polynucleotide sequences disclosed herein or complement of a region of the polynucleotide sequences disclosed herein.

The size of the primers or probes for interaction with the polynucleotide sequences disclosed herein in certain embodiments can be any size that supports the desired enzymatic manipulation of the primer, such as DNA amplification or the simple hybridization of the probe or primer. A typical primer or probe would be at least 6, 7, 8, 9, 10, 20, 30, 40, 50, 60, 70, 80, 90, 100, 125, 150, 175, 200, 225, 250, 275, 300, 325, 350, 375, 400, 425, 450, 475, 500, 550, 600, 650, 700, 750, 800, 850, 900, 950, 1000, 1250, 1500, 1750, 2000, 2250, 2500, 2750, 3000, 3500, or 4000 nucleotides long or any length in between.

Also disclosed are functional nucleic acids that can interact with the disclosed polynucleotides. Functional nucleic acids are nucleic acid molecules that have a specific function, such as binding a target molecule or catalyzing a specific reaction. Functional nucleic acid molecules can be divided into the following categories, which are not meant to be limiting. For example, functional nucleic acids include antisense molecules, aptamers, ribozymes, triplex forming molecules, and external guide sequences. The functional nucleic acid molecules can act as affectors, inhibitors, modulators, and stimulators of a specific activity possessed by a target molecule, or the functional nucleic acid molecules can possess a de novo activity independent of any other molecules.

Functional nucleic acid molecules can interact with any macromolecule, such as DNA, RNA, polypeptides, or carbohydrate chains. Thus, functional nucleic acids can interact with the mRNA of polynucleotide sequences disclosed herein or the genomic DNA of the polynucleotide sequences disclosed herein or they can interact with the polypeptide encoded by the polynucleotide sequences disclosed herein. Often functional nucleic acids are designed to interact with other nucleic acids based on sequence homology between the target molecule and the functional nucleic acid molecule. In other situations, the specific recognition between the functional nucleic acid molecule and the target molecule is not based on sequence homology between the functional nucleic acid molecule and the target molecule, but rather is based on the formation of tertiary structure that allows specific recognition to take place.

Optionally, isolated peptides or isolated nucleotides can also be purified, e.g., are at least about 90% pure, more preferably at least about 95% pure and most preferably at least about 99% pure.

By "isolated peptide" or "purified peptide" is meant a peptide (or a fragment thereof) that is substantially free from the materials with which the peptide is normally associated in nature. The peptides of the invention, or fragments thereof, can be obtained, for example, by extraction from a natural source (for example, a mammalian cell), by expression of a recombinant nucleic acid encoding the polypeptide (for example, in a cell or in a cell-free translation system), or by chemically synthesizing the polypeptide. In addition, polypeptide fragments may be obtained by any of these methods, or by cleaving full length polypeptides.

By "isolated nucleic acid" or "purified nucleic acid" is meant DNA that is free of the genes that, in the naturally-occurring genome of the organism from which the DNA of the invention is derived, flank the gene. The term therefore includes, for example, a recombinant DNA which is incorporated into a vector, such as an autonomously replicating plasmid or virus; or incorporated into the genomic DNA of a prokaryote or eukaryote (e.g., a transgene); or which exists as a separate molecule (for example, a cDNA or a genomic or cDNA fragment produced by PCR, restriction endonuclease digestion, or chemical or in vitro synthesis). It also includes a recombinant DNA which is part of a hybrid gene encoding additional polypeptide sequence. The term "isolated nucleic acid" also refers to RNA, e.g., an mRNA molecule that is encoded by an isolated DNA molecule, or that is chemically synthesized, or that is separated or substantially free from at least some cellular components, for example, other types of RNA molecules or polypeptide molecules.

It is understood that one way to define any known variants and derivatives or those that might arise, of the disclosed genes and proteins herein is through defining the variants and derivatives in terms of homology to specific known sequences. Specifically disclosed are variants of the genes and proteins herein disclosed which have at least, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent homology to the stated sequence. Those of skill in the art readily understand how to determine the homology of two proteins or nucleic acids, such as genes. For example, the homology can be calculated after aligning the two sequences so that the homology is at its highest level.

Another way of calculating homology can be performed by published algorithms. Optimal alignment of sequences for comparison may be conducted by the local homology algorithm of Smith and Waterman Adv. Appl. Math. 2: 482 (1981), by the homology alignment algorithm of Needleman and Wunsch, J. MoL Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of homology can be obtained for nucleic acids by for example the algorithms disclosed in Zuker, M. Science 244:48-52, 1989, Jaeger et al. Proc. Natl. Acad. Sci. USA 86:7706-7710, 1989, Jaeger et al. Methods Enzymol. 183:281-306, 1989 which are herein incorporated by reference for at least material related to nucleic acid alignment.

For example, as used herein, a sequence recited as having a particular percent homology to another sequence refers to sequences that have the recited homology as calculated by any one or more of the calculation methods described above. For example, a first sequence has 80 percent homology, as defined herein, to a second sequence if the first sequence is calculated to have 80 percent homology to the second sequence using the Zuker calculation method even if the first sequence does not have 80 percent homology to the second sequence as calculated by any of the other calculation methods. As another example, a first sequence has 80 percent homology, as defined herein, to a second sequence if the first sequence is calculated to have 80 percent homology to the second sequence using both the Zuker calculation method and the Pearson and Lipman calculation method even if the first sequence does not have 80 percent homology to the second sequence as calculated by the Smith and Waterman calculation method, the Needleman and Wunsch calculation method, the Jaeger calculation methods, or any of the other calculation methods. As yet another example, a first sequence has 80 percent homology, as defined herein, to a second sequence if the first sequence is calculated to have 80 percent homology to the second sequence using each of calculation methods (although, in practice, the different calculation methods will often result in different calculated homology percentages).

1. Compositions Comprising Nucleic Acids

Also disclosed are compositions comprising the nucleic acid sequences described herein. For example, disclosed are compositions comprising a nucleic acid sequence wherein the nucleic acid sequence comprises a sequence capable of encoding a p53 peptide operably linked to a nucleic acid sequence capable of encoding a BH3-only protein.

Disclosed are compositions comprising a nucleic acid sequence wherein the nucleic acid sequence comprises a sequence capable of encoding a p53 peptide operably linked to a nucleic acid sequence capable of encoding a BH3-only protein wherein the BH3-only protein is BAD, BID, BIM, NOXA. In some aspects, the BH3-only protein can be BAD. In some aspects, the nucleic acid sequence capable of encoding BAD as the BH3-only protein can comprise the nucleic acid sequence of SEQ ID NO:5. In some aspects, the nucleic acid sequence of BAD consists of SEQ ID NO:5.

Disclosed are compositions comprising a nucleic acid sequence wherein the nucleic acid sequence comprises a sequence capable of encoding a p53 peptide operably linked to a nucleic acid sequence capable of encoding a BH3-only protein, wherein the BH3-only protein is BAD, wherein the nucleic acid sequence comprises the sequence of SEQ ID NO:6.

Disclosed are compositions comprising a nucleic acid sequence wherein the nucleic acid sequence comprises a sequence capable of encoding a p53 peptide operably linked to a nucleic acid sequence capable of encoding a BH3-only protein, wherein the BH3-only protein is a mutated BAD, wherein the nucleic acid sequence comprises the sequence of SEQ ID NO:7.

Disclosed are compositions comprising a nucleic acid sequence wherein the nucleic acid sequence comprises a sequence capable of encoding a p53 peptide operably linked to a nucleic acid sequence capable of encoding a BH3-only protein, wherein the BH3-only protein is a mutated BAD, wherein the nucleic acid sequence comprises the sequence of SEQ ID NO:8.

D. Vectors

Also disclosed are vectors comprising the nucleic acid sequences disclosed herein. Disclosed are vectors comprising a nucleic acid sequence, wherein the nucleic acid sequence is capable of encoding one or more of the peptides disclosed herein. For example, disclosed are vectors comprising a nucleic acid sequence, wherein the nucleic acid sequence comprises a sequence capable of encoding a p53 peptide operably linked to a nucleic acid sequence capable of encoding a BH3-only protein.

In some aspects, the vector can be a viral vector. For example, the viral vector can be, but is not limited to, an adenoviral vector, lentiviral vector or adeno-associated virus vector.

In some aspects, the viral vector can be an adenoviral vector.

Also disclosed are non-viral vectors comprising any of the disclosed nucleic acid sequences.

In some aspects, the disclosed vectors further comprise a promoter. In some aspects, the promoter can be operably linked to the nucleic acid sequence capable of encoding one or more of the peptides disclosed herein. In some aspects, the promoter can be a cancer-specific promoter. For example, the cancer-specific promoter can be a hTERT promoter or ran promoter.

In some aspects, the vector can be coated with poly (cystaminebisacryl-amide-diaminohexane)-polyethylene glycol linked to Arg-Gly-Asp [CD-PEG-RGD].

1. Compositions Comprising Vectors

Also disclosed are compositions comprising the vectors described herein. For example, disclosed are compositions comprising a nucleic acid sequence, wherein the nucleic acid sequence is capable of encoding one or more of the peptides disclosed herein. For example, disclosed are compositions comprising vectors comprising a nucleic acid sequence, wherein the nucleic acid sequence comprises a sequence capable of encoding a p53 peptide operably linked to a nucleic acid sequence capable of encoding a BH3-only protein.

i. Viral and Non-Viral Vectors

There are a number of compositions and methods which can be used to deliver nucleic acids to cells, either in vitro or in vivo. These methods and compositions can largely be broken down into two classes: viral based delivery systems and non-viral based delivery systems. For example, the nucleic acids can be delivered through a number of direct delivery systems such as, electroporation, lipofection, calcium phosphate precipitation, plasmids, viral vectors, viral nucleic acids, phage nucleic acids, phages, cosmids, or via transfer of genetic material in cells or carriers such as cationic liposomes. Appropriate means for transfection, including viral vectors, chemical transfectants, or physicomechanical methods such as electroporation and direct diffusion of DNA, are described by, for example, Wolff, J. A., et al., Science, 247, 1465-1468, (1990); and Wolff, J. A. Nature, 352, 815-818, (1991). Such methods are well known in the art and readily adaptable for use with the compositions and methods described herein. In certain cases, the methods will be modified to specifically function with large DNA molecules. Further, these methods can be used to target certain diseases and cell populations by using the targeting characteristics of the carrier.

Expression vectors can be any nucleotide construction used to deliver genes or gene fragments into cells (e.g., a plasmid), or as part of a general strategy to deliver genes or gene fragments, e.g., as part of recombinant retrovirus or adenovirus (Ram et al. Cancer Res. 53:83-88, (1993)). For example, disclosed herein are expression vectors comprising a nucleic acid sequence capable of encoding one or more of the disclosed peptides operably linked to a control element.

The "control elements" present in an expression vector are those non-translated regions of the vector—enhancers, promoters, 5' and 3' untranslated regions-which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the pBLUESCRIPT phagemid (Stratagene, La Jolla, Calif.) or pSPORT1 plasmid (Gibco BRL, Gaithersburg, Md.) and the like may be used. In mammalian cell systems, promoters from mammalian genes or from mammalian viruses are generally preferred. If it is necessary to generate a cell line that contains multiple copies of the sequence encoding a polypeptide, vectors based on SV40 or EBV may be advantageously used with an appropriate selectable marker.

Preferred promoters controlling transcription from vectors in mammalian host cells may be obtained from various sources, for example, the genomes of viruses such as polyoma, Simian Virus 40 (SV40), adenovirus, retroviruses, hepatitis-B virus and most preferably cytomegalovirus, or from heterologous mammalian promoters (e.g., beta actin promoter). The early and late promoters of the SV40 virus are conveniently obtained as an SV40 restriction fragment, which also contains the SV40 viral origin of replication (Fiers et al., Nature, 273: 113 (1978)). The immediate early promoter of the human cytomegalovirus is conveniently obtained as a HindIII E restriction fragment (Greenway, P. J. et al., Gene 18: 355-360 (1982)). Additionally, promoters from the host cell or related species can also be used.

Enhancer generally refers to a sequence of DNA that functions at no fixed distance from the transcription start site and can be either 5' (Laimins, L. et al., Proc. Natl. Acad. Sci. 78: 993 (1981)) or 3' (Lusky, M. L., et al., Mol. Cell Bio. 3: 1108 (1983)) to the transcription unit. Furthermore, enhancers can be within an intron (Banerji, J. L. et al., Cell 33: 729 (1983)) as well as within the coding sequence itself (Osbome, T. F., et al., Mol. Cell Bio. 4: 1293 (1984)). They are usually between 10 and 300 bp in length, and they function in cis. Enhancers function to increase transcription from nearby promoters. Enhancers also often contain response elements that mediate the regulation of transcription. Promoters can also contain response elements that mediate the regulation of transcription. Enhancers often determine the regulation of expression of a gene. While many enhancer sequences are now known from mammalian genes (globin, elastase, albumin, a-fetoprotein and insulin), typically one will use an enhancer from a eukaryotic cell virus for general expression. Preferred examples are the SV40 enhancer on the late side of the replication origin (bp 100-270), the cytomegalovirus early promoter enhancer, the polyoma enhancer on the late side of the replication origin, and adenovirus enhancers.

The promoter or enhancer may be specifically activated either by light or specific chemical events which trigger their function. Systems can be regulated by reagents such as tetracycline and dexamethasone. There are also ways to enhance viral vector gene expression by exposure to irradiation, such as gamma irradiation, or alkylating chemotherapy drugs.

Optionally, the promoter or enhancer region can act as a constitutive promoter or enhancer to maximize expression of the polynucleotides of the invention. In certain constructs the promoter or enhancer region be active in all eukaryotic cell types, even if it is only expressed in a particular type of cell at a particular time. A preferred promoter of this type is the CMV promoter (650 bases). Other preferred promoters are SV40 promoters, cytomegalovirus (full length promoter), and retroviral vector LTR.

Expression vectors used in eukaryotic host cells (yeast, fungi, insect, plant, animal, human or nucleated cells) may also contain sequences necessary for the termination of transcription which may affect mRNA expression. These regions are transcribed as polyadenylated segments in the untranslated portion of the mRNA encoding tissue factor protein. The 3' untranslated regions also include transcription termination sites. It is preferred that the transcription unit also contains a polyadenylation region. One benefit of this region is that it increases the likelihood that the transcribed unit will be processed and transported like mRNA. The identification and use of polyadenylation signals in expression constructs is well established. It is preferred that homologous polyadenylation signals be used in the transgene constructs. In certain transcription units, the polyadenylation region is derived from the SV40 early polyadenylation signal and consists of about 400 bases.

The expression vectors can include a nucleic acid sequence encoding a marker product. This marker product is used to determine if the gene has been delivered to the cell and once delivered is being expressed. Preferred marker genes are the E. coli lacZ gene, which encodes B-galactosidase, and the gene encoding the green fluorescent protein.

In some embodiments the marker may be a selectable marker. Examples of suitable selectable markers for mammalian cells are dihydrofolate reductase (DHFR), thymidine kinase, neomycin, neomycin analog G418, hydromycin, and puromycin. When such selectable markers are successfully transferred into a mammalian host cell, the transformed mammalian host cell can survive if placed under selective pressure. There are two widely used distinct categories of selective regimes. The first category is based on a cell's metabolism and the use of a mutant cell line which lacks the ability to grow independent of a supplemented media. Two examples are CHO DHFR-cells and mouse LTK-cells. These cells lack the ability to grow without the addition of such nutrients as thymidine or hypoxanthine. Because these cells lack certain genes necessary for a complete nucleotide synthesis pathway, they cannot survive unless the missing nucleotides are provided in a supplemented media. An alternative to supplementing the media is to introduce an intact DHFR or TK gene into cells lacking the respective genes, thus altering their growth requirements. Individual cells which were not transformed with the DHFR or TK gene will not be capable of survival in non-supplemented media.

The second category is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin, (Southern P. and Berg, P., J. Molec. Appl. Genet. 1: 327 (1982)), mycophenolic acid, (Mulligan, R. C. and Berg, P. Science 209: 1422 (1980)) or hygromycin, (Sugden, B. et al., Mol. Cell. Biol. 5: 410-413 (1985)). The three examples employ bacterial genes under eukaryotic control to convey resistance to the appropriate drug G418 or neomycin (geneticin), xgpt (mycophenolic acid) or hygromycin, respectively. Others include the neomycin analog G418 and puramycin.

As used herein, plasmid or viral vectors are agents that transport the disclosed nucleic acids, such as a nucleic acid sequence capable of encoding one or more of the disclosed peptides into the cell without degradation and include a promoter yielding expression of the gene in the cells into which it is delivered. In some embodiments the nucleic acid sequences disclosed herein are derived from either a virus or a retrovirus. Viral vectors are, for example, Adenovirus, Adeno-associated virus, Herpes virus, Vaccinia virus, Polio virus, AIDS virus, neuronal trophic virus, Sindbis and other RNA viruses, including these viruses with the HIV backbone. Also preferred are any viral families which share the properties of these viruses which make them suitable for use as vectors. Retroviruses include Murine Maloney Leukemia virus, MMLV, and retroviruses that express the desirable properties of MMLV as a vector. Retroviral vectors are able to carry a larger genetic payload, i.e., a transgene or marker gene, than other viral vectors, and for this reason are a commonly used vector. However, they are not as useful in non-proliferating cells. Adenovirus vectors are relatively stable and easy to work with, have high titers, and can be delivered in aerosol formulation, and can transfect non-dividing cells. Pox viral vectors are large and have several sites for inserting genes, they are thermostable and can be stored at room temperature. A preferred embodiment is a viral vector which has been engineered so as to suppress the immune response of the host organism, elicited by the viral antigens. Preferred vectors of this type will carry coding regions for Interleukin 8 or 10.

Viral vectors can have higher transaction abilities (i.e., ability to introduce genes) than chemical or physical methods of introducing genes into cells. Typically, viral vectors contain, nonstructural early genes, structural late genes, an RNA polymerase III transcript, inverted terminal repeats necessary for replication and encapsidation, and promoters to control the transcription and replication of the viral genome. When engineered as vectors, viruses typically have one or more of the early genes removed and a gene or gene/promoter cassette is inserted into the viral genome in place of the removed viral DNA. Constructs of this type can carry up to about 8 kb of foreign genetic material. The necessary functions of the removed early genes are typically supplied by cell lines which have been engineered to express the gene products of the early genes in trans.

Retroviral vectors, in general, are described by Verma, I. M., Retroviral vectors for gene transfer. In Microbiology, Amer. Soc. for Microbiology, pp. 229-232, Washington, (1985), which is hereby incorporated by reference in its entirety. Examples of methods for using retroviral vectors for gene therapy are described in U.S. Pat. Nos. 4,868,116 and 4,980,286; PCT applications WO 90/02806 and WO 89/07136; and Mulligan, (Science 260:926-932 (1993)); the teachings of which are incorporated herein by reference in their entirety for their teaching of methods for using retroviral vectors for gene therapy.

A retrovirus is essentially a package which has packed into it nucleic acid cargo. The nucleic acid cargo carries with it a packaging signal, which ensures that the replicated daughter molecules will be efficiently packaged within the package coat. In addition to the package signal, there are a number of molecules which are needed in cis, for the replication, and packaging of the replicated virus. Typically a retroviral genome contains the gag, pol, and env genes which are involved in the making of the protein coat. It is the gag, pol, and env genes which are typically replaced by the foreign DNA that it is to be transferred to the target cell. Retrovirus vectors typically contain a packaging signal for incorporation into the package coat, a sequence which signals the start of the gag transcription unit, elements necessary for reverse transcription, including a primer binding site to bind the tRNA primer of reverse transcription, terminal repeat sequences that guide the switch of RNA strands during DNA synthesis, a purine rich sequence 5' to the 3' LTR that serves as the priming site for the synthesis of the second strand of DNA synthesis, and specific sequences near the ends of the LTRs that enable the insertion of the DNA state of the retrovirus to insert into the host genome. This amount of nucleic acid is sufficient for the delivery of a one to many genes depending on the size of each transcript. It is preferable to include either positive or negative selectable markers along with other genes in the insert.

Since the replication machinery and packaging proteins in most retroviral vectors have been removed (gag, pol, and env), the vectors are typically generated by placing them into a packaging cell line. A packaging cell line is a cell line which has been transfected or transformed with a retrovirus that contains the replication and packaging machinery but lacks any packaging signal. When the vector carrying the DNA of choice is transfected into these cell lines, the vector containing the gene of interest is replicated and packaged into new retroviral particles, by the machinery provided in cis by the helper cell. The genomes for the machinery are not packaged because they lack the necessary signals.

The construction of replication-defective adenoviruses has been described (Berkner et al., J. Virology 61:1213-1220 (1987); Massie et al., Mol. Cell. Biol. 6:2872-2883 (1986); Haj-Ahmad et al., J. Virology 57:267-274 (1986); Davidson et al., J. Virology 61:1226-1239 (1987); Zhang "Generation and identification of recombinant adenovirus by liposome-mediated transfection and PCR analysis" BioTechniques 15:868-872 (1993)). The benefit of the use of these viruses as vectors is that they are limited in the extent to which they can spread to other cell types, since they can replicate within an initial infected cell but are unable to form new infectious viral particles. Recombinant adenoviruses have been shown to achieve high efficiency gene transfer after direct, in vivo delivery to airway epithelium, hepatocytes, vascular endothelium, CNS parenchyma and a number of other tissue sites (Morsy, J. Clin. Invest. 92:1580-1586 (1993); Kirshenbaum, J. Clin. Invest. 92:381-387 (1993); Roessler, J. Clin. Invest. 92:1085-1092 (1993); Moullier, Nature Genetics 4:154-159 (1993); La Salle, Science 259:988-990 (1993); Gomez-Foix, J. Biol. Chem. 267:25129-25134 (1992); Rich, Human Gene Therapy 4:461-476 (1993); Zabner, Nature Genetics 6:75-83 (1994); Guzman, Circulation Research 73:1201-1207 (1993); Bout, Human Gene Therapy 5:3-10 (1994); Zabner, Cell 75:207-216 (1993); Caillaud, Eur. J. Neuroscience 5:1287-1291 (1993); and Ragot, J. Gen. Virology 74:501-507 (1993)) the teachings of which are incorporated herein by reference in their entirety for their teaching of methods for using retroviral vectors for gene therapy. Recombinant adenoviruses achieve gene transduction by binding to specific cell surface receptors, after which the virus is internalized by receptor-mediated endocytosis, in the same manner as wild type or replication-defective adenovirus (Chardonnet and Dales, Virology 40:462-477 (1970); Brown and Burlingham, J. Virology 12:386-396 (1973); Svensson and Persson, J. Virology 55:442-449 (1985); Seth, et al., J. Virol. 51:650-655 (1984); Seth, et al., Mol. Cell. Biol., 4:1528-1533 (1984); Varga et al., J. Virology 65:6061-6070 (1991); Wickham et al., Cell 73:309-319 (1993)).

A viral vector can be one based on an adenovirus which has had the E1 gene removed and these virons are generated in a cell line such as the human 293 cell line. Optionally, both the E1 and E3 genes are removed from the adenovirus genome.

Another type of viral vector that can be used to introduce the polynucleotides of the invention into a cell is based on an adeno-associated virus (AAV). This defective parvovirus is a preferred vector because it can infect many cell types and is nonpathogenic to humans. AAV type vectors can transport about 4 to 5 kb and wild type AAV is known to stably insert into chromosome 19. Vectors which contain this site specific integration property are preferred. An especially preferred embodiment of this type of vector is the P4.1 C vector produced by Avigen, San Francisco, Calif., which can contain the herpes simplex virus thymidine kinase gene, HSV-tk, or a marker gene, such as the gene encoding the green fluorescent protein, GFP.

In another type of AAV virus, the AAV contains a pair of inverted terminal repeats (ITRs) which flank at least one cassette containing a promoter which directs cell-specific expression operably linked to a heterologous gene. Heterologous in this context refers to any nucleotide sequence or gene which is not native to the AAV or B19 parvovirus. Typically the AAV and B19 coding regions have been deleted, resulting in a safe, noncytotoxic vector. The AAV ITRs, or modifications thereof, confer infectivity and site-specific integration, but not cytotoxicity, and the promoter directs cell-specific expression. U.S. Pat. No. 6,261,834 is herein incorporated by reference in its entirety for material related to the AAV vector.

The inserted genes in viral and retroviral vectors usually contain promoters, or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and may contain upstream elements and response elements.

Other useful systems include, for example, replicating and host-restricted non-replicating vaccinia virus vectors. In addition, the disclosed nucleic acid sequences can be delivered to a target cell in a non-nucleic acid based system. For example, the disclosed polynucleotides can be delivered through electroporation, or through lipofection, or through calcium phosphate precipitation. The delivery mechanism chosen will depend in part on the type of cell targeted and whether the delivery is occurring for example in vivo or in vitro.

Thus, the compositions can comprise, in addition to the disclosed expression vectors, lipids such as liposomes, such as cationic liposomes (e.g., DOTMA, DOPE, DC-cholesterol) or anionic liposomes. Liposomes can further comprise proteins to facilitate targeting a particular cell, if desired. Administration of a composition comprising a peptide and a cationic liposome can be administered to the blood, to a target organ, or inhaled into the respiratory tract to target cells of the respiratory tract. For example, a composition comprising a peptide or nucleic acid sequence described herein and a cationic liposome can be administered to a subjects lung cells. Regarding liposomes, see, e.g., Brigham et al. Am. J. Resp. Cell. Mol. Biol. 1:95-100 (1989); Felgner et al. Proc. Natl. Acad. Sci USA 84:7413-7417 (1987); U.S. Pat. No. 4,897,355. Furthermore, the compound can be administered as a component of a microcapsule that can be targeted to specific cell types, such as macrophages, or where the diffusion of the compound or delivery of the compound from the microcapsule is designed for a specific rate or dosage.

E. Delivery of Compositions

In the methods described herein, delivery of the compositions to cells can be via a variety of mechanisms. As defined above, disclosed herein are compositions comprising any one or more of the peptides, nucleic acids, and/or vectors described herein can be used to produce a composition which can also include a carrier such as a pharmaceutically acceptable carrier. For example, disclosed are pharmaceutical compositions, comprising the peptides disclosed herein, and a pharmaceutically acceptable carrier.

For example, the compositions described herein can comprise a pharmaceutically acceptable carrier. By "pharmaceutically acceptable" is meant a material or carrier that would be selected to minimize any degradation of the active ingredient and to minimize any adverse side effects in the subject, as would be well known to one of skill in the art. Examples of carriers include dimyristoylphosphatidyl (DMPC), phosphate buffered saline or a multivesicular liposome. For example, PG:PC:Cholesterol:peptide or PC:peptide can be used as carriers in this invention. Other suitable pharmaceutically acceptable carriers and their formulations are described in Remington: The Science and Practice of Pharmacy (19th ed.) ed. A. R. Gennaro, Mack Publishing Company, Easton, Pa. 1995. Typically, an appropriate amount of pharmaceutically-acceptable salt is used in the formulation to render the formulation isotonic. Other examples of the pharmaceutically-acceptable carrier include, but are not limited to, saline, Ringer's solution and dextrose solution. The pH of the solution can be from about 5 to about 8, or from about 7 to about 7.5. Further carriers include sustained release preparations such as semi-permeable matrices of solid hydrophobic polymers containing the composition, which matrices are in the form of shaped articles, e.g., films, stents (which are implanted in vessels during an angioplasty procedure), liposomes or microparticles. It will be apparent to those persons skilled in the art that certain carriers may be more preferable depending upon, for instance, the route of administration and concentration of composition being administered. These most typically would be standard carriers for administration of drugs to humans, including solutions such as sterile water, saline, and buffered solutions at physiological pH.

Pharmaceutical compositions can also include carriers, thickeners, diluents, buffers, preservatives and the like, as long as the intended activity of the polypeptide, peptide, nucleic acid, vector of the invention is not compromised. Pharmaceutical compositions may also include one or more active ingredients (in addition to the composition of the invention) such as antimicrobial agents, anti-inflammatory agents, anesthetics, and the like. The pharmaceutical composition may be administered in a number of ways depending on whether local or systemic treatment is desired, and on the area to be treated.

Preparations of parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Formulations for optical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids, or binders may be desirable. Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mon-, di-, trialkyl and aryl amines and substituted ethanolamines.

F. Methods

1. Method of Inducing Apoptosis

Disclosed are methods of inducing apoptosis comprising administering one or more of the peptides or nucleic acid sequences disclosed herein. In some aspects, the peptide induces apoptosis through the Bak or Bax pathway.

Disclosed are methods of inducing apoptosis comprising administering one or more of the compositions disclosed herein.

2. Method of Targeting a Peptide

Disclosed are methods of targeting a peptide to mitochondria comprising introducing a peptide to a cell, wherein the peptide is one or more of the peptides disclosed herein. In some aspects, the cell is in culture. In some aspects, the cell is part of a subject.

Disclosed are methods of targeting a peptide to mitochondria comprising introducing any of the disclosed herein nucleic acid sequences capable of encoding one or more of the disclosed peptides.

Disclosed are methods of targeting a composition to mitochondria comprising introducing a composition to a subject, wherein the composition comprises a peptide, nucleic acid sequence or vector disclosed herein.

3. Method of Inducing Homo-Oligomerization of Bak or Bax

Disclosed are methods of inducing homo-oligomerization of Bak or Bax comprising administering a peptide or a nucleic acid sequence disclosed herein.

Disclosed are methods of inducing homo-oligomerization of Bak or Bax comprising administering a composition disclosed herein.

4. Method of Treating a Hyperproliferative Disorder

Disclosed are methods of treating a hyperproliferative disorder in a patient comprising administering to the patient any one of the peptides or nucleic acid sequences disclosed herein.

In some instances, the hyperproliferative disorder is cancer. In some aspects, the cancer can be, but is not limited to, breast cancer or ovarian cancer.

Hyperproliferative disorders include cancer and non-cancer hyperproliferative disorders. Cancers include, but are not limited to brain, lung, squamous cell, bladder, gastric, pancreatic, breast, head, neck, renal, kidney, ovarian, prostate, colorectal, endometrial, esophageal, testicular, gynecological and thyroid cancer. Non-cancer hyperproliferative disorders include, but are not limited to, benign hyperplasia of the skin (e.g., psoriasis), restenosis, or prostate (e.g., benign prostatic hypertrophy (BPH)), age-related macular degeneration, Crohn's disease, cirrhosis, chronic inflammatory-related disorders, proliferative diabetic retinopathy, proliferative vitreoretinopathy, retinopathy of prematurity, granulomatosis, immune hyperproliferation associated with organ or tissue transplantation, an immunoproliferative disease or disorder, e.g., inflammatory bowel disease, rheumatoid arthritis, systemic lupus erythematosus (SLE), vascular hyperproliferation secondary to retinal hypoxia, or vasculitis.

Disclosed are methods of treating a hyperproliferative disorder in a patient comprising administering to the patient any one of the peptides or nucleic acid sequences disclosed herein, further comprising co-administering an anti-cancer agent. For example, the anti-cancer agent can be, but is not limited to, paclitaxel or carboplatin. Anti-cancer agents are compounds useful in the treatment of cancer. Examples of anti-cancer agents include alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CBl-TMl); eleutherobin; pancratistatin; a sarcodictyin; spongistatin; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosf amide, uracil mustard; nitrosureas such as carmustine, chlorozotocin, fotemustine, lomustine, nimustine, and ranimnustine; antibiotics such as the enediyne antibiotics (e. g., calicheamicin, especially calicheamicin gammall and calicheamicin omegall (see, e.g., Agnew, Chem Intl. Ed. Engl., 33: 183-186 (1994)); dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including ADRIAMYCIN®, morpholino-doxorubicin, cyanomorpholino-doxorubicin, 2-pyrrolino-doxorubicin, doxorubicin HCl liposome injection (DOXIL®) and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate, gemcitabine (GEMZAR®), tegafur (UFTORAL®), capecitabine (XELODA®), an epothilone, and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfomithine; elliptinium acetate; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethane; vindesine (ELDISEME®, FILDESIN®); dacarbazine; mannomustine; mitobronitol; mitolactol; pipobroman; gacytosine; arabinoside ("Ara-C"); thiotepa; taxoids, e.g., paclitaxel (TAXOL®), albumin-engineered nanoparticle formulation of paclitaxel (ABRAXANE™), and doxetaxel (TAXOTERE®); chloranbucil; 6-thioguanine; mercaptopurine; methotrexate; platinum analogs such as cisplatin and carboplatin; vinblastine (VELB AN®); platinum; etoposide (VP-16); ifosf amide; mitoxantrone; vincristine (ONCOVIN®); oxaliplatin; leucovovin; vinorelbine (NAVELBINE®); novantrone; edatrexate; daunomycin; aminopterin; ibandronate; topoisomerase inhibitor RFS 2000; difluorometlhylornithine (DMFO); retinoids such as retinoic acid; pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovovin.

In some aspects, the nucleic acid sequence can be administered to the patient using a viral vector. For example, the viral vector can be, but is not limited to, an adenoviral vector, lentiviral vector or an adeno-associated viral vector.

Disclosed are methods of treating a hyperproliferative disorder in a patient comprising administering to the patient any one of the compositions disclosed herein.

G. Cells

Disclosed are cells comprising the peptide, the nucleic acid, or the vector disclosed herein.

Also disclosed herein are host cells transformed or transfected with an expression vector comprising the nucleic acid sequences described elsewhere herein. Also disclosed are host cells comprising the expression vectors described herein. For example, disclosed is a host cell comprising an expression vector comprising the nucleic acid sequences described elsewhere herein, operably linked to a control element. Host cells can be eukaryotic or prokaryotic cells. For example, a host cell can be a mammalian cell. Also disclosed are recombinant cells comprising the disclosed nucleic acid sequences or peptides. Further disclosed are recombinant cells producing the disclosed peptides.

Disclosed are recombinant cells comprising one or more of the nucleic acid sequences, peptides or vectors disclosed herein.

Disclosed are recombinant cells comprising one or more of the nucleic acid sequences capable of producing any of the peptides disclosed herein.

For example, disclosed are T47D, H1373, SKOV-3 and HeLa cells comprising one or more of the nucleic acid sequences disclosed herein. Further disclosed are T47D, H1373, SKOV-3 and HeLa cells comprising one or more of the nucleic acid sequences capable of producing any of the peptides disclosed herein.

H. Transgenics

Disclosed are transgenic, non-human subjects comprising the nucleic acid sequences, peptides or vectors disclosed herein which are capable of encoding the peptides disclosed herein. For example, disclosed are transgenic, non-human subjects comprising a nucleic acid sequence, wherein the nucleic acid sequence is capable of encoding a p53 peptide operably linked to a nucleic acid sequence capable of encoding a BH3-only protein.

I. Kits

The materials described above as well as other materials can be packaged together in any suitable combination as a kit useful for performing, or aiding in the performance of, the disclosed method. It is useful if the kit components in a given kit are designed and adapted for use together in the disclosed method. For example disclosed are kits for producing vectors, the kit comprising any of the disclosed nucleic acid sequences. The kits also can contain a viral vector.

EXAMPLES

1. Background and Summary

Previous work has shown that mitochondrially targeted p53 can kill cancer cells in vitro; described herein is potent amplification of p53's killing effect at the mitochondria can be achieved by fusing it with BH3 only proteins that are apoptotic mitochondrial proteins which can directly bind to and inactivate anti-apoptotic proteins. A gene therapy construct that expresses p53 fused to a BH3 protein (called p53-BH3; MTS is an embedded mitochondrial targeting signal in the BH3 protein) would have multiple unique mechanisms of action that can both activate pro-apoptotic proteins and inactivate anti-apoptotic proteins at the mitochondria. p53-BH3 can bypass resistance mechanisms mentioned above due to its direct and multiple mechanisms of apoptosis, and would not be subject to efflux pumps as it is not a small molecule drug. A fusion ensures that both proteins are at the mitochondria at the same time, and can act together; data indicates robust killing of cancer cells with the p53-BH3 construct driven by a CMV promoter. To achieve cancer cell specificity, a cancer specific promoter based on hTERT or ran (RAS-related nuclear protein) can be used to drive production of p53-BH3 proteins only in cancer cells. A novel polymer-adenovirus gene delivery system (CD-PEG-RGD) can be used, conferring tumor specificity (via the CD and RGD moieties) and reduced immunogenicity of adenovirus (due to polymer "coating"). To test therapeutic efficacy, gene therapy can be injected intraperitoneally into a syngeneic orthotopic metastatic mouse ovarian cancer model, which closely mimics human disease progression. An ideal ovarian cancer therapy can be independent of HGSC genetic heterogeneity, overcome drug resistance, potently activate apoptosis, be cancer-specific, and be effectively delivered and expressed. Described herein are three studies: 1) Design and clone novel p53-BH3 gene therapy constructs (BH3 only proteins to be tested are Bad, tBid, Bims, and Noxa) with a cancer-specific promoter capable of mitochondrial localization and direct activation of intrinsic apoptosis in ovarian cancer cells. 2) Determine the apoptotic potential of p53-BH3 in ovarian cancer cell lines (human and mouse) with varying p53 status, and determine the mechanisms of apoptosis. 3) Deliver p53-BH3 using an advanced polymeric-adenovirus (Ad) hybrid delivery system (using modified Ad with CD-PEG-RGD polymer) first in vitro, then in vivo by intraperitoneal (IP) injection into a pre-clinical syngeneic orthotopic metastatic mouse ovarian cancer model.

2. Significance:

Ovarian Cancer and Lack of Effective Treatments:

Wild type (wt) p53 gene therapy was attempted in clinical trials for ovarian cancer in the late 1990's but was thought to have failed due to 1) multiple genetic aberrations (besides p53), 2) dominant negative inactivation of exogenous p53 by endogenous mutant p53 found in cancer cells, and 3) issues with the older versions of adenovirus for gene delivery (lack of tumor targeting and immunogenicity). More recently, for chemoresistant HGSC, whole-genome sequencing revealed gene breakage of tumor suppressors RB1, NF1, RAD51B, and PTEN, and various other mutations (such as CCNE1 amplification, BRCA1/2 mutations; MDR1 efflux pump overexpression). Clearly, the heterogeneity of ovarian cancer and its resistance mechanisms obfuscate clinicians' ability to effectively treat patients with this disease.

Scientific Premise.

Figure 2:
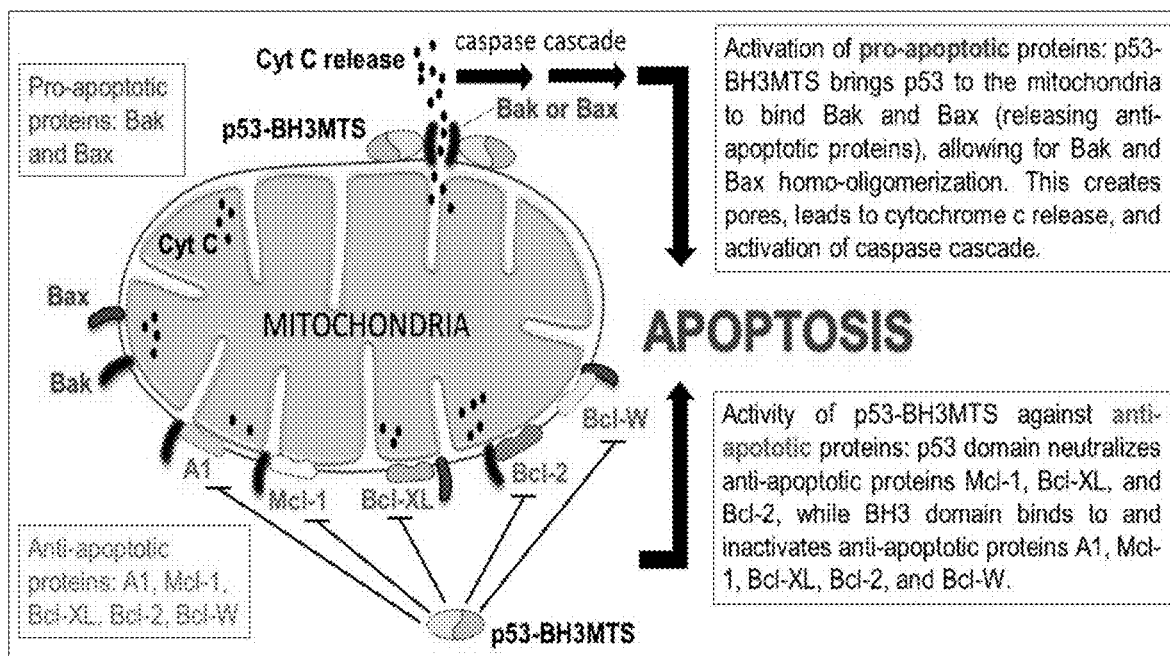
FIG. 2 is a schematic showing multiple mechanisms of action proposed for $p^{53}$-BH3: activates pro-apoptotic proteins and inactivates anti-apoptotic proteins, leading to apoptotic collapse.

Impact of p53-BH3 gene therapy: p53-BH3 are conceptually simple p53/BH3 only fusions that when expressed (FIG. 1), are designed to activate apoptotic proteins and inactivate anti-apoptotic proteins at the mitochondria. Nomenclature of p53-BH3 includes "MTS" which is embedded in BH3 proteins (FIG. 1). The premise is based on the apoptotic activity of mitochondrially directed p53, and the pro-apoptotic functions of BH3 proteins (Bad, Bid, Bim, or Noxa). A p53-BH3 fusion protein can trigger potent apoptosis, and can be a universal method capable of killing any cancer cell, regardless of its genetic heterogeneity. This represents a breakthrough concept in cancer therapy. Proposed mechanisms of action of a p53-BH3 construct stem from mitochondrial apoptotic mechanisms of action of p53 and the BH3 construct (FIG. 2).

Mitochondrial D53 Background and Significance:

p53 (or its DBD subdomain) with a mitochondrial targeting signal can induce apoptosis in a variety of cancer cell lines, regardless of p53 status (wt, mutant, or null). Mitochondrially targeted p53 for cancer therapy was proposed as a novel cancer therapy. If p53 is directed to the mitochondria with a mitochondrial targeting signal (MTS), p53 can bind to pro-apoptotic Bak and Bax, allowing for their homo-oligomerization, leading to mitochondrial outer membrane permeabilization (pore formation), cytochrome C release, and activation of the caspase cascade, which in turn lead to apoptosis (FIG. 2, top). p53 is also known to neutralize anti-apoptotic proteins Mcl-1, Bcl-XL, Bcl-2, and Bcl-W (FIG. 2, bottom) and can displace pro-apoptotic Bid from anti-apoptotic Bcl-XL. While p53-MTS mainly colocalizes to the mitochondria, a fraction is still found in the cytoplasm. Cytoplasmic p53 can bind Bcl-W or Bcl-XL, and release Bax or Bak, respectively, and suppress cancer cell invasion by reducing mitochondrial reactive oxygen species (ROS) levels, adding another anti-cancer mechanism.

BH3 Protein Background and Significance:

Pro- and anti-apoptotic Bcl-2 family members contain various Bcl-2 homology (BH) domains, named BH1-4. Pro-apoptotic factors Bim, Bad, Bid, Noxa, and Puma are so-called "BH3 only proteins," and are considered to be death effector molecules. The BH3 only proteins only contain the BH3 homology domain (and not BH1, 2, or 4). The different BH3 domains in these proteins provide the specificity for the interaction of these BH3-only proteins to their designated anti-apoptotic targets. Inhibition of anti-apoptotic Bcl-2 family members has been an area of active research. ABT-727 (poorly soluble) and ABT-263/navitoclax (Phase II clinical trial discontinued) are both small molecule inhibitors of Bcl-XL, Bcl-w, and Bcl-2. Both drugs exhibit dose-limiting thrombocytopenia due to inhibition of Bcl-XL, important for platelet function. ABT-199/venetoclax selectively inhibits Bcl-2, and is indicated for a subset of patients with CLL, but still with dose-limiting toxicities, including tumor lysis syndromes, grade IV neutropenia, and sudden death. GX-015-070/obatoclax is a selective Mcl-1 inhibitor, but was discontinued in Phase III clinical trials. Widespread use of these drugs as single agents for cancer treatment is greatly limited due to toxicities as well as acquired drug resistance. While BH3 proteins have been touted as "the key to successful cancer therapy", redundancy in the apoptotic machinery means that the blockade of a single anti-apoptotic protein may not be sufficient and in some cell lines there may be varying levels of a given anti- or pro-apoptotic protein. The end result is that the cell may be able to compensate to overcome therapeutic attempts at inducing apoptosis with a singly-targeted agent (such as a specific BH3 peptide mimetic or an inhibitor of an anti-apoptotic protein) by upregulation other anti-apoptotic proteins. This is known to occur in ovarian cancer patients—at diagnosis, they do not have strong expression of Bcl-2 proteins, and initially respond to chemotherapy with a 50-70% response rate. However, when the cancer develops drug resistance, 88% of patient samples have strong Bcl-XL expression. These tumors are also more aggressive and resistant to cisplatin, paclitaxel, topotecan, and gemcitabine. Increased Mcl-1 expression is also associated with poor prognosis in HGSC. Interestingly, resistance to ABT-737 (which inhibits Bcl-XL, Bcl-2, and Bcl-w) occurs due to overexpression of Mcl-1.

Figure 3:
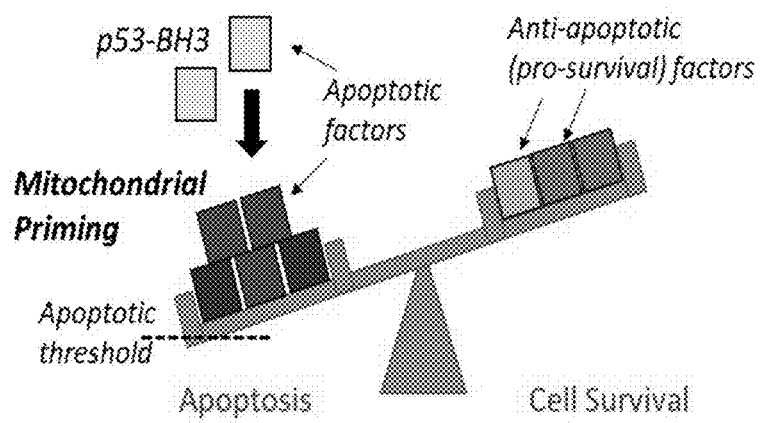
FIG. 3 is a schematic drawing of the pro-apoptotic and anti-apoptotic effects in the mitochondria affected by p53-BH3.

Combination therapies with BH3 mimetics have been proposed, based on BH3 profiling, which measures a tumor cell's responsiveness to BH3 pro-apoptotic peptides [76, 77]. BH3 profiling helps determine if a tumor will be responsive to chemotherapy. Cells with higher levels of pro- vs. anti-apoptotic proteins are closer to apoptosis or "mitochondrially primed" (FIG. 3) for cell death. If the balance can be tipped to pro-apoptotic (Bim, Bid, Noxa, Bad, or Puma) rather than anti-apoptotic (A1, Mcl-2, Bcl-XL, Bcl-2, and Bcl-W) proteins, drugs that trigger the intrinsic apoptotic pathway (e.g., chemotherapy or mitochondrial p53-BH3) and other agents will show a better response (FIG. 3). While patients with highly primed ovarian cancer cells may show a better clinical response to chemotherapy [78, 79], finding the right combination of drugs (chemotherapeutic/ other agent+BH3 mimetic for mitochondrial priming) has proven to be quite complex. A systems biology approach was used to determine the apoptotic priming potential of patient-derived ovarian cancer cell samples with PI3K/ AKT/mTOR pathway blockade (dysregulated in some HGSCs). Combinations of BH3 mimetics and PI3K/AKT/ mTOR inhibitors were predicted to have efficacy, but tumor reduction only appeared in subsets of PDX models. A multivariate analysis found differing drug sensitivities due to varying levels of specific pro- or anti-apoptotic proteins in patient cells. Resistance to double combination therapies developed, and sometimes triple drug combinations were needed, showing the continued development of resistance with evolution of the cancers.

p53-BH3 was Designed Overcome these Current Problems.

This fusion combines the power of mitochondrial p53 with a BH3-only apoptotic sensitizer protein. The possibility of cancer-specific inhibition of multiple anti-apoptotic proteins and activation of multiple pro-apoptotic factors would result in an apoptotic collapse of cancer cells, and would circumvent both drug resistance and toxicity (as in FIG. 2). With p53's known ability to neutralize anti-apoptotic proteins Mcl-1, Bcl-XL, Bcl-2, and Bcl-W, this can be combined with the ability of the BH3 protein to neutralize anti-apoptotic proteins. The BH3 only proteins to be fused to p53 include 4 of the 5 major BH3 only proteins: Bad (a potent inhibitor of Bcl-XL, a major anti-apoptotic factor often overexpressed in drug-resistant ovarian cancer; also inhibits Bcl-2 and Bcl-w), tBid (truncated Bid; truncated version localizes to mitochondria, neutralizes all 5 major anti-apoptotic factors and activates Bak and Bax as in FIG. 2), Bims, (localizes to mitochondria, inhibits Bcl-2, Bcl-XL, and Bcl-W, and activates Bax and Bak) and Noxa (potent inhibitor of anti-apoptotic Mcl-1, expressed in high levels in all ovarian cancer cell lines tested). A detailed rationale for all 4 is in the Approach section. And while the BH3 only protein Puma can inactivate all 5 anti-apoptotic factors, its regulation is complex, and its mitochondrial localization depends on modifications by or interactions with other proteins. While it has been tested in vitro for some cancers, Puma does not always go to mitochondria nor induce apoptosis, and therefore is not a first choice for a p53-BH3 fusion.

Improving Cancer Specificity—Cancer Specific Promoters and Modified Ad:

Cancer-specific promoters based on modified hTERT-CMV hybrids, an ovarian cancer-specific promoter (modified hTERT VP16-Gal4-WPRE), or a newly discovered ran (RAS-related nuclear protein) promoter can be used to restrict expression of gene therapy constructs to cancer cells. This is expected to eliminate/reduce off-target effects. hTERT and ran promoters work in mice. Also, a modified adenovirus (replication-deficient recombinant Ad serotype 5) which has tumor-specific tropism due to 1) deletion of viral E1A or E1B genomic regions, 2) incorporation of tumor-specific promoters into the viral genome, limiting expression only in malignant cells, and 3) improvement of transduction efficiency in tumor cells, which redirects virion entry into target cells (Clontech) can be used. The CD-PEG-RGD polymer can be used as a gene delivery system, conferring tumor specificity (via the CD and RGD moieties) and reduced immunogenicity of adenovirus (due to polymer "coating").

Preclinical Mouse Metastatic Ovarian Cancer Model:

A sophisticated metastatic ovarian cancer mouse model, can be used to test the efficacy of p53-BH3. This is a syngeneic orthotopic, metastatic ovarian preclinical cancer model that closely replicates characteristics and hallmarks seen in human ovarian cancer, including primary epithelial ovarian tumorigenic capacity, secondary peritoneal metastases and ascites, and corresponds to stage III-IV ovarian cancer in patients.

Figure 4:
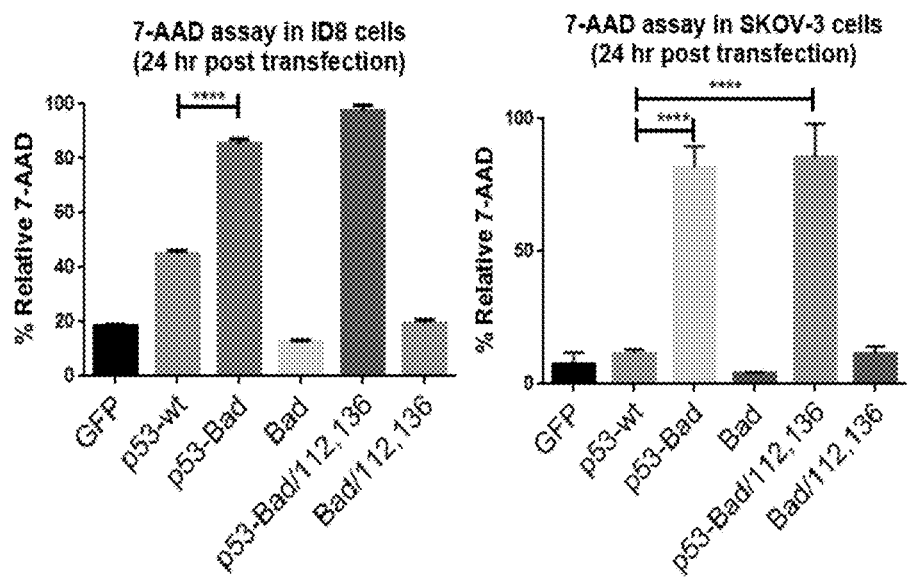
FIG. 4 shows the results of a 7-AAD assay in ID8 cells and SKOV-3 cells treated with different constructs.

Impact of this Work:

The significance of this work is to develop potent tumor suppressor-pro-apoptotic factor hybrids (p53-BH3) that can induce apoptosis in HGSC regardless of p53 mutation or anti-apoptotic factor expression. If successful, these new chimeric p53-BH3 constructs will: 1) demonstrate effective mitochondrial localization, 2) possess potent apoptotic activity against cancer cells regardless of p53 status, 3) show reduced toxicity in normal cells and reduced immunogenicity in an animal model. Data in FIG. 4 shows proof of concept in mouse (ID8) and human (SKOV-3) ovarian cancer cells, for the fusion between p53 and Bad (p53-Bad; contains a C-terminal tail-anchored MTS), where p53-Bad causes greater apoptosis (measured by 7-AAD) compared to wild-type p53 alone (p53-wt) or Bad alone (note: p53-Bad/ 112,136 and Bad/112, 136 contain S to A mutations that prevent binding to 14-3-3 protein, reported to sequester Bad in the cytoplasm, rather than the mitochondria [18, 93-95], and should perform better than unmodified Bad). p53-Bad is our most potent cell-killing construct to date. Having a collection of different p53-BH3 constructs could provide "personalization" of cancer therapy, depending on the anti-apoptotic proteins in a given cancer cell type.

3. Innovation:

p53-BH3 is a novel gene therapy construct that combines the power of mitochondrial p53 with a BH3-only apoptotic sensitizer protein. This tumor suppressor-pro-apoptotic factor hybrid is a new concept in cancer therapy, and has not been exploited previously. There are surprisingly few labs exploring re-engineering protein domains of p53 for translational gene therapy. Clinical trials of gene therapy using p53 to date have only used wt p53, which mainly activates the nuclear transcriptional program, activating the extrinsic apoptotic pathway. p53-BH3 constructs shift the current p53 research paradigm and combine activation of pro-apoptotic pathways and inactivation of anti-apoptotic pathways; thus, it has the potential to overcome drug resistance due to its multiple mechanisms of action (leading to apoptotic collapse). With this innovation, the field of p53 gene therapy with p53-BH3 can be "resurrected" by not requiring activation of hundreds of genes for activity.

Improving cancer specificity by engineering in a unique cancer specific promoter based on modified hTERT/hTERT- CMV hybrid promoters, ovarian cancer-specific promoters (a modified hTERT promoter (VP16-Gal4-WPRE), or ran promoter can restrict expression of gene therapy to cancer cells, thus providing an additional "safety" measure to non-cancerous cells.

Use of a polymer-modified adenovirus (Ad) hybrid for delivery of p53-based constructs has not been attempted before, and can be an effective way to deliver p53-BH3 to tumor cells with high expression, little to no toxicity, no immunogenicity, and overcomes issues with delivery of Ad alone. Modified Ad also confers tumor-specific tropism as mentioned in Significance section.

A distinctive animal model used is a syngeneic orthotopic, metastatic mouse ovarian preclinical cancer model. This sophisticated animal model closely replicates characteristics and hallmarks seen in late stage (III-IV) human ovarian cancer, including primary epithelial ovarian tumors, peritoneal metastases, and ascites.

Summary.

The combination of these integrated strategies represents breakthrough innovation for ovarian cancer treatment, with high translation potential, and high likelihood to transform the field. Disclosed herein are p53-BH3 constructs as lead candidates for killing ovarian cancer cells (regardless of cellular p53 status) in vitro and in vivo. The use of mitochondrial priming p53-BH3 constructs represents a paradigm shift that can allow the effective use of a chimeric version of p53, to extend or save the lives of women with ovarian cancer. Additionally, the development of p53-BH3 constructs can provide basic science knowledge of the use of p53 and BH3 only proteins in combination, and are applicable to other cancers that have poorly effective treatments (such as refractory lung and liver cancers).

Figure 5:
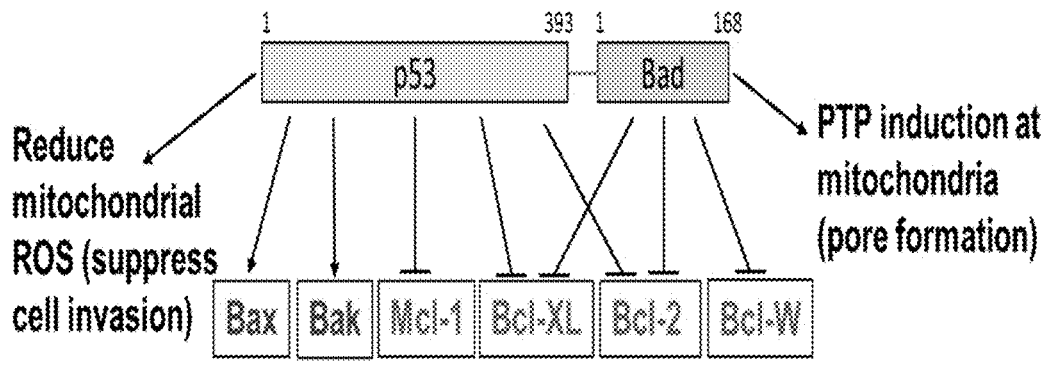
FIG. 5 shows a schematic diagram of p53-Bad hybrid activity.

4. Design and Cloning of p53-BH3 Gene Therapy Constructs (BH3 Only Proteins to be Tested: Bad, tBid, Bims, and Noxa) with a Cancer-Specific Promoter Capable of Mitochondrial Localization and Direct Activation of Apoptosis in Ovarian Cancer Cells Rationale: designing a p53-hybrid agent capable of highly potent apoptosis of cancer cells can result in potent amplification of the p53 killing effect at the mitochondria achieved by fusing it with a BH3 only apoptotic protein that targets the mitochondria and can directly bind to and inactivate anti-apoptotic proteins. The fusion of p53 and a BH3 only protein (vs. introducing the genes separately) is to ensure that both expressed proteins are at the mitochondria simultaneously and can act in concert. p53 at the mitochondria can bind to pro-apoptotic Bak and Bax, allowing for their homo-oligomerization, leading to mitochondrial pore formation, cyt C release, activation of caspases, and apoptosis. p53 can also neutralize anti-apoptotic Mcl-1, Bcl-XL, Bcl-2, and Bcl-W. Cytoplasmic p53 can bind Bcl-W or Bcl-XL, and release Bax or Bak, respectively, and suppress cancer cell invasion by reducing mitochondrial ROS levels. For fusion with p53, BH3 proteins Bad, tBid, BimS, and Noxa are proposed with rationale as follows:

Fusing p53 to pro-apoptotic Bad (p53-Bad): Bad is a potent inhibitor of Bcl-XL, a major anti-apoptotic factor that is often overexpressed in drug-resistant ovarian cancer. Pro-apoptotic activity and mitochondrial localization of Bad are reported to be regulated via phosphorylation (by Akt or Ras) of its serine residues. Phosphorylation of S112 and S136 induces Bad binding to 14-3-3 protein which renders it inactive (unable to induce apoptosis). Further, phosphorylation of S155 dissociates Bad from Bcl-XL, leading to cell survival. Therefore, dephosphorylation of Bad activates apoptosis. When dephosphorylated (not sequestered by 14-3-3), Bad targets the mitochondria via lipid binding motifs (47aa c-terminal tail) that interact with mitochondrial membrane phospholipids like cardiolipin. S to A mutations (at residues 112, 136, and 155) in Bad are proposed in order to increase apoptotic potential. In addition to Bcl-XL, mitochondrial Bad inactivates Bcl-2 and Bcl-W as well, and can turn on a Bak/Bax independent pro-apoptotic switch that engages the mitochondrial permeability transition pore (PTP), providing a unique and separate cell death mechanism. FIG. 5 summarizes mechanisms of action of p53-Bad (red=induction of pro-apoptotic proteins; green=inhibition of anti-apoptotic proteins). Due to multiple mechanisms of actions, p53-Bad is expected to be a prime candidate, and indeed, the data (FIG. 4) indicates that p53 fused to S112A/ S136A double mutant Bad (p53-Bad/112,136) does induce robust apoptosis in both ID8 (mouse) and SKOV-3 (human) ovarian cancer cell lines, exceeding that of wt p53 or Bad alone.

Fusing p53 to truncated pro-apoptotic tBid (p53-tBid): Bid is known to neutralize all five major anti-apoptotic factors (shown in FIG. 2, bottom). Bid is the messenger that connects the extrinsic apoptosis pathway (by the FAS death receptor) to the mitochondrial death machinery. Bid contains 2 hydrophobic helices (H7 and H8), containing the mitochondrial targeting sequence, surrounded by 6 amphipathic helices (H1 to H6). When Bid is cleaved by caspase 8 at Asp59, the N-terminus of Bid with H1 and H2 is released, and the mitochondrial targeting domains are exposed, which induces tBid localization to the mitochondria. Importantly, H1 and H2 have been reported to be non-essential to the proper folding of Bid. tBid's C-terminus has been used to successfully target GFP to the mitochondria. tBid can be tested for p53 mitochondrial localization by fusing truncated Bid to p53. This p53-tBid retains the BH3 binding domain with the hydrophobic cleft intact, which can neutralize anti-apoptotic Bcl-2 and Bcl-XL.

Fusing p53 to pro-apoptotic Bim (p53-BimS): Bim has 3 isoforms: BimEL (extra-long), BimL (long), and BimS (short). BimL and BimEL are constitutively expressed in normal cells, but are sequestered by LC8 cytoplasmic dynein light chain proteins, a component of the microtubules, through as 50 to 55 of BimL. When bound to microtubules, BimL and BimEL can sense disruption of the integrity of cytoskeleton, and hence are released from microtubules and localize to the mitochondria to neutralize Bcl-2, Bcl-XL, and Bcl-W, and activate Bax and Bak. BimS is only expressed when the cell is induced by a high dose of cytotoxic drug to commit to apoptosis. BimS also lacks the microtubule-binding domain [84], and therefore constitutively localizes to the mitochondria. The MTS of BimS is located within the last 30 amino acids (80 to 110) of the C-terminus and contains a transmembrane domain similar to Bak and Bax. BimS (110 as [82]) will be used to fuse with p53 due to its superior cytotoxicity over both BimEL and BimL, and direct mitochondrial localization.

Fusing p53 to pro-apoptotic Noxa (p53-Noxa): Noxa is the smallest of the BH3 proteins (54 aa), and is a potent inhibitor of Mcl-1, an anti-apoptotic factor expressed in high levels (more than 0.4 million mRNA copy numbers) in ovarian cancer cell lines tested in a Bcl-2 family expression survey. Noxa also binds to and inhbits A1 [104]. Noxa is a target gene of p53 that is expressed when the cell suffers cellular damage. However, p53 is mutated in >96% HGSC cases, which is expected to greatly impair Noxa expression. Reintroduction of Noxa has been reported to re-sensitize cisplatin-resistant ovarian cancer. Noxa contains a MTS at its C-terminus, like other BH3 proteins. By fusing p53 to Noxa, we aim to achieve the apoptotic effect of both p53 and Noxa at the mitochondria. Mutation of Noxa at ser 13 to ala will also be tested as it has been reported that phosphorylation at ser 13 inhibits apoptosis.

Linkers between p53 and BH3 constructs (as in FIG. 1) will be explored. Linkers derived from multi-domain proteins are the foundation in linker design, and can improve expression, stability, and biological activity. While the first constructs subcloned (p53-Bad, p53-Bad/112,136) contained base pairs encoding a few random as sequences (GTAGPGS) between DNA sequences encoding p53 and the BH3 protein, more rational standard linkers will be attempted, including a flexible linker, a rigid linker, and 2 helical linkers of various lengths (see Table 1 for rationale and sequences). There is no a priori way to determine which of these will work optimally, so they will be tested. The optimal linker would allow for maximal functionality of each protein (p53 or BH3 protein) for high expression and apoptotic activity.

TABLE 1

Possible linker sequences between p53 and BH3 protein to be tested

| Linker sequence | Rationale for use from Shen and colleagues [5, 6] |
|---|---|
| (GGGG)$_3$ | The most widely used flexible linker; used to increase stability/folding |
| (PAPAPA)$_3$ | Rigid linker used to increase biological activity |
| (EAAAK)$_3$ | Alpha-helical linker; increases stability/biological activity (rigid spacer between functional domains in proteins) |
| [LEA(EAAAK)$_4$]$_2$LE | Another alpha helical linker; increases stability/biological activity (longer length may give more separation of functional domains) |

Cancer specific promoters based on the well-studied hTERT promoter, a hTERT-CMV hybrid, a hTERT-based ovarian cancer specific promoter, and a newer promoter, ran (promoter from RAS related nuclear protein), will be tested (listed in Table 2). The hTERT promoters are well-known and have been used for cancer specificity (even in mice [89, 90]), but often suffer from low expression. The critical factors that regulate hTERT transcription are c-myc and activating enhancer-binding protein-2 (AP-2), located within 200 bp upstream from the hTERT transcription start site. Most hTERT promoters in the literature have this critical region. However, longer hTERT has been used (up to 400 bp upstream of the start sites) because Wilms tumor transcription factor (WT-1) binds to this −400 bp to −200 bp region. WT-1, which regulates growth response elements, is known to be associated with cancer metastases and invasion. The optimal length of the hTERT promoter for highest expression in ovarian cancer remains unclear and will be tested. Based on the literature, several hTERT promoter candidates will be tested in our ovarian cancer lines. A hTERT-CMV hybrid called hTC fusion has been proposed to have greater expression compared to hTERT alone. Another ovarian cancer specific promoter (VP16-Gal4-WPRE) consists of a 2-step amplification system coupled with the WRPE enhancer (posttranscriptional regulatory element of the woodchuck hepatitis virus) with ovarian cancer cell specificity. Lastly, a newly discovered cancer-specific ran (RAS-related nuclear protein) promoter, identified using a top-down algorithm approach for promoter selection, with both excellent cancer specificity and strength similar to CMV in vitro in ovarian cancer cells (and in vivo in a mouse bladder cancer model), will also be tested. The optimal promoter that has: 1) high expression in ovarian cancer cells and 2) little to no expression in normal cells, to drive the expression of our novel p53-BH3 constructs will be determined. Preliminary data in FIG. 6 indicate that hTERT and hTERT-CMV promoters (Table 2) tested so far do show cancer-specific expression of reporter gene EGFP. Promoters #3 and 4 in Table 2 have yet to be tested. Promoters also have to be tested in all other ovarian cancer cell lines as well (in Table 3).

TABLE 2

Cancer specific promoters to be designed and tested.

| # | Promoter | hTERT number if applicable (hTERT transcription start side from [21]) |
|---|---|---|
| 1 | hTERT | −204 to +5, −27 to +5, −279 to +5, −408 to +5, or −408 to +55 |
| 2 | hTC fusion | −456 to −2 upstream of start codon (hTERT) and bases −1017 to −901 upstream of human CMV major immediate early protein start codon |
| 3 | Ov car specific | modified hTERT promoter (VP16-Gal4-WPRE) |
| 4 | Ran | 589-635 (numbering from NM_006325) |

Rigorous Experimental Plan and Additional Preliminary Data for Aim 1:

Plasmid design and construction: Plasmids encoding BH3 proteins (Bad, 169 aa; tBid, 146 aa; BimS, 110 aa; and Noxa, 54 aa) were purchased from Sino Biological, and can be subcloned to the C-terminus of p53 (rather than N-terminus) to retain the functionality of the MTSs located in the C-terminal tails of the BH3 proteins (the main characteristic of tail-anchored mitochondrial proteins). All constructs can be have a EGFP tag on the N-terminus of p53 so that the localization of the constructs can be tracked after transfected into cells. Linkers (from Table 1) between p53 and the BH3 protein of interest will be subcloned by back translating as sequences to DNA base pairs with human codon usage considered to make corresponding oligos for subcloning. Subcloning details for p53-BH3 constructs are as follows (with linker subcloning as above): p53-Bad and p53-Bad with S112A, S136A mutations using site-directed mutagenesis (called p53-Bad/112,136) have already been subcloned with Bad at the C-terminus of EGFP-p53 (with a constitutive CMV promoter; short random linker of GTAGPGS). Another S155A mutation was made to create a triple mutant (p53-Bad/112,136,155) but did not have significantly better apoptosis over the double mutant so far. All p53-Bad plasmids can be subcloned with linkers in Table 1. S to A mutations can render p53-Bad "unphosphorylatable" and should show higher apoptosis (as lack of phosphorylation prevents binding to 14-3-3 protein, and allows Bad to activate apoptotic pathways). Bad and Bad/112,136 (without p53) were also cloned to determine the effect of Bad alone.

p53-tBid: truncated Bid (tBid) without amino residues 1 to 59 has been cloned to the C-terminus of p53, and should constitutively localize to the mitochondria due to the exposed MTS. A full-length Bid with D49A mutation can also be cloned into the C-terminus end of p53 (called p53-Bid/49). This p53-Bid/49 is un-cleavable by caspase and can serve as an experimental control. Bid-D49A is known to be incapable of mitochondria localization. tBid and Bid-D49A will also be cloned without p53 to determine their activity.

p53-BimS: The short isoform of Bim (BimS or BimS) has been cloned to the C-terminus of p53 (does not have a microtubule binding domain), and should localize to the mitochondria. BimS without the last 30 amino acids (BimSAC) will be used as the negative control for its inability to localize to the mitochondria.

p53-Noxa: Similar to BimS, Noxa and NoxaΔC (last 20 amino acids deleted) will be cloned to the C-terminus of p53. Noxa constitutively localizes to the mitochondria, while NoxaΔC will fail to localize. Noxa and NoxaΔC (without p53) can also be tagged with N-terminal EGFP as the control group for the effect of p53.

Figure 6:
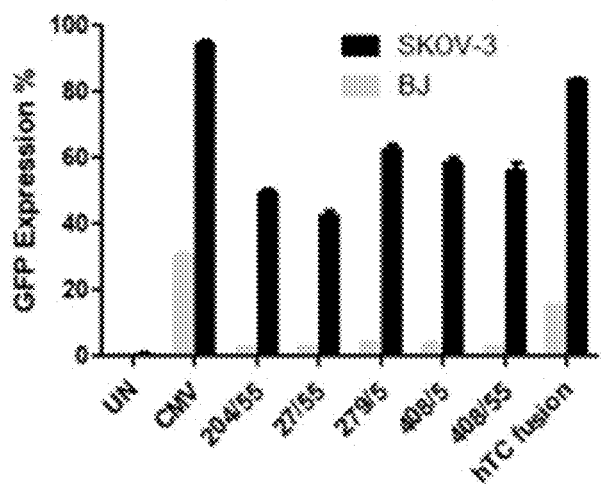
FIG. 6 shows promoter activity in BJ normal cell s(black) and SKOV-3 ovarian cells (gray) (n=3).

Promoters #1-2 in Table 1 have already been subcloned into an EGFP reporter vector; cloning of promoters #3 and 4 have yet to be done. FIG. 6 shows several promoters that express a GFP plasmid in SKOV-3 (gray) human ovarian cancer cell lines (compared to the strong, constitutive CMV promoter; UN=nothing transfected), with low expression in normal BJ cells (black). Candidate(s) promoters with highest expression (measured by flow sorting of EGFP(+) cells) in ovarian cancer cells listed in Table 3 (and not normal cells) can be subcloned into p53-BH3 vectors.

Cell lines, transient transfections: ID8 (mouse) and SKOV-3 (human) ovarian cancer cells, and normal BJ fibroblasts (subset of Table 3) can be used for mitochondrial localization studies (microscopy) and 7-AAD apoptosis assays. More extensive apoptotic assays can be tested in Aim 2 with all cell lines. For this aim, cells will be transiently transfected with lipofectamine.

Figure 7:
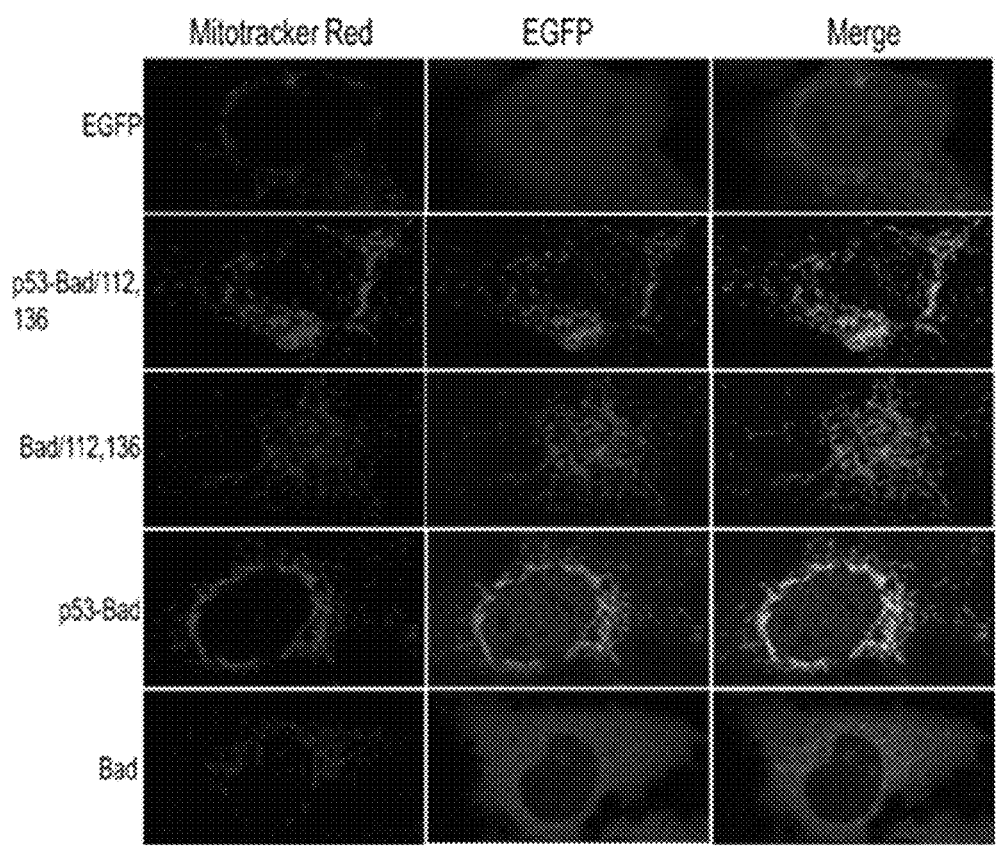
FIG. 7 shows fluorescence microscopy of EGFP-tagged constructs (driven by CMV promoter).
Figure 8:
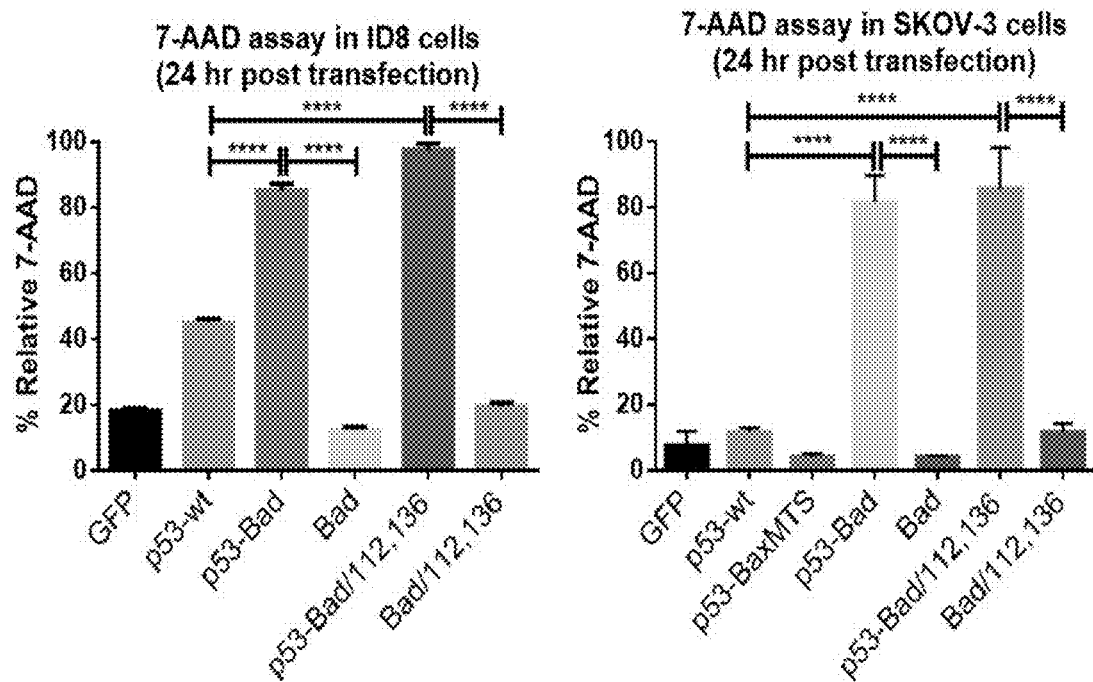
FIG. 8 shows first proof of concept of p53-BH3 constructs. Both p53-Bad/112.136 and p53-Bad outperform all previous constructs, including p53-BakMTS or $p^{53}$-BaxMTS which target the mitochondria but do not contain a BH3 domain, and wt p53. All have a CMV promoter; n=3, performed twice (representative expt shown); ****p<0.0001.

Mitochondrial staining, microscopy, and image analysis: To verify mitochondrial localization of constructs, cells transfected with constructs will be stained with MitoTracker Red FM (Invitrogen) as before. Images of p53-BH3 (EGFP tagged on N-terminus) can be acquired 18 h post-transfection with an Olympus IX71F fluorescence microscope with a F-View Monochrome CCD camera [13, 112] and analyzed with ImageJ using Pearson's correlation coefficient (PCC) and post Costes' algorithm [13, 112, 113]. PCC≥0.6 are considered to be colocalized. Preliminary data in FIG. 7 indicate mitochondrial localization of CMV-driven p53-Bad/112,136 Bad/112,136, and p 53-Bad (labeled with stars) in human ovarian cancer SKOV-3 cells, where yellow=colocalized. Interestingly, p53-Bad (row 4) appears to have some nuclear localization whereas p53-Bad/112,136 (row 2) does not. Apoptosis assay: 7-AAD assay (measuring late-stage apoptosis) can be performed as done before as an initial screen. As before, cells can be stained with 400 L working solution of 7-aminoactinomycin D (7-AAD) 24 hr post-transfection. Cells can be analyzed and gated for EGFP with the same fluorescence intensity to ensure equal detection of proteins Statistical analysis/rigor: experiments will be performed in triplicate (n=3) and repeated 3 times on separate days; one-way ANOVA was used/will be used for all aims, with Tukey's or Bonferroni's post-test; p<0.05 is considered significant. Critical preliminary data in FIG. 8 shows that p53-Bad/112,136 (with two S to A mutations) and p53-Bad induce robust apoptosis (measured by 7-AAD, late apoptosis) in 2 ovarian cancer cell lines (mouse ID8 and human SKOV-3), providing proof of concept. While p53-Bad/112,136 was expected to be more potent than p53-Bad due to lack of phosphorylation (and hence no binding to 14-3-3 protein which would otherwise sequester it in the cytoplasm), it was not significantly different. It could be, that when attached to p53, Bad is not able to associate with 14-3-3. Regardless, p53-Bad and p53-Bad/112,136 are both able to potently kill ovarian cancer cells more effectively than wild-type (wt) p53, Bad alone, or Bad/112,136 alone. Bad and Bad/112,136 alone are inactive, indicating the necessity of fusion to p53 for activity. Further assays demonstrating activity will be tested in Aim 2.

Benchmarks/Expected Outcomes and Alternative Strategies: The newly discovered Ran promoter can provide the highest ovarian cancer cell specificity/expression; however, hTERT-CMV hybrid promoters can also yield high expression specific for ovarian cancer cells. Some promoters may be more active in particular cell lines. All p53-BH3 vectors, regardless of promoter, can express and localize in the mitochondria, as seen in SKOV-3 human ov car cells (FIG. 7) and show some degree of apoptosis (as in FIG. 8). Serine to alanine mutations in Bad (esp. S155A since not yet tested) may reduce activity of the protein due to as substitution, but p53-Bad without mutations is an alternative that already works. An alternative strategy to using a mitochondrially targeted p53 fused to a BH3 protein for gene therapy is transfection of a p53-MTS, with the BH3 protein (Bad, tBid, BimS, Noxa) not fused, using a bi-cistronic vector or as 2 plasmids. Of the p53-BH3 constructs, p53-tBid could be very potent, as it inhibits all 5 major anti-apoptotic proteins (Bad inhibits 3 of the 5 anti-apoptotic proteins as does BimS, but these have other mechanisms of action as well). The Noxa construct may be a weaker construct since the main target is Mcl-1, but it is of interest since Mcl-1 overexpression is: 1) associated with poor prognosis in HGSC [72], and 2) implicated in resistance to drugs like ABT-737 (which inhibits Bcl-XL, Bcl-2, and Bcl-w). The optimized p53-BH3 construct(s) from this aim can be a highly potent inducer of apoptosis with a promoter that restricts expression to ovarian cancer cells 1. Determine the Apoptotic Potential of p53-BH3 in Ovarian Cancer Cell Lines (Human and Mouse) with Varying p53 Status, and Determine the Mechanisms of Apoptosis Rationale: The killing potential of the optimized p53-BH3 constructs from above description can be tested in additional true HGSC ovarian cancer and other cell lines in Table 3. To determine if p53-BH3 is active regardless of p53 status, ovarian cancer cells with varying p53 status including dominant negative Kuramochi (which is also a BRCA1 mutant), dominant negative/gain of function OVCAR-3, mutant p53 OVCAR-4, and p53 null SKOV-3 can be tested; the murine ID8 cell line to be used in animal studies in aim 3 and normal cell lines BJ and IHOEC will also be tested. Except for OVCAR-4 and IHOEC, all cell lines have already been purchased, grown in culture, and various assays tested already.

Assays representing early, mid, and late apoptosis can be done as before, including TMRE assay (early apoptosis; mitochondrial depolarization/outer membrane permeabilization) [16]; caspase-3/7 assay (early apoptosis, cyt C release), annexin V-APC (mid-stage apoptosis); 7-AAD assay (late apoptosis; details in Aim 1), TUNEL assay (DNA nicks/fragmentation, late apotosis), and; cells in Table 2 can be transfected with p53-BH3 constructs using lipofectamine. Besides apoptosis, cell proliferation/viability and colony forming assay (CFA; tests oncogenic potential) will also be tested. A nuclear transcriptional assay will also be used to show that p53-BH3 act via the mitochondria rather than the nucleus.

For determining mechanism(s) of apoptosis (shown in FIGS. 2 and 4), quantitative PCR, mitochondrial fractionation/Western blotting, and co-IP assays will be performed to look for interactions between p53-BH3 and pro-apoptotic Bak and Bax, and anti-apoptotic A1, Mcl-1, Bcl-XL, Bcl-2, and Bcl-W. Reduction of ROS (mediated by p53) for all constructs, and PTP formation at the mitochondria will also be tested. Mitochondrial ROS and PTP will be measured as in; PTP will be measured via TMRE assay.

TABLE 3

Cell lines used in Aim 2 (ovarian cancer cells or normal cells).

| Ovarian cancer cells | p53 status | BRCA1/ 2 status | Characteristics (all cell lines are human except ID8) (note: all human cell lines are commercially available) |
|---|---|---|---|
| Kuramochi | Dom neg, D281Y | BRCA1 mut | From ov car ascites; epithelial-like morphology, HGSC [114] |
| OVCAR-3 | Dom neg, gain of fct, R248Q | Wt | Ovarian adenocarcinoma; epithelial; HGSC [114] |
| OVCAR-4 | L130V mut | Wt | Serous ovarian adenocarcinoma; HGSC [114]; resistant to platinum |
| SKOV-3 | p53 null | Wt | Ovarian adenocarcinoma; from ascites; not likely HGSC [114] |
| ID8 cells | p53 null | Wt | Murine ovarian epithelial cells spontaneously transformed [115] |
| Normal cells: BJ, IHOEC | Wt p53 | n/a | BJ: Normal fibroblasts [116]; IHOEC: SV40 immortalized ovarian epithelial cells |

Rigorous Experimental Plan

Figure 9:
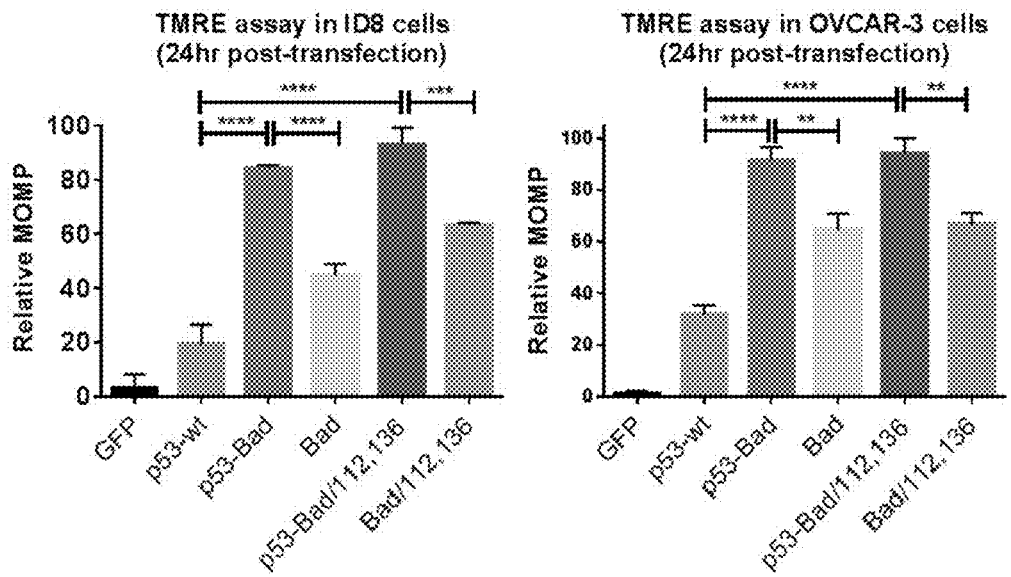
FIG. 9 shows TMRE assay results in ID8 and OVCAR-3 cell lines (n=3) where p53-Bad and p53-Bad/112,136 show the most mitochondrial depolarization.
Figure 10:
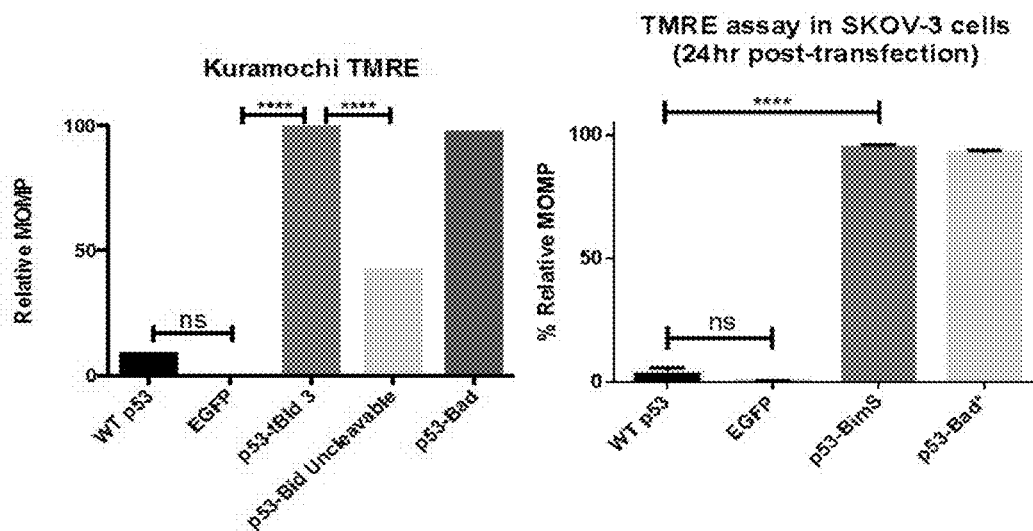
FIG. 10 shows p53-tBid and p53-BimS.

TMRE assay (early apoptosis): 24 hr post-transfection, cells can be incubated with 100 nM tetramethylrhodamine ethyl ester (Invitrogen) for 30 min at 370 C then pelleted and resuspended in 300 µL annexin-V binding buffer (Invitrogen). Flow cytometry can be used to analyze GFP positive cells using the PE-A channel (excitation at 561 nm with emission at 585/15). Loss in TMRE intensity represents mitochondrial depolarization, which correlates to mitochondrial outer membrane permeabilization (MOMP). FIG. 9 shows TMRE assay results in ID8 and OVCAR-3 cell lines (n=3) where p53-Bad and p53-Bad/112,136 show the most mitochondrial depolarization. Interestingly, using TMRE (early apoptotic event), Bad and Bad/112,136 appear to have some activity particularly in OVCAR-3 cells (unlike in FIG. 7 using 7-AAD, late apoptosis assay, for ID8 and SKOV-3). Bad alone constructs may have some activity, but may be weaker or slower acting than p53-Bad constructs. This underscores the importance of using apoptotic, cell death, proliferation, and oncogenic assays to paint a complete picture of construct potency/efficacy. Additional proof of concept is shown in FIG. 10, where p53-tBid and p53-BimS also show significant activity (both have the alpha helix linker in Table 1).

Figure 11:
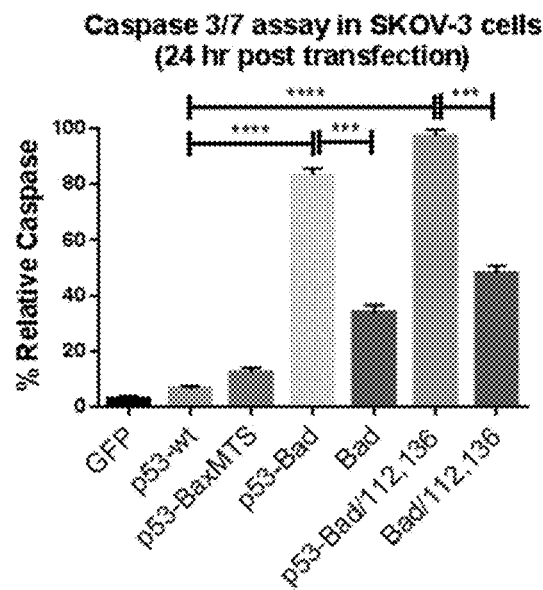
FIG. 11 shows Caspase 3/7 assay in SKOV-3 cells.

Caspase 3/7 assay (early apoptosis): The FLICA 660 Caspase 3/7 assay kit (ImmunoChemistry Tech.) will be used to determine caspase activity as before [16, 17, 117]. 24 hr post-transfection, pelleted cells are resuspended with fluorescent inhibitor probe 660-DEVD-FMK solution, which covalently couples to active enzymes (unbound washed away). Stained cells are analyzed by flow cytometry using FACSCanto-II and FACSDiva Software. The cells are gated for GFP (excitation 488 nm/660 nm; detection 507 nm/690 nm for GFP and FLICA, respectively). Preliminary data shows p53-Bad constructs have caspase activity in SKOV-3 cells (n=3, FIG. 11), showing further proof-of-concept. New p53-Bad constructs outperform mitochondrially directed p53 (with Bax MTS, 3rd bar).

Annexin V assay (mid-stage apoptosis): 24 hr post-transfection, cells are resuspended in Annexin binding buffer (Invitrogen) and incubated with Annexin-APC reagent for 15 minutes as before [58]. Cells will be gated for EGFP and analyzed using FACSCanto-II/FACSDiva software (excitation 488 nm/APC; detection 507/660 nm). TUNEL assay (late apoptosis): DNA fragmentation will be observed using live cell microscopy as before. 48 hr after transfection, nuclear stain H33342 will be added to cells and incubated for 15 min at 37° C. Cells are analyzed with an inverted fluorescence microscope (Olympus IX101D), excited at 408/20 nm; detected at 510/20 nm) and imaged with an F-view Monochrome camera at 60x objective. The nuclei of 50 transfected cells per group will be categorized as healthy (round) or fragmented (punctate).

Cell proliferation and viability assay: Trypan blue exclusion and MTT/MTS assay can be used. 24-72 hr after transfections, cells can be stained with trypan blue, and the number of viable cells (not blue) and non-viable cells (blue) can be counted. MTT/MTS assay utilizes tetrazolium compound to measure the ability of cells to generate ATP/proliferate. The CellTiter 96 Aqueous One Solution Cell Proliferation Assay (Promega) will be used to analyze cell viability 24-72 hr post-transfection (490 nm absorption with microplate reader).

Colony forming assay (CFA): Cytoselect 96-well Cell Transformation Assay (Cell Biolabs) can be used to test the transformative (oncogenic) potential of the transfected cells as before. Cells can be harvested 24 hr after transfection and resuspended and placed on an agar layer and enriched with complete growth medium and incubated for 7 days at 37° C. and 5% CO2. After lysing, cell lysates can be mixed with CyQuant GR working solution for 10 min at room temperature. Fluorescence (485/520 nm) can be detected using a microplate reader.

Nuclear Transcriptional Activity Assay: To confirm that the apoptotic activity of these constructs is transcriptionally independent, the p53-BH3 constructs mentioned above will be co-transfected with p53-Luc-Cis-reporter encoding firefly luciferase (Agilent Technologies). pRL-SV40 plasmid encoding Renilla luciferase will serve as the internal control in cells, and Dual-Glo luciferase assay system (Promega) will be used as we have before. The reporter gene assay utilizes a p53 consensus reporter sequence (TGCCTGGACTTGCCTGG)14. p53-BH3 constructs do not demonstrate nuclear activity in SKOV-3 and Kuramochi cells (data not shown).

Quantitative PCR: The mRNA expression level of anti- and pro-apoptotic factors can be determined. Total RNA can be extracted from each cell line using RNA extraction kit (Thermo Scientific). The RNA quantity and quality can be verified using NanoDrop 2000 and BioRad RNA Analysis kit (BioRad). Reverse transcription can be carried out using the qScript cDNA Supermix (Quanta Biosciences). The primers can be designed based on the qPCR Primer Database (Invitrogen) as previously. The cDNA will be subjected to real-time quantitative PCR with SYBR Green kit (Qiagen) to detect individual anti-apoptotic factors. The relative expression levels will be normalized to Quantum RNA f-Actin Internal Standards (Thermo Scientific.

Mitochondria extraction and Western blotting: mitochondria from log-phase cells can be extracted using a mitochondria isolation kit (Thermo Scientific). After extraction, mitochondria can be lysed with 2% CHAPS in Tris-buffered saline. Before Western blotting, the amount of protein is quantified using BCA protein assay kit (Thermo Scientific). Standard Western blotting procedures will be followed as before. 1o antibodies against each specific Bcl-2 family proteins will be detected with HRP-conjugated 2o antibodies using SuperSignal chemiluminescent substrate (Thermo Scientific) and a FluorChem FC2 imager/software (Alpha Innotech). Western blot will confirm the expression of anti-apoptotic and pro-apoptotic factors.

Co-IP (co-immunoprecipitation) will be performed to elucidate the binding partners of individual p53-BH3. Mitochondrial membrane proteins can be extracted using MemPER Plus Membrane Protein Extraction Kit (Thermo Scientific). Anti-GFP antibody can be bound to magnetic beads using Dynabeads co-IP kit (Invitrogen). 24 hr post-transfection, the cells are pelleted, and the proteins can be extracted and incubated with anti-GFP coupled Dynabeads. The complex can be magnetically collected, washed, eluted and probed via Western blot.

Statistical analysis/rigor: experiments will be performed in triplicate (n=3), and repeated 3 times (on 3 separate days); one-way ANOVA will be used for all aims, with Bonferroni's post-test; $p<0.05$ considered significant.

Benchmarks/Expected Outcomes and Alternative Strategies for Aim 2: p53-BH3 constructs are expected to induce higher apoptosis than wt p53, p53-MTS, or BH3 constructs alone (with apoptosis greater than negative controls EGFP or untreated) in ovarian cancer cell lines, regardless of p53 status. Normal cells should not express (or have very low levels of) p53-BH3 constructs due to the cancer specific promoter, and therefore no/low apoptosis. p53-BH3 constructs should not activate a nuclear reporter gene assay (due to localization to mitochondria), and should interact with pro- and antiapoptotic partners as measured by co-IP (the gold standard). Mammalian two-hybrid system (as we have done before) is an alternative for co-immunoprecipitation. Western blotting can indicate upregulation of certain anti-apoptotic proteins in response to blockade of others. We have extensive experience for the majority of the assays above. Transient interactions between p53-BH3 and partners may be detected with fluorescence resonance energy transfer (FRET) or bimolecular fluorescence complementation (BIFC) methods, albeit more complex. The top 2 constructs here will move on to the below experimental design.

2. Deliver p53-BH3 Using an Advanced Polymeric-Adenovirus (Ad) Hybrid Delivery System (Using Modified Ad with CD-PEG-RGD Polymer) First In Vitro, then In Vivo by Intraperitoneal Injection into a Pre-Clinical Syngeneic Orthotopic Metastatic Mouse Ovarian Cancer Model Rationale/Premise for Aim 3: To effectively deliver optimized p53-BH3, a unique polymeric-adenovirus hybrid drug delivery system with high expression, low toxicity, and lack of immunogenicity in vivo can be used. RGD-tumor targeted bioreducible polymer called CD-PEG-RGD (poly (cystaminebisacryl-amide-diaminohexane)-polyethylene glycol linked to RGD (Arg-Gly-Asp)) has already been synthesized with help from Kim et al. Adenovirus (encoding p53-BH3) will be coated with CD-PEG-RGD which has stability in extracellular fluid and can bioreduce and release genetic material [124]. The cyclic RGD portion targets αvβv integrins found on tumors; CD alone improves uptake over naked adenovirus regardless of integrin status. Polymer-Ad p53-BH3 can be first tested in vitro using apoptotic and other cell death assays (as in Aim 2) in ID8 cells (as ID8 are the cells used for tumor implantation in the animal model). A pre-pilot study has been done with IP injection of polymer-Ad using Dr. Janat-Amsbury's syngeneic orthotopic, metastatic mouse ovarian preclinical cancer model which closely replicates characteristics in human ovarian cancer, including primary epithelial ovarian tumors, secondary peritoneal metastases, and ascites.

Rigorous Experimental Plan and Preliminary Data for Aim 3:

Polymer-adenovirus synthesis and preparation for cell and animal experiments: CD-PEG-RGD (bioreducible poly(cystaminebisacrylamide-diaminohexane)-polyethylene glycol linked to a RGD (Arg-Gly-Asp)) has been synthesized using published methods with PEG1000 (Mal-PEG-NHS 1K from Biochempeg) and cyclic RGD peptide from NovoPro Biosciences (cat #303458). Conjugation and size were verified by NMR. p53-BH3 constructs will be subcloned into AdenoX System 3 (Clontech) with a constitutive CMV promoter and ZsGreen (we already have made wt p53 in this Ad vector). Optimized cancer-specific promoter from Aim 1 will replace CMV in all Ad constructs as well. Polymer and adenovirus are mixed by tapping, and after 60 min at RT, added to ID8 cells in serum free media and incubated for 4 h prior to apoptosis/cell death assays (as in Aim 2). A 0.3% (% RGD conjugation) and a $0.31 \times 10^4$ polymer:Ad ratio (using Ad-CMV-ZsGreen control) had optimal expression (% GFP positive) and minimal toxicity in vitro in ID8 cells in a pilot experiment (data not shown). It should be noted that the polymer is not expected to increase transfection efficiency in vitro since Ad transfection efficiency is already very high in ID8 cells. For in vitro studies, the CD-PEG-RGD (CDPR)-coated Ad-p53-BH3 will be used to infect ID8 cells with mutiplicity of infection (MOI) ranging from 50 to 250 as before [57]. 7-AAD, Caspase 3/7, TMRE, and Annexin-V assay can be used to analyze the efficacy of CDPR-Ad-p53-BH3 compared to various controls (CDPR-Ad-p53-wt, CDPR-Ad-GFP, CDPR-BH3MTS, CDPR only, and naked viruses) similar to Aim 2. The top 2 p53-BH3 constructs with highest cell death in vitro will be used in vivo.

Figure 12:
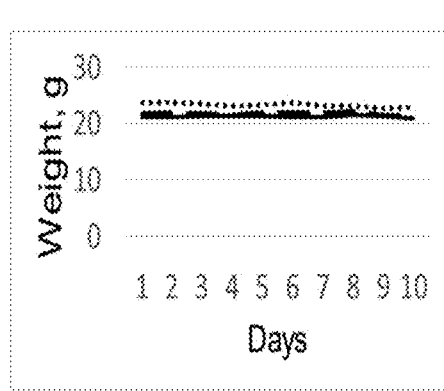
FIG. 12 shows weight of mice over time.
Figure 13:
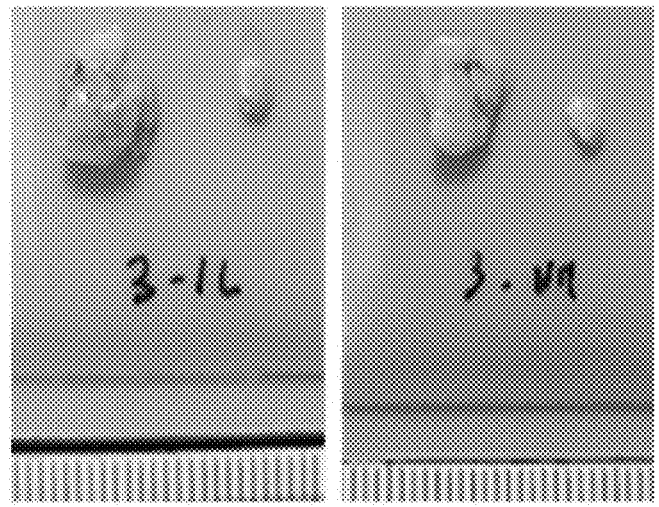
FIG. 13 shows photograph of ovarian tumors.

Animal procedures: 6-8 week old female C57BL/6 mice (Jackson Labs) will have a single dorsal midline incision made to access ovaries. $1 \times 10^6$ ID8 cells will be injected into left ovarian bursa (PBS control injected into contralateral ovary), and monitored daily. Tumors will be grown 6-8 weeks (2-2.5 cm3), prior to initiating treatment (before mets and ascites form). 500 ul volume IP injections of polymer-Ad (using 0.3% conjugation ratio, at $0.31 \times 10^4$ and $2.5 \times 10^5$ polymer:Ad ratios will be given once daily for 10 days (Table 4). Total mice # is 117 plus ~20% extra=141. Tumor measurements and efficacy of treatment: Mice will be weighed daily. After completion of treatment, mice will be weighed, sacrificed, organs harvested, and tumors excised (tumor volume and weight measured; ascites collected) as before. In a preliminary toxicity study using IP injected polymer alone (dashed line, n=2) and polymer with Ad (solid line, n=3) compared to PBS control (dotted line, n=2), after 10 days of injections, mice showed no gross toxicity in terms of weight loss (FIG. 12), or immunogenicity (no swelling, inflammation, or redness at injection site; data not shown). FIG. 13 demonstrates the ability to create ovarian tumors (left ovary with injected tumor cells, vs. untreated right ovary; harvested approximately 8 weeks after initial ID8 cell injections).

Toxicity/immunogenicity: can be performed with ARUP Laboratories' pathologists as before. Normal tissue surrounding the tumors will be inspected for signs of inflammation, including redness, swelling, edema, and discoloration (Draize evaluation). CD14 and F4/80 staining can be used to study infiltration of macrophages at the injection site. H&E staining can identify necrosis. Ascites fluid can be tested for immunogenicity of IP injected adenovirus as before. Cytokine ELISA kit (Thermo Scientific) can detect innate immune response. Antibodies to Ad (adaptive immune response) will be detected by the EasyTiter Mouse IgG kit (Thermo Scientific). Ad will be incubated with ascites fluid and used to infect ovarian cancer cell lines, in order to observe neutralizing antibody formation. Organs (ovary, liver, spleen, lung, heart, brain) are collected for histopathology.

Statistical significance can be determined by one-way ANOVA and a Mann-Whitney/Bonferroni post-test as we have done before for in vivo studies.

TABLE 4

| Injections using 2 doses of adenovirus | Expected Results | Extent of Tumor/Met Regression/Reduction | # of Mice |
|---|---|---|---|
| PBS control | Tumors and mets grow | − | 9 |
| CD-PEG-RGD polymer control | Tumors and mets grow | − | 9 × 2 = 18 |
| CD-PEG-RGD/Ad-p53-BH3 (top 2 p53-BH3 constructs optimized from Aims 1-3) | Tumors regress; no mets | ++++ | 9 × 2 = 18<br>9 × 2 = 18 |
| CD-PEG/Ad-p53-BH3 top 2 p53-BH3 constructs (no RGD) | Some tumor regression and met reduction; less due to no tumor targeting with RGD | ++ | 9 × 2 = 18<br>9 × 2 = 18 |
| CD-PEG-RGD/Ad-wt-p53 | Some tumor regression and met reduction | + | 9 × 2 = 18 |

Benchmarks/Expected Outcomes and Alternative Strategies for Aim 3: Several $p^{53}$-BH3 constructs are expected to induce highest apoptosis in vitro in ID8 cells (greater than wt p53 and negative controls); the highest apoptosis-inducing construct can be used in animal studies. Expected in vivo results are in Table 4; optimized p53-BH3 should reduce tumor size and metastases better that wt-p53, and controls. 500 Da PEG can be used for conjugation to improve transfection (may be more toxic); 1% conjugation ratio can be used instead of 0.3%.

Many patients who respond favorably to chemotherapy eventually develop drug-resistance. The poor prognosis of ovarian cancer and the recurrence of drug-resistant HGSC have been linked to expression of anti-apoptotic factors of the Bcl-2 family. In the future, we will test the efficacy of our constructs in drug-resistant patient samples. Combination of our novel p53-BH3 with other drugs is another intriguing possibility, as the gene therapy should amplify other cell death mechanisms. Finally, p53-BH3 can be used for other cancers such as small cell lung cancer (SCLC) or Hepatitis B Virus (HBV)-positive liver cancer. p53 mutation and cancer recurrence with a chemo-resistant phenotype are also characteristics of small cell lung cancer (SCLC). In HBV-positive hepatocellular carcinoma, HBV viral mRNAs have been shown to upregulate Bcl-2 expression and promoter cancer cell survival. Like ovarian cancer, these cancers may benefit most from our novel gene therapy. If successful, the most potent p53-BH3 constructs would represent a true "sledgehammer" for cancer therapy, regardless of p53 status or other genetic heterogeneity. Alternatively, having an assortment of different p53-BH3 constructs could provide "personalization" of cancer therapy, depending on the anti-apoptotic proteins in a given cancer cell type.

Summary: As there been no improvement in treatment for ovarian cancer in the last 40 years, our novel p53-BH3 gene therapy may represent a first step to solve the complexity of ovarian cancer treatment by targeting the key driver of high-grade serous ovarian cancer-p53 mutation, and the problem of drug resistance (through mitochondrial priming). The goal is to advance p53-Bad gene therapy to clinical trials. delivery of the disclosed p53-BH3 gene therapy directly at the disease site (IP cavity) at the time of, and following debulking surgery, to not only eradicate the primary tumor, but to prevent metastasis as well. Good efficacy of p53-BH3 against advanced/recurrent HGSC ovarian cancer, offers a viable treatment against this disease.

B. Example 2

Materials and Methods

Cell Culture and Transient Transfection

All cell lines were grown as monolayers in their respective media. SKOV-3 human ovarian adenocarcinoma cells and ID8 murine ovarian carcinoma cells were grown in DMEM with 10% FBS (for SKOV-3) or 5% FBS (for ID8), supplemented with 1% penicillin-streptomycin (P/S) (Thermo Scientific; Waltham, Mass.), and 1% L-glutamine (Thermo Scientific). ID8 cells were also supplemented with insulin-transferrin-selenium (ITS-X) (Thermo Scientific). Kuramochi cells (JCRB Cell Bank, Japan) and OVCAR-3 human ovarian adenocarcinoma cells (ATCC; Manassas, Va.) were grown in RPMI with 10% FBS (for Kuramochi) or 20% FBS (for OVCAR-3) and were also supplemented with 1% P/S and 1% L-glutamine. OVCAR-3 cells were supplemented with 0.01 mg/mL bovine insulin (Sigma; St. Louis, Mo.). For transfection, $2 \times 10^5$ cells for SKOV-3, $1.5 \times 10^5$ cells for ID8, and $3.0 \times 10^5$ cells for OVCAR-3 and Kuramochi were seeded in 6-well plates (Corning Life Sciences, Tewksbury, MA) or 2-well live cell chambers. The numbers of cells were optimized to account for the different cell growth rates. 24 hr after seeding, the cells were transfected using JetPrime Reagent (PolyPlus Transfection; Illirch, France) with 1 pmol of DNA per well according to manufacturer's recommendation.

Plasmid Constructs

Human Bad cDNA (Sino Biological; Beijing, China) was cloned using primers 5'-GATCCGGTACCATGTCCA-GATCCCAGAG-3' and 5'-ATGTCGGATCCTCACTGG-GAGGGGGCGG-3'. Bad was inserted into the previously cloned pCMV-EGFP-p53 and pCMV-EGFP plasmids using BamHI and KpnI restriction sites (New England Biolabs; Ipswich, Mass.). S112A and S136A site-directed mutagenesis was performed using primers 5'-GGAGTCGC-CACAGCGCATACCCCGCGGGGACGG-3' and 5'-CCGTCCCCGCGGGGTATGCGCTGTGGCGACTCC-3' (for S112A), or 5'-GCCGCTCGCGCGCAGCGCCCCC-CAACC-3' and 5'-GGTTGGGGGGCGCTGCGCGCGAGCGGC-3' (for S136A). Primers 5'-GAGCTCCGGAG-GATGGCTGACGAGTTTGTGGAC-3' and 5'-GTC-CACAAACTCGTCAGCCATCCTCCGGAGCTC-3' were used to generate S155A Bad mutation. Primers 5'-CAGCGCTATGGCCGCGAGGACTCCTT-TAAGAAGGGAC-3' and 5'-GTCCCTTCT-TAAAGGAGTCCTCGCGGCCATAGCGCTG-3' were used to delete the BH3 domain. The sequences of all gene constructs were confirmed by sequencing (Genewiz, South Plainfield, N.J.). All constructs have an EGFP tag on the N-terminus. The p53-Bad constructs used in the experiments were: p53-Bad, p53-Bad/112,136 (double mutant p53-Bad), p53-Bad/112,136,155 (triple mutant p53-Bad), p53-Bad/112,136-ΔBH3 (double mutant p53-Bad with deleted BH3 domain), and p53-Bad-ΔBH3 (p53-Bad with deleted BH3 domain). The following negative controls were included: p53-wt, enhanced green fluorescent protein (EGFP), Bad, Bad/112,136 (double mutant Bad), Bad/112,136,155 (triple mutant Bad), Bad/112,136-ΔBH3 (double mutant Bad with deleted BH3 domain), and Bad-ΔBH3 (Bad with deleted BH3 domain).

Mitochondrial Staining, Microscopy, and Image Analysis 24 hr post-transfection, cells were stained in PBS solution containing 200 nM MitoTracker Red CM-H2Xros (Thermo Scientific), 1:100 dilution of ProLong Live Antifade Reagent (Thermo Scientific), and 2 µM Hoechst stain. The cells were incubated for 20 minutes protected from light. Images were acquired using a Nikon AIR fluorescence confocal microscope with 60× Plan Apo Oil immersion objective (core facility, University of Utah). The images were visualized using NIS element software with built in EGFP, MitoTracker Red, and DAPI filters. Co-localization analyses were performed using the JACoP plugin for ImageJ software. Pearson's correlation coefficient (PCC) values were generated with post Costes' automatic threshold algorithm as before. The PCC values, ranging from −1 to +1, takes into account both the pixel intensity and the signal overlap of EGFP and MitoTracker Red. A PCC value of −1 indicates anti-correlation, and a PCC value of 0 indicates random distribution. A PCC value of +1 indicates complete colocalization, and a PCC value equal to 0.6 or higher is defined to be co-localized by Bolte and Cordeliéres. The experiments were performed three times with 10 cells analyzed each experiment for a total of 30 cells per gene constructs.

Luciferase Reporter Gene Assay

All constructs (3.5 µg of DNA) were co-transfected with 3.5 µg of p53-Luc Cis-reporter plasmid encoding a firefly luciferase gene (Agilent Technologies; Santa Clara, Calif.) and 0.35 µg of pRL-SV40 plasmid encoding a Renilla luciferase gene (Promega; Madison, Wis.). Renilla luciferase was used to normalize for transfection efficiency in respective cell lines. The Dual-Glo Luciferase Assay System (Promega) was used to determine the firefly luciferase activity and Renilla luciferase activity per manufacturer's recommendation 24 hr post-transfection as before. The luminescence signal was detected using the Infinite M1000 microplate reader (Tecan; Männedorf, Switzerland). The Dual-Glo luciferase assay was performed in triplicate.

TMRE Assay 24 hr post-transfection, cells were pelleted and resuspended in 300 µL of annexin-V binding buffer with 100 nM tetramethylrhodamine ethyl ester (TMRE) (Invitrogen; Carlsbad, Calif.). Cells were incubated for 30 minutes at 37° C. then analyzed using flow cytometry (FACS-Canto-II with FACS Diva software, core facility, University of Utah) as described before. EGFP was excited at 488 nm with emission filter 530/35, and TMRE was excited at 561 nm with emission filter 585/15. The loss in TMRE intensity indicates mitochondrial depolarization, which correlates with an increase in the permeabilization of the mitochondrial outer membrane (MOMP). Each construct was transfected independently and tested in triplicates (n=3). The lowest MOMP value was set as 0%, and the highest MOMP value as 100% as before.

Caspase 3/7 Assay

After pelleting, the cells were suspended in diluted fluorescence inhibitor probe FLICA 660-DEVD-FMK (ImmunoChemistry Technologies; Bloomington, Minn.) in PBS according to the manufacturer's instructions. Samples were incubated at 37° C. for 1 hr. The cells were washed 3 times in apoptosis wash buffer and resuspended in 300 µL apoptosis wash buffer. Samples were analyzed using flow cytometry with FACS-Canto-II machine similar to TMRE assay. To detect active caspase 3/7, cells were analyzed for FLICA 660 fluorescence (excited at 660 nm, and detected at 690 nm). The cells were also gated for morphology and EGFP-positive population as before (14). Each experiment was performed in triplicate, and the lowest value and the highest value (for both EGFP and caspase 3/7 positive) were set at 0% and 100%, respectively.

7-AAD Assay

7-AAD assay was performed as before (14, 15). Briefly, the cells were collected 24 hr post-transfection. The cell pellets were resuspended in 300 µL of 1.25 µg/mL 7-AAD in PBS. The cells were incubated on ice for 20 minutes, and analyzed using FACS-Canto-II similar to the TMRE assay. The cells were gated for EGFP positive (excitation at 480 nm and emission at 535 nm) and 7-AAD positive (excitation at 496 nm and emission at 785 nm). The constructs were assayed in triplicates. The lowest and highest values were set at 0% and 100%, respectively (relative 7-AAD) as before (14).

Paclitaxel Treatment

Paclitaxel powder (LC Laboratories; Wobum, Mass.) was dissolved in DMSO to 10 mg/mL to make a stock solution. To determine the paclitaxel IC50 in Kuramochi cells, $8 \times 10^3$ Kuramochi cells were seeded in 96-well plates 24 hr prior to drug treatment. Paclitaxel in complete growth medium was added at increasing concentrations, and the cells were incubated for 48 hr. The Aqueous One Cell Proliferation Assay (Promega) was used to assess cell viability. For gene transfection and paclitaxel combination treatment, the cells were transfected first. 4 hr after transfection, paclitaxel was added at 100 nM or 200 nM, and the cells were incubated for 48 hr as previously optimized by our lab.

Statistical Analysis

All experiments and assays were performed in triplicate unless indicated otherwise. One-way ANOVA with Tukey's post-hoc test was applied to determine statistical significance using Prism GraphPad 6 software, with *p<0.05, p<0.01, *p<0.001, and ns=not significantly different.

Results

SKOV-3, OVCAR-3, ID8, and Kuramochi were chosen for this study for the following reasons. They represent different types of p53 mutations, which are found in >96% of all high grade serous carcinoma (HGSC) cases (11). SKOV-3 (human ovarian adenocarcinoma) and ID8 (murine ovarian carcinoma) both have p53 null status. For SKOV-3, p53- with H179R gene is present but not expressed, while ID8 contains wild type p53 but is also not expressed (31, 32). SKOV-3 is also known for its high Mcl-1 expression from a survey of the anti-apoptotic Bcl-2 family expression (33). Mouse ID8 cell line was included because a syngeneic orthotopic animal model using ID8 cells have been shown to closely mimic human ovarian cancer progression. The ID8 model has all three characteristics of human ovarian cancer, including primary tumor formation, intraperitoneal metastases, and ascites fluid buildup. In addition to its dominant negative R248Q p53 mutation, OVCAR-3 is also known for its resistance to many small molecule BH3-mimetics. Kuramochi has D281Y p53 mutation that causes endogenous p53 to aggregate (structural mutation). Genomic and gene expression profile analyses of multiple ovarian cancer cell lines highlighted Kuramochi as the most representative cell line for HGSC.

Mitochondrial Localization of p53-Bad Chimeric Constructs in SKOV-3 Cells

The chimeric constructs were first tested for their ability to localize to the mitochondria. All of our constructs were tagged with EGFP at the N-terminus to track the localization of the transfected constructs inside the cells. The mitochondria were visualized with MitoTracker Red. Since the mitochondrial localization of Bad is controlled by phosphorylation, S112A and S136A mutations were generated to prevent phosphorylation. Therefore, Bad/112,136 is expected to constitutively localize to the mitochondria, while wild type Bad (without mutations) should remain in the cytoplasm. The ability of Bad and Bad/112,136 to deliver p53 to the mitochondria was tested. Since p53 is known to have 3 nuclear import signals, if Bad/112,136 is able to overcome the nuclear import signals of p53 was determined. p53-wt and EGFP were included as controls for our experiment.

Figures 14A, 14B:
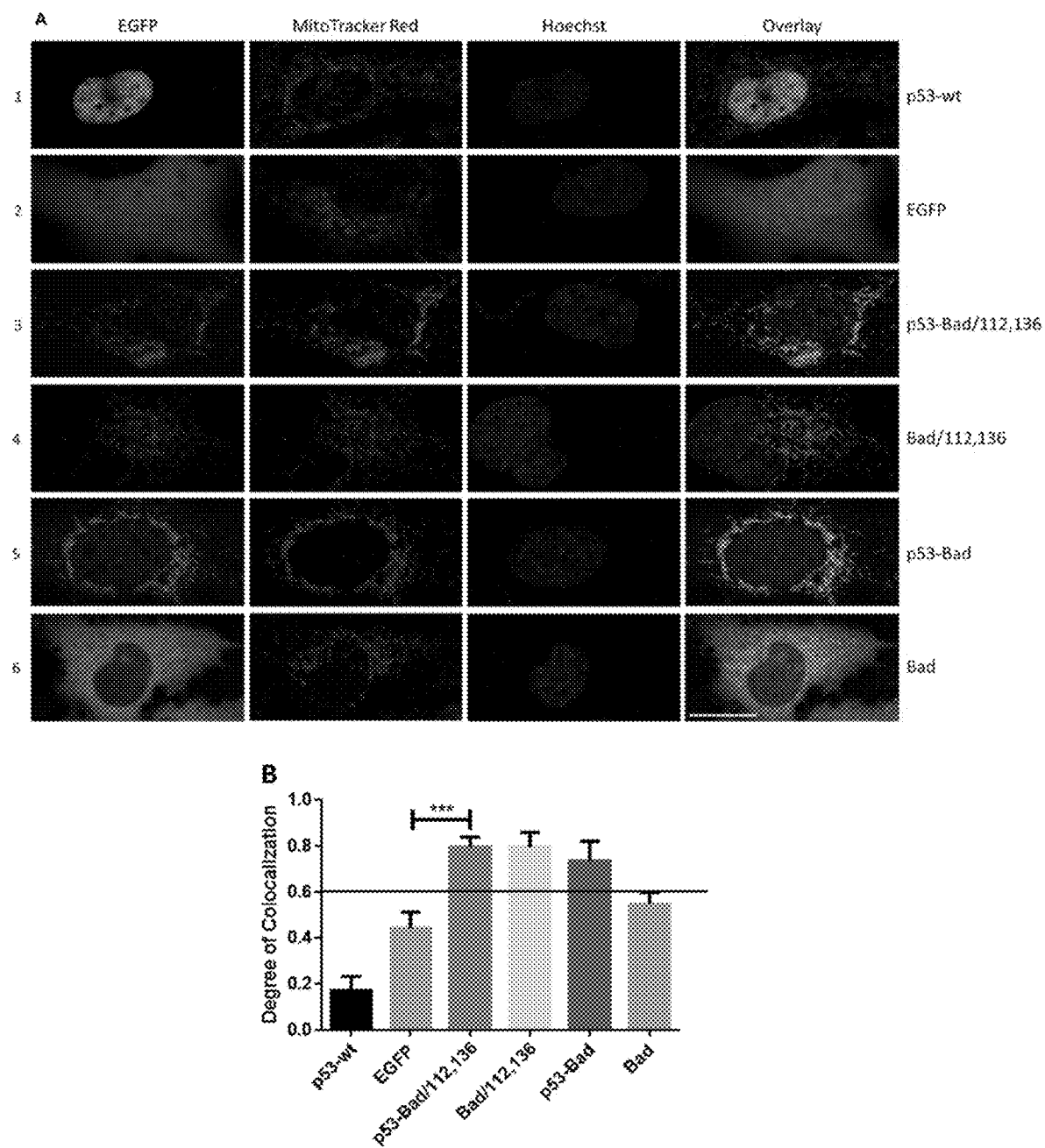
FIGS. 14A and 14B show Mitochondrial localization of p53-Bad chimeric constructs in SKOV-3 cells. (A) Microscopy of EGFP tagged p53-wt, EGFP, p53-Bad/112,136, Bad/112,136, p53-Bad, and Bad/112,136 constructs in SKOV-3 cells. The first column (green color) shows the EGFP tagged constructs, and the second column (red color) shows stained mitochondria. The third column shows the nuclear Hoechst stain, while the last column shows the overlay channel. White scale bar is 20 μm. (B) PCC values were generated for 30 cells from each construct and graphed. A PCC value equals to or greater than 0.6 is considered to be co-localized. Statistical analysis was performed using one-way ANOVA with Tukey's post-test; ***p<0.001. Error bars represent standard deviations (n=30).

When SKOV-3 cells were transfected with p53-wt, exogenous p53-wt mostly localizes to the nucleus and no detectable p53-wt localizes to the mitochondria (FIG. 14A, row 1). The EGFP control diffuses throughout the cells (FIG. 14A, row 2). In contrast, p53-Bad/112,136 and Bad/112,136 effectively localize to the mitochondria (FIG. 14A, rows 3 and 4, overlay column) with a clear EGFP signal overlap with MitoTracker Red (yellow/orange color). On the other hand, p53-Bad (without mutations) only partially localizes to the mitochondria. We can still see a faint EGFP signal inside the nucleus. This result likely comes from a competition between the nuclear import signal from p53 and the mitochondrial localizing tendency of unphosphorylated Bad. The results also suggest that mutant Bad/112,136 can override the nuclear import signals of p53 (FIG. 14A, row 3 and 4).

Bad (negative control) is found in the cytoplasm as expected. To obtain a quantitative comparison of the co-localization, we generated Pearson's correlation coefficient (PCC) values for each individual construct. The PCC values are illustrated in FIG. 14B. A value of 0.6 and above is considered co-localized. Thus, only p53-Bad/112,136, Bad/112,136, and p53-Bad localize to the mitochondria (FIG. 14B, bar 3 to 5). The PCC values of p53-wt, EGFP, and Bad are less than 0.6 and indicate a random distribution.

SKOV-3 was chosen for microscopy and imaging because there were still enough intact cells for visualization of the cell compartments. Due to the potency of the constructs, there is a narrow window for imaging which balances sufficient transfection of the construct vs. cell death/detachment. Cell membrane integrity must be maintained for visualization. For the other cell lines, cell detachment occurred too quickly making imaging untenable. Most transfected cells underwent apoptosis in less than 24 hr, so only cells with relatively low EGFP intensity were able to be visualized. Even so, we can clearly see the fragmentation of the mitochondrial network, a characteristic of apoptosis, in p53-Bad/112,136 transfected cells (FIG. 14A, row 3).

The Activity of Chimeric p53-Bad and p53-Bad/112,136 is Transcriptionally Independent Endogenous wild type p53 functions mainly as a transcriptional factor that exerts its tumor suppression activity through activating many genes involved in the cell cycle, DNA repair, and apoptosis. To validate that the apoptotic activities of our gene constructs are not due to the transcriptional activity of p53, the nuclear transcriptional activity assay was performed. Each test construct was co-transfected with a firefly luciferase gene under the control of a synthetic promoter, which consists of repeats of the transcription recognition consensus sequence of p53 $(TGCCTGGACTTGCCTGG)_{14}$. Both p53-Bad/112,136 and p53-Bad do not have nuclear activity (FIG. 16A to 16D, bar 3 and 5). Even though some p53-Bad (without S112A and S136A mutation) still localizes to the nucleus (FIG. 14A, row 5), p53-Bad does not have transcriptional activity (no significant difference compared to p53-Bad/112,136) as shown in FIG. 15A-D ($5^{th}$ bar in each).

Only p53-wt, the positive control of the assay, has high transcriptional activity (FIG. 15, $1^{st}$ bar). All the negative controls in the assay (EGFP, Bad/112,136, and Bad) do not activate firefly luciferase, as expected (FIG. 16, bars 2, 4, and 6, respectively). An experimental control group with only the reporter gene was included to confirm that the luminescence signal was not due to the activity of endogenous p53. SKOV-3 and ID8 do not express endogenous p53. Both Kuramochi and OVAR-3 have dominant negative p53 statuses. Kuramochi has a D281Y p53 mutation that is known to cause structural aggregation. OVCAR-3 has the R248Q p53 mutation (DNA contact mutant) that prevents proper interaction of p53 to its target genes. p53-Luc control group shows no nuclear activity, indicating that all four cell lines in our study do not have endogenous transcriptional activity for p53. The results from the transcriptional activity assay in combination with the mitochondrial localization analysis (from FIG. 14) confirm that the apoptotic activities of our p53-Bad constructs are transcriptionally independent.

Figures 15A, 15B, 15C, 15D:
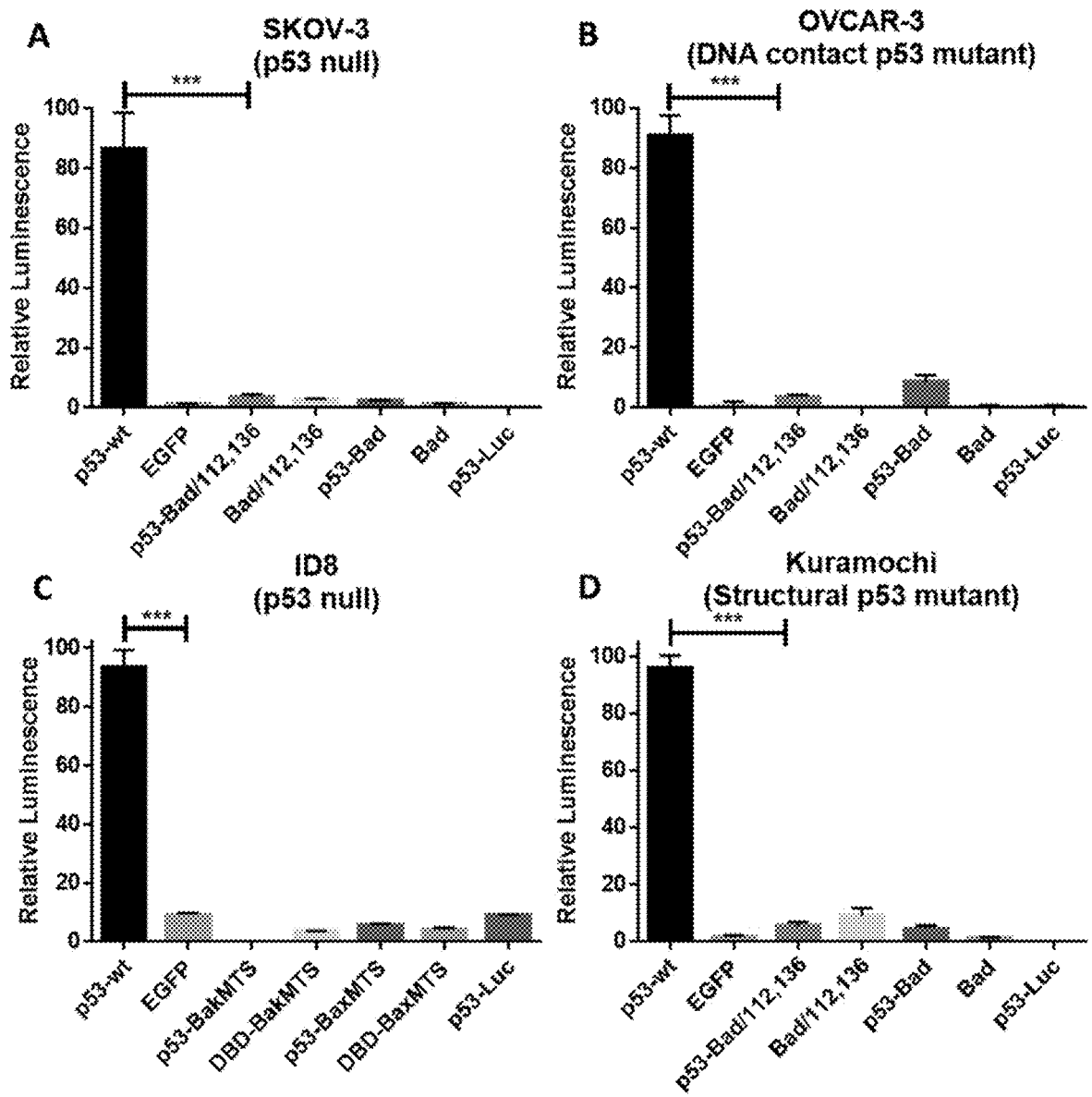
FIGS. 15A-15D. Nuclear transcriptional activity p53 reporter gene assay. p53-Bad constructs were tested for their ability to activate p53-Luc Cis-Reporter in ovarian cancer cell lines with varying p53 statuses. p53-wt was used as the positive control. EGFP, Bad/112,136, and Bad were negative controls. p53-Luc group only has the reporter gene transfected and serves as the negative experimental control. Error bars represent standard deviations from triplicates (n=3). ***p<0.001.

It should be noted that even though OVCAR-3 and Kuramochi have dominant negative p53 statuses, when p53-wt is expressed using a strong promoter (such as the CMV promoter), the overexpressed p53 can overcome the dominant negative effect. In this case, there is still a strong luminescence signal from p53-wt in OVCAR-3 and Kuramochi cells (FIGS. 15B and 15D, $1^{st}$ bar)

p53-Bad and p53-Bad/112,136 Induce Late Stage Cell Death

After confirming the mitochondrial localization of p53-Bad/112,136 and p53-Bad to the mitochondria and lack of nuclear activity, we tested the ability of the chimeric constructs to induce late stage apoptosis and cell death. 7-AAD assay utilizes 7-aminoactinomycin, a DNA intercalating dye that only penetrates and stains cells with disrupted and permeable membranes. 7-AAD reagent is not capable of penetrating living cells with an intact cell membrane.

Figures 16A, 16B, 16C, 16D:
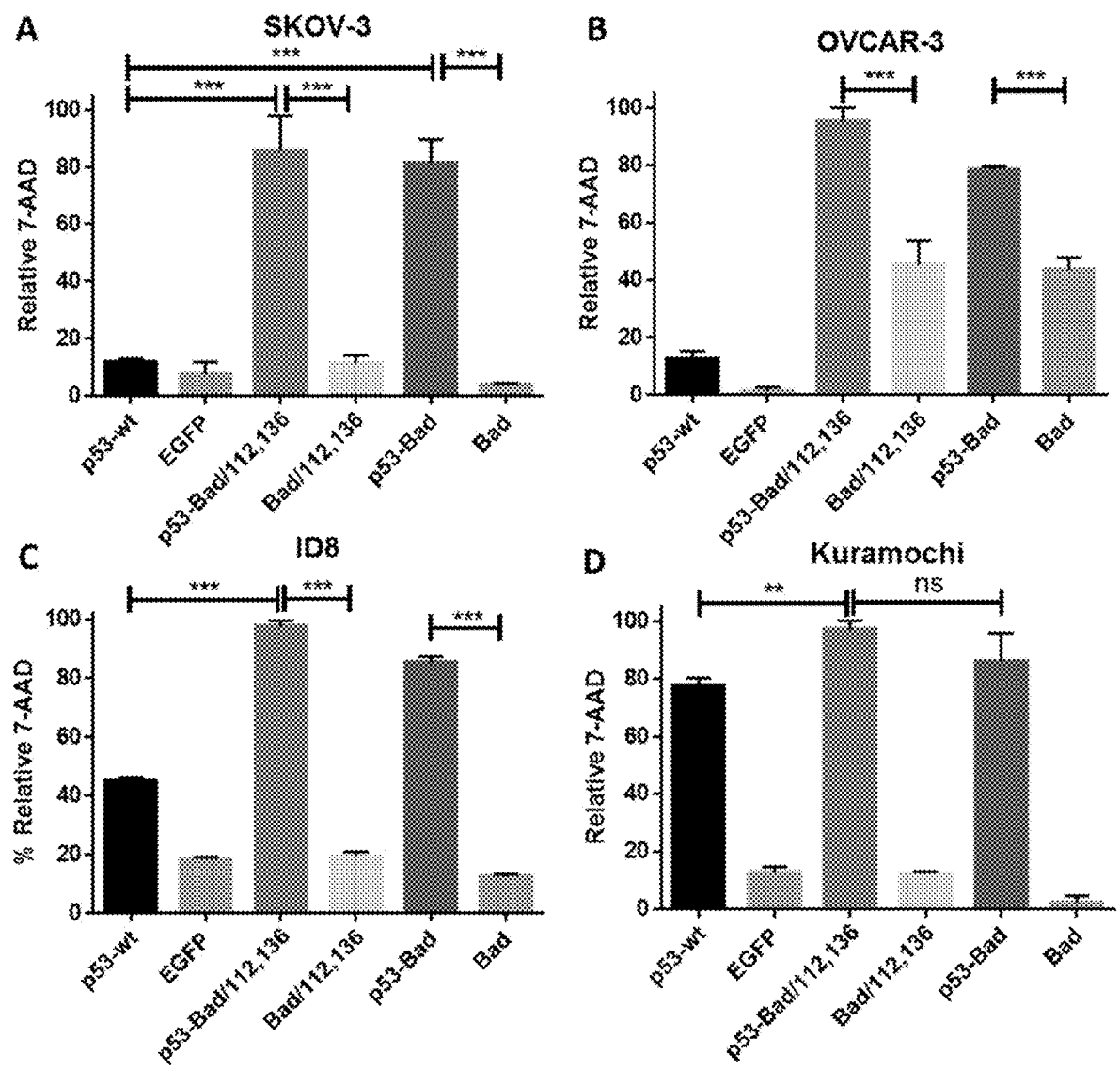
FIGS. 16A-16D. 7-AAD cell death assay in 4 ovarian cancer cell lines with different p53 statuses (24 hr post-transfection). The assay was conducted 24 hr post-transfection. Statistical analysis was performed using one-way ANOVA with Tukey's post-test (ns means no significance, p<0.01, *p<0.001). Error bars represent standard deviations from 3 triplicates (n=3).

In SKOV-3 cells, p53-Bad/112,136 has superior activity over p53-wt and Bad/112,136 alone (FIG. 16A, compare $3^{rd}$, $1^{st}$, and $4^{th}$ bars, respectively). Even without the Bad mutation and only partial mitochondrial localization, p53-Bad still efficiently induces late apoptosis and cell death, and there is no significant difference compared to the killing activity of p53-Bad/112,136 in this cell line (FIG. 16A, compare $3^{rd}$ and $5^{th}$ bars). In all four cell lines, p53-Bad/112,136 and p53-Bad have superior activity over all other constructs, including the Bad/112,136 mutant. EGFP was included in all studies for comparison.

Bad/112,136 with S112A and S136A mutations cannot be phosphorylated and localizes to the mitochondria. Therefore, Bad/112,136 is expected to have a higher capability to neutralize anti-apoptotic factors than Bad (without mutations). However, the apoptotic activities of Bad/112,136 and Bad are comparable to EGFP (negative control) except in OVCAR-3 cells (FIG. 16, bars 4, 6, and 2).

The experiment was performed 24 hr post-transfection. This late apoptosis and cell death assay indicates that p53-Bad constructs are capable of triggering rapid apoptosis and cell death.

p53-Bad Constructs Induce Apoptosis Through the Intrinsic Mitochondrial Pathway

Figures 17A, 17B, 17C, 17D:
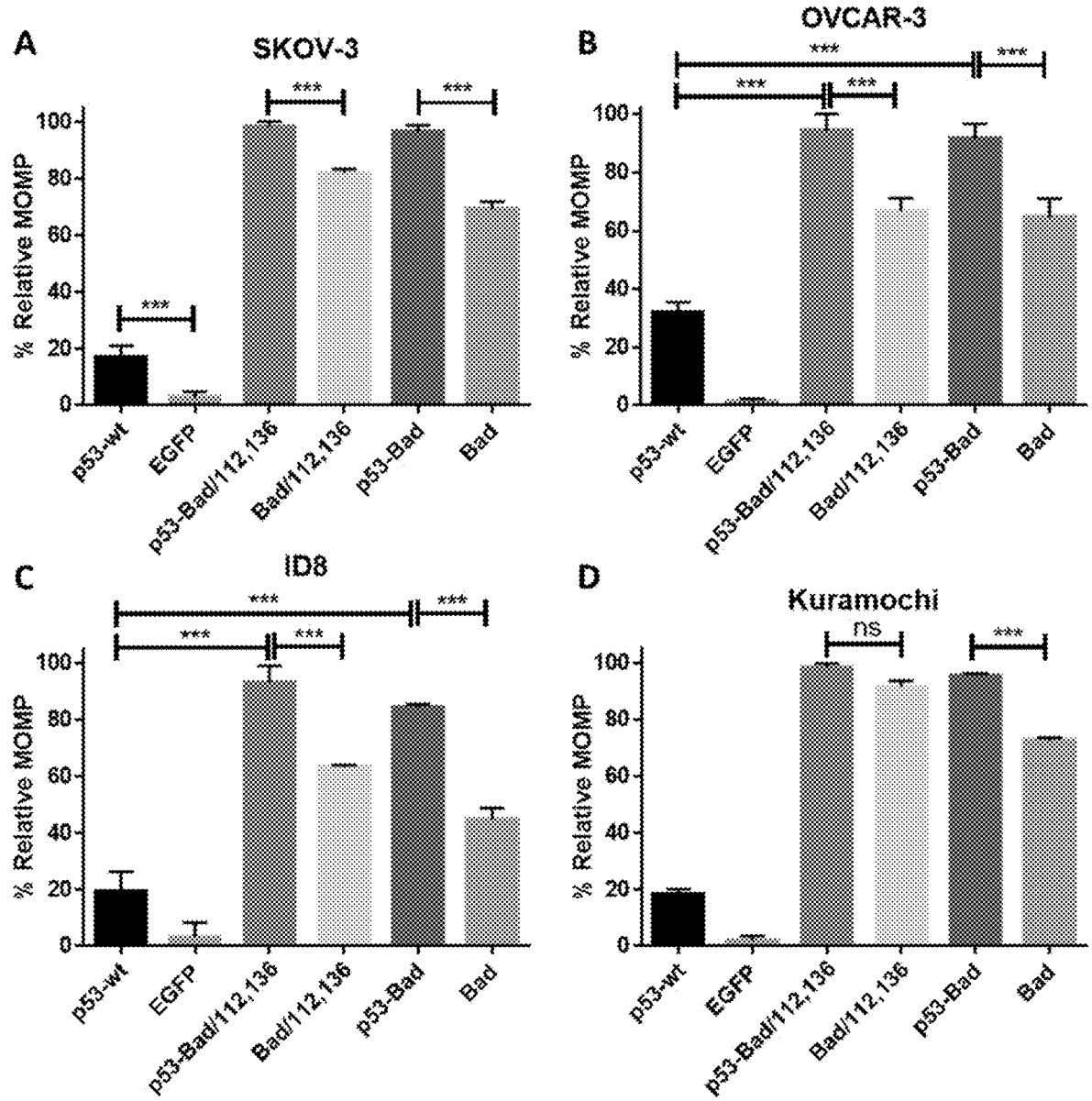
FIGS. 17A-17D. Mitochondrial apoptosis TMRE assay was performed in 4 ovarian cancer cell lines (20 hr post-transfection). Mitochondrial depolarization correlates with an increase in mitochondrial outer membrane permeabilization (MOMP), which is measured by the loss of the TMRE fluorescence intensity. Statistical analysis was performed using one-way ANOVA with Tukey's post-test; ns means no significance, ***p<0.001. Error bars represent standard deviation from three independent experiments (n=3).

Even though there have been multiple attempts by CAR-T cell therapy to trigger extrinsic apoptosis by targeting the cell death receptors such as the FAS receptor (CD95), the potential of the intrinsic apoptosis pathway through the mitochondria has not been fully explored. The intrinsic mitochondrial pathway is characterized by the loss of the mitochondrial membrane potential, mitochondrial outer membrane permeabilization (MOMP), and cytochrome c release, leading to the formation of apoptosome and caspase cascade activation. To confirm that the late stage apoptosis activities of p53-Bad constructs follow the intrinsic mitochondrial pathway, we tested the ability of our constructs to induce mitochondrial outer membrane permeabilization (MOMP). The presence of MOMP marks the first step of mitochondrial apoptosis. When Bak and Bax are released from the anti-apoptotic factors and become activated, they homo-oligomerize to form permeable pores on the mitochondrial outer membrane, which in turn results in the loss of mitochondrial potential. TMRE is a cationic dye that accumulates to mitochondria with active potential. The loss of mitochondrial potential by MOMP can be measured by the loss of TMRE fluorescence intensity by flow cytometry. In SKOV-3, OVCAR-3, and ID8, p53-Bad/112,136 and p53-Bad have the highest % MOMP induction (FIG. 17A-C, bars 3 and 5). The apoptotic activity of p53-Bad/112,136 is higher than p53-wt and the EGFP negative control ($1^{st}$ and $2^{nd}$ bar, respectively). In Kuramochi cells, there is no significant difference between p53-Bad/112,136 and Bad/112,136 as measured by MOMP induction (FIG. 17D, bar 3 and 4). However, there is a significant difference between the two constructs as measured by the 7-AAD late stage cell death assay (FIG. 16D, bar 3 and 4). The results highlight the importance of using multiple assays that detect different stages of apoptosis to have a complete picture of the activity of these constructs. Mitochondrial Bad is capable of neutralizing Bcl-XL and Bcl-2. Therefore, they are expected to suppress the mitochondrial potential and have a higher activity than EGFP as shown in FIG. 17 (compare bars 2, 4 and 6). Even though Bad/112,136 and Bad show a significant level of % MOMP, their apoptotic activity diminishes as measured by later stage apoptosis assay (FIG. 16, bars 4 and 6).

p53-Bad Constructs Activate Caspase Cascade and Commit Cells to Mitochondrial Apoptosis There are two major hallmarks of mitochondrial apoptosis: MOMP and caspase activation. After Bak and Bax form permeable pores on the mitochondrial membrane, cytochrome c is released and binds to Apaf-1 to form the apoptosome and trigger the caspase cascade. Therefore, we next tested the ability of our constructs to activate caspase using a caspase 3/7 fluorescent inhibitor probe 660-DEVD-FMK to label active caspase 3/7.

Figures 18A, 18B, 18C, 18D:
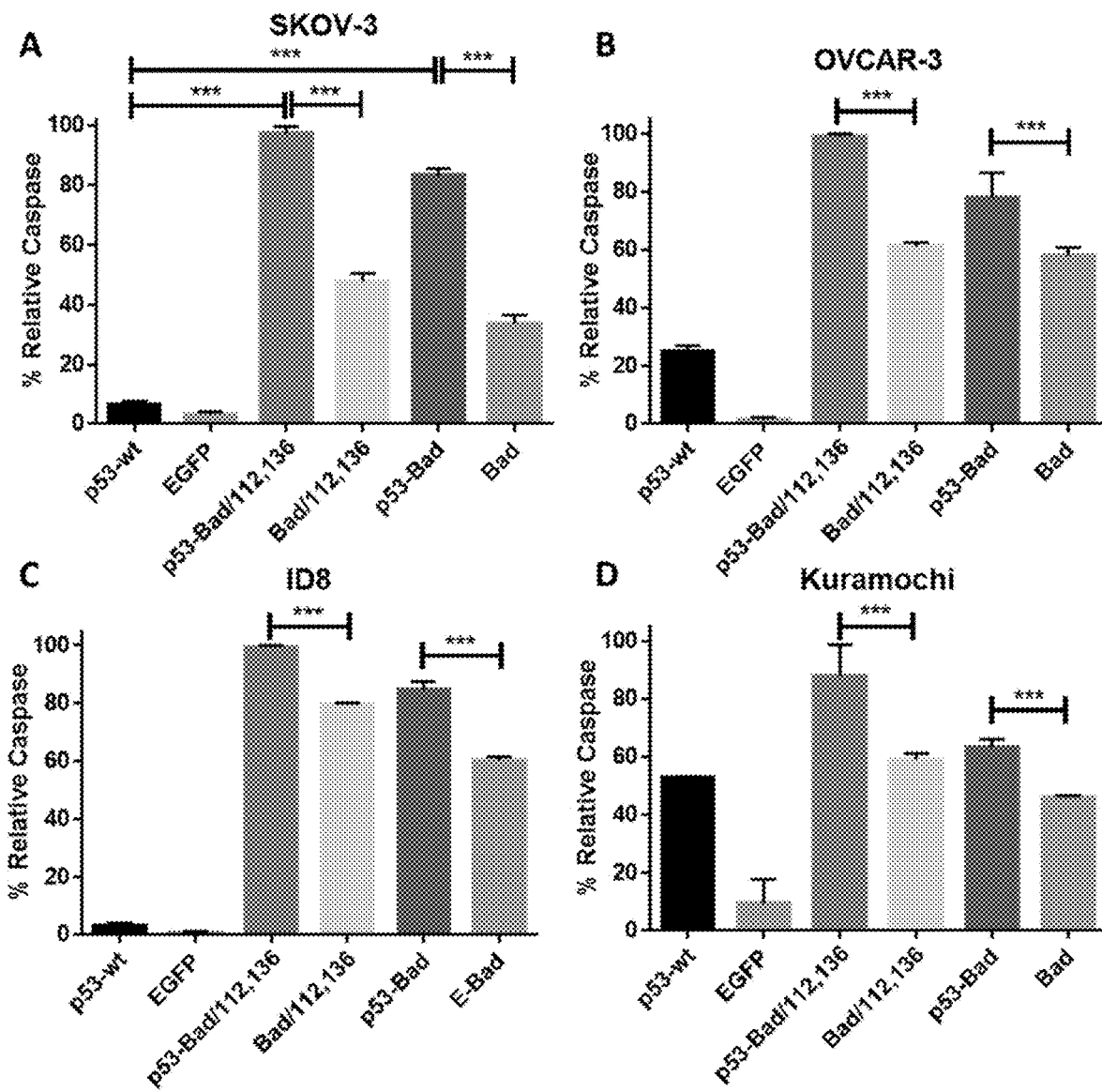
FIGS. 18A-18D. Caspase 3/7 assay was performed 16 hr post-transfection. p53-Bad/112,136 has the highest caspase activity compared to all other constructs. Statistical analysis was performed using one-way ANOVA with Tukey's post-test; ***p<0.001. Error bars represent standard deviation from triplicates (n=3).

In this assay, more distinct differences are seen between p53-Bad/112,136 and p53-Bad compared to the other two assays. In this caspase 3/7 assay, p53-Bad/112,136 shows a higher apoptotic activity than p53-Bad without mutations in all four cell lines (FIG. 18, compare bars 3 and 5). p53-Bad/112,136 and p53-Bad also have higher apoptotic activity than their respective negative controls without p53 (FIG. 18, compare bars 3 to 4; bars 5 to 6). p53-Bad/112,136 have superior apoptotic activity over all other constructs. Caspase 3/7 activation and MOMP induction confirm that p53-Bad/112,136 triggers apoptosis through the transcriptionally independent mitochondrial pathway.

S155A does not Enhance the Apoptotic Activity of p53-Bad/112,136

When investigating the primary sequence of Bad for consensus phosphorylation motifs that are potential targets for protein kinases that promote cell survival, another phosphorylation site (serine 155) within the BAD BH3 domain has been identified by Yaffe et al. This S155 is a target for protein kinase A (PKA) and is thought to play an inhibitory role in the interaction of Bad with Bcl-2 and Bcl-XL. Neutralization of anti-apoptotic factors by BH3-only proteins are carried out by the insertion of 4 hydrophobic residues in the BH3 helix to a hydrophobic groove of the anti-apoptotic proteins. When S155 is phosphorylated, the bulky negatively charged phosphate group creates a steric hindrance that prevents the interaction of Bad to Bcl-XL. Bad Ser-155 is highly conserved and provides another way for Bad to be regulated by protein kinases through phosphorylation. Therefore, mutation S155A was generated in the p53-Bad constructs to see if S155A could enhance apoptotic activity.

When Ser-155 is mutated to alanine, the BH3 domain of Bad can never be blocked. p53-Bad/112,136,155 has triple serine to alanine mutations (S112A, S136A, S155A), and Bad/112,136,155 is the negative control (no p53). Constructs with a single S155A mutation were also created for comparison with the double mutants (112,136).

Figures 19A, 19B, 19C, 19D:
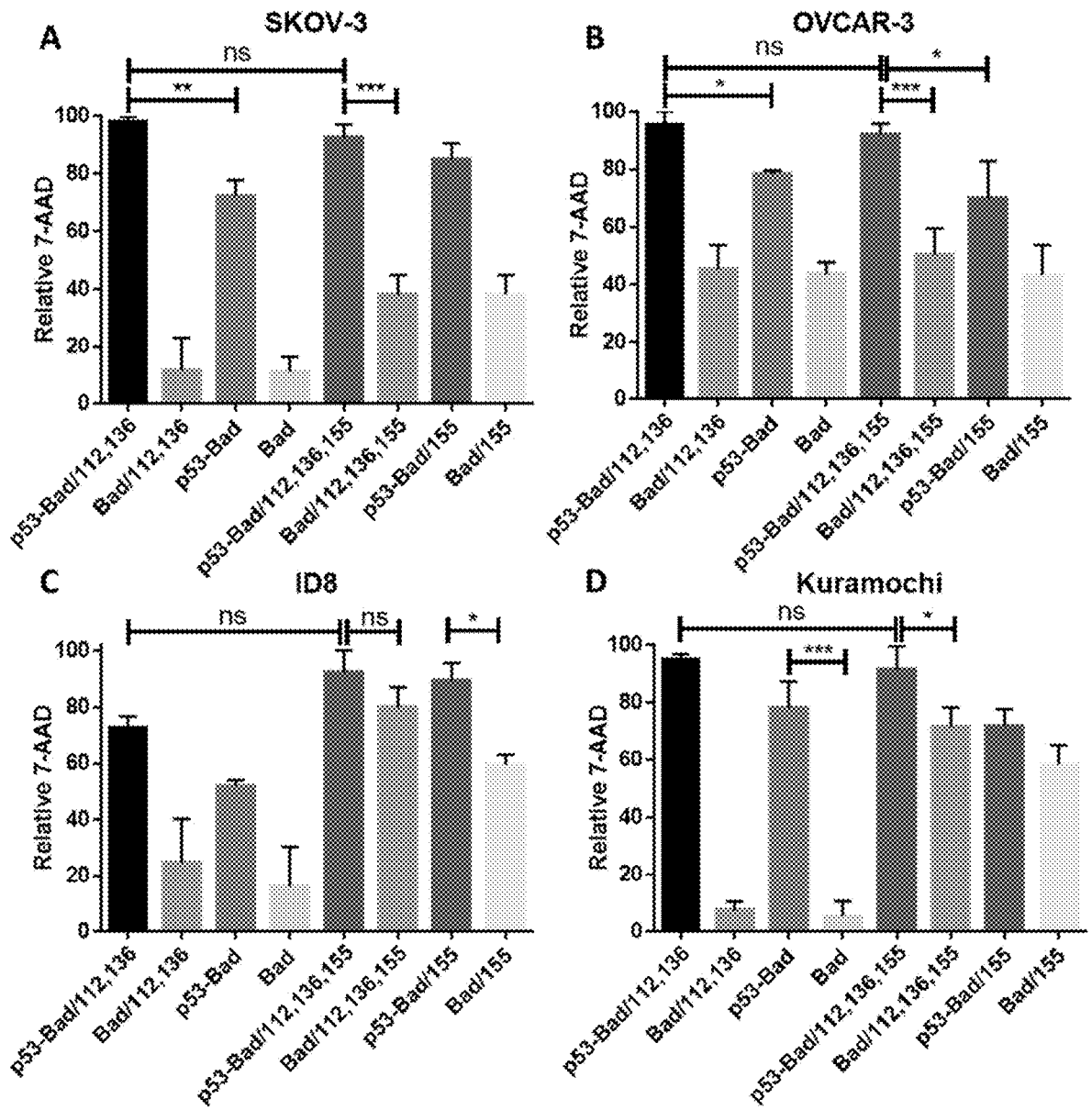
FIGS. 19A-19D. 7-AAD assay was conducted 24 hr post-transfection with triple mutant constructs. Statistical analysis was performed using one-way ANOVA with Tukey's post-test (ns p>0.05, *p<0.05, p<0.01, *p<0.001). Error bars represent standard deviations from triplicates (n=3).

There is no significant difference between the triple mutant p53-Bad/112,136,155 and the double mutant p53-Bad/112,136 in all four ovarian cancer cell lines (FIG. 19A to D, compare bars 1 and 5). In SKOV-3 and ID8 cells, p53-Bad/155 has comparable apoptotic activity to p53-Bad/112,136 (FIGS. 19A and 19C, compare bars 1 and 7), indicating that the S155A may replace the double mutant for a similar activity in these two cell lines. However, this is not the case in OVCAR-3 and Kuramochi since p53-Bad/112,136 has significantly higher activity than p53-Bad/155 (FIG. 19B, compare bars 1 and 7). Regardless, p53-Bad/112,136 is just as effective as p53-Bad/112,136,155, and there is no extra benefit for the chimeric triple mutant.

In ID8 and Kuramochi cells, Bad/112,136,155 and Bad/155 have significantly higher apoptotic activity than Bad/112,136 and wild type Bad (FIGS. 19C and 19D, compare bars 6 and 8 to 2 and 4), suggesting the importance of S155 in regulating the interaction between Bad and Bcl-XL. S155A mutation encourages the binding and neutralization of Bcl-2, Bcl-W, and Bcl-XL by Bad once it localizes to the mitochondria. The apoptotic activities of Bad/112,136,155 and Bad/155 are lowered in SKOV-3 and OVCAR-3 (compared to ID8 and Kuramochi) (FIGS. 19A and 19B, compare bars 6 and 8 to 2 and 4). There is no significant difference between all negative control Bad constructs (wide type, single, double, and triple mutant) in OVCAR-3 cells. The phenomenon is likely due to the high expression of Mcl-1 in SKOV-3 and OVCAR-3 cell lines.

BH3 Domain of Bad is Required for the High Apoptotic Activity of p53-Bad Constructs To determine how much the BH3 domain contributes to activity of the p53-Bad constructs, the core of the BH3 domain (9 amino acid residues LRRMSDEFV) of Bad was deleted. This BH3 domain of pro-apoptotic factor Bad is responsible for the interaction of Bad to the anti-apoptotic factors Bcl-2, Bcl-xL, and Bcl-W. The activity of the deleted BH3 constructs were tested versus the full-length versions in OVCAR-3 cells. OVCAR-3 has been known to be highly resistant to small molecule BH3 mimetic treatment due to its high expression of both Bcl-XL and Mcl-1. These small molecule drugs can only inhibit Bcl-2, Bcl-XL, and Bcl-W, so in a sense they are similar to Bad. The IC50 for ABT-737 and ABT199 (venetoclax) in OVCAR-3 cells are 10±4 (µM) and 15±5 (µM), respectively. The IC50 of these BH3 mimetics in OVCAR-3 cells are well beyond the clinically achievable concentration (less than 2 µM).

TMRE assay was used to test these constructs for their ability to trigger MOMP. Deletion of the BH3 domain significantly reduces the activity of Bad/112,136 (FIG. 20, compare bars 4 and 8), likely due to the inability of Bad-ΔBH3 to inhibit Bcl-2, Bcl-XL, and Bcl-W.

Figure 20:
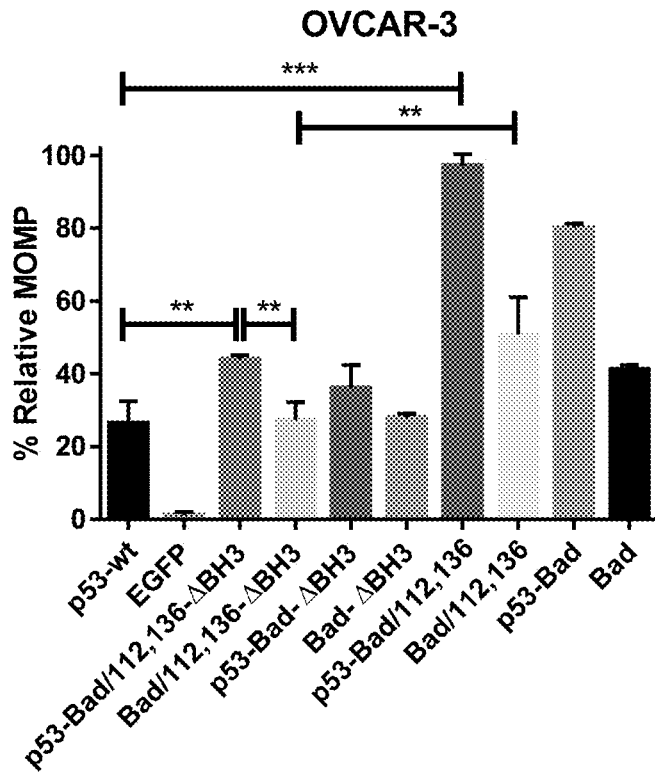
FIG. 20 shows TMRE assay in OVCAR-3 to test the activity of p53-Bad constructs with deleted BH3 domain (20 hr post-transfection). Bad-ΔBH3 and Bad/112,136-ΔBH3 were included as negative controls. Statistical analysis was performed using one-way ANOVA with Tukey's post-test; p<0.01, *p<0.001. Error bars represent standard deviations from triplicates (n=3).

When the BH3 domain is deleted, p53-Bad/112,136-ΔBH3 still has higher activity than Bad/112,136-ΔBH3 (FIG. 20, compare bar 3 to bar 1 and 4). The result indicates that mitochondrial p53 still retains its ability to inhibit anti-apoptotic proteins and activate Bak and Bax. Mitochondrial p53 also induces MOMP more efficiently than p53-wt (FIG. 20, compare bars 1 and 3). p53-Bad/112,136 with functional BH3 is the superior construct with highest MOMP induction (FIG. 20, bar 7).

p53-Bad/112,136 can be Used as Stand-Alone Therapy for Ovarian Cancer Treatment

Figure 21:
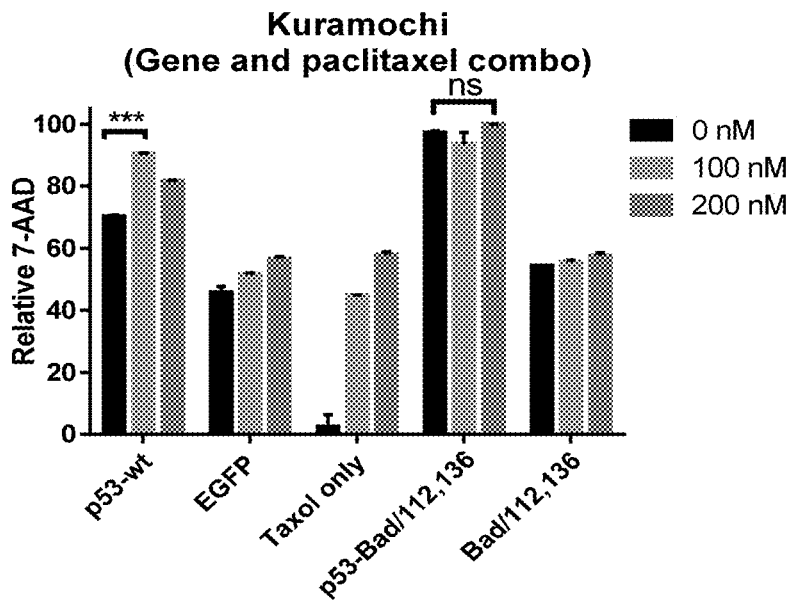
FIG. 21 shows a combination of p53-Bad/112,136 construct with paclitaxel was tested in Kuramochi cells. Paclitaxel was added 4 hr after transfection, and the cells were incubated for 48 hr. 7-AAD assay was performed to determine the efficacy of various combinations. One-way ANOVA with Tukey's post-test was used to determine statistical significance (ns p>0.05, ***p<0.001). Error bars represent standard deviation from triplicates (n=3).

After confirming the high apoptotic potential of p53-Bad/112,136, we wanted to test the possibility of combining p53-Bad/112,136 gene therapy with paclitaxel, a standard-of-care for HGSC. Based on a genomic and gene expression profile study with 47 ovarian cancer cell lines, Kuramochi was identified to be the best model for high grade serous ovarian cancer, with the highest genetic similarity to ovarian tumors. The IC50 of paclitaxel was determined using a cell viability MTT assay. Kuramochi cells were incubated with different paclitaxel concentrations ranging from 0 nM to 1000 nM for 48 hr. The IC50 value was determined to be approximately 100 nM. This value is consistent with the reported IC50 ranges for ovarian cancer cell lines. p53-Bad/112,136 was used since it has superior apoptotic activity compared to all other constructs we have tested so far. Bad/112,136 was added as the negative control for the assay. p53-wt, EGFP, and paclitaxel treatment only were included for comparison. Each individual construct was transfected for 4 hr before the paclitaxel was added at IC50 (100 nM) or 2×IC50 (200 nM). A control group without paclitaxel (0 nM) was also included. The cells were incubated for 48 hr before the 7-AAD assay. Even though this is not the optimal time point to assay the apoptotic activity of p53-Bad/112, 136 since the construct is fast acting and triggers apoptosis in less than 24 hr (FIG. 16, 17, 18), 48 hr is the earliest time point for paclitaxel to have an effect. In the past, we attempted to pretreat the cells with paclitaxel 24 hr before transfection. However, paclitaxel pretreatment had a negative impact on the gene transfection efficiency. The toxicity of transfection is also more apparent when assayed at this time point (FIG. 21, bar 4). Paclitaxel treatment does not seem to increase the apoptotic potential of the negative control Bad/112,136 as well (FIG. 21, last bars).

In the 7-AAD late apoptosis assay, p53-Bad/112,136 had superior activity over other constructs even without paclitaxel (FIG. 21). Paclitaxel treatment does not increase the activity of p53-Bad/112,136, but paclitaxel treatment at the IC50 concentration (100 nM) may enhance the activity of p53-wt (FIG. 21, compare bars 1 and 2). Nonetheless, p53-Bad/112,136 still induces higher apoptosis than the combination of p53-wt with paclitaxel, suggesting that p53-Bad/112,136 may be effective as a solo therapy. This would be advantageous because the non-specific toxicity of chemotherapy drugs could be avoided.

Discussion

Delivery of drugs and macromolecules to the mitochondria holds great therapeutic promise for many diseases, including cancer. The balance of mitochondrial pro- and anti-apoptotic factors has been implicated in drug resistance. The concept of mitochondrial priming was first introduced by Letai et al. when studying drug resistance in leukemia. The concept refers to the relative expression of pro-apoptotic factors and anti-apoptotic factors of the Bcl-2 family in the mitochondria. Chemo-sensitive tumors have higher levels of pro-apoptotic factors and lower levels of anti-apoptotic factors than their chemo-resistant counterparts. Cancer cells with higher expression of anti-apoptotic factors are more resistant to apoptosis. The important role of the Bcl-2 family has resulted in the development of many BH3 mimetics that can inhibit Bcl-2 and Bcl-XL. ABT-737 and its BH3-mimetic derivatives inhibit Bcl-XL and Bcl-2 and sensitize the cancer cells to apoptosis via Bak and Bax activation. However, there is no single small molecule BH3-mimetic that can target all anti-apoptotic proteins. Overexpression of Mcl-1 is the major resistance mechanism for ABT-737 and venetoclax treatment in many types of cancer. These small molecule drugs also have severe toxicities, which may pose major concerns for patients.

Most ovarian cancer patients do not have strong Bcl-2 expression at the onset of disease, and these patients initially respond favorably to chemotherapy with a 50-70% response rate. However, 88% of patient samples have high Bcl-XL expression when the cancer relapses and becomes drug resistant. These tumors also become more aggressive and resistant to multiple chemotherapy drugs including cisplatin, paclitaxel, topotecan, and gemcitabine. Poor prognosis in high grade serous carcinoma (HGSC), the most aggressive and also the common type of ovarian cancer, is associated with increased Mcl-1 expression.

To overcome these issues, mitochondrially targeted p53 was designed. Mitochondrial p53 can bypass the cell cycle arrest pathway and directly trigger apoptosis. In the past, many different mitochondrial targeting signals (MTS) from various mitochondrial proteins including cytochrome c oxidase (CCO), ornithine transferase (OTC), translocase of the outer membrane (TOM), and Bcl-XL have been explored for their ability to target p53 or its subdomain to the mitochondria for cancer therapy. Both the strength of the MTSs and the specific mitochondrial compartments that the MTSs target can impact the success of such mitochondrial targeting. Because Bcl-2 family proteins locate on the outer membrane of p53, our current efforts are focused on this specific compartment.

We have also shown that the DNA binding domain (DBD) of p53 is the minimally required domain for mitochondrial apoptosis in many cell lines, and that apoptotic activity is diminished when residues required for pro-apoptotic Bak interaction are mutated to alanine (K120, R248, R273, R280, E285, E287). We have also shown that p53 can be effectively targeted to the mitochondria by attaching the mitochondrial targeting signals from the effectors Bak or Bax (BakMTS and BaxMTS) to the C-terminus of p53. While p53-BakMTS and p53-BaxMTS show some promising activities, they do not provide a clear advantage over p53-wt in some cell lines. Therefore, we started to explore different strategies to target p53 to the mitochondria while being able to augment the apoptotic activity of p53.

The p53-Bad and p53-Bad,112,136 constructs described here combine mitochondrial p53 with the mitochondrial priming concept in the form of the BH3-only protein Bad. Mutations S112A and S136A prevent phosphorylation of Bad, and hence improve mitochondrial localization, leading to improved mitochondrial delivery of p53-Bad constructs (FIG. 14); p53-Bad/112,136 and Bad/112,136 efficiently localize to the mitochondria. The results also show that Bad/112,136 can override the 3 nuclear localization signals of p53 (FIG. 14). The Bcl-2 family belongs to a group of tail anchor proteins. While the exact molecular machinery for mitochondrial transport of these tail anchor proteins are not clear, mitochondrial localization strategies for many Bcl-2 family proteins have been elucidated. Bad, for example, localizes to the mitochondria when S112 and S136 are dephosphorylated and released from the scaffold protein 14-3-3. The affinity of lipid binding motifs at the C-terminus of Bad to mitochondrial outer membrane is lost when Bad is associated with 14-3-3, indicating that there may be a conformational change when Bad is phosphorylated or dephosphorylated. The exact relationship between lipid binding dynamics and the accessibility of kinases and phosphatases to serine residues in Bad still needs to be investigated. Bad is one of few Bcl-2 family proteins that do not have a transmembrane domain at the C-terminus. Instead of inserting itself into the mitochondrial outer membrane, Bad is thought to associate with outer membrane. This may allow more flexibility for p53-Bad to interact with other Bcl-2 family proteins at the mitochondria.

p53-Bad constructs increase the reservoir of pro-apoptotic Bad to neutralize Bcl-2, Bcl-XL, and Bcl-W and promote apoptosis. With mitochondrial $p^{53}$'s ability to inhibit Mcl-1 and directly activate effectors Bak and Bax, p53-Bad/112, 136 has multiple mechanisms of action and is capable of inhibiting a wide range of anti-apoptotic factors. The apoptotic activity of p53-Bad/112,136 is transcriptionally independent (FIG. 15). Using three different assays that cover different stages of apoptosis, we were able to confirm that the apoptotic activity of p53-Bad/112,136 is triggered through the intrinsic mitochondrial pathway (FIGS. 16, 17, and 18). TMRE assay measures the degree of MOMP, while caspase 3/7 detects active caspases. 7-AAD examines late stage apoptosis and loss of cell membrane integrity. p53-Bad/112,136 and p53-Bad have superior apoptotic activity over p53 alone or Bad alone as well as the negative control EGFP (FIG. 16, 17, 18). The apoptotic potential of p53-Bad/112,136 is consistent across all three different assays. p53-Bad/112,136 also maintains its high apoptotic activity regardless of the endogenous p53 status of the ovarian cancer cell lines included in this study, and p53-Bad/112,136 can effectively induce apoptosis in cell lines with high Mcl-1 and Bcl-XL expression such as OVCAR-3 and SKOV-3 (FIGS. 16, 17, 18, A and B).

We also attempted a S115A mutation in the Bad BH3 domain. Phosphorylation of Bad Ser-155 is known to abolish the pro-apoptotic ability of Bad by blocking the Bad-Bcl-XL interaction. However, p53-Bad/112,136 is sufficiently potent, rendering S155A unnecessary (FIG. 7). When the Bad BH3 domain is deleted, the apoptotic potential of p53-Bad/112,136 is greatly hampered (FIG. 20), highlighting the importance of the BH3 domain in this chimeric construct. Finally, we tested the combination of our constructs with paclitaxel in Kuramochi cells. Paclitaxel treatment does not enhance the activity of our constructs, suggesting that p53-Bad/112,136 is effective as a stand-alone therapy (FIG. 21).

The study is the first to use pro-apoptotic Bad/112,136 as vehicle to deliver an active protein to mitochondria for therapeutic purposes. In addition to pro-apoptotic Bad, there are many other BH3-only pro-apoptotic proteins that could be utilized as well. Each individual BH3-only pro-apoptotic factor has a different strategy for mitochondrial localization. Utility of these pro-apoptotic factors for mitochondrial delivery has yet to be explored.

Toxicity has been a challenge in cancer gene therapy. Being very efficient at inducing apoptosis, our novel gene constructs can be toxic to normal cells as well. Therefore, it is extremely important to address this problem. We are exploring different strategies to reduce toxicity. One obvious method is to place our novel p53-Bad constructs under control of a cancer specific promoter. Telomerase reactivation is a hallmark of tumorigenesis, and countless reports over the years have shown that human telomerase (hTERT) activity is significantly higher in cancer cells compared to normal cells. Recent work from our lab has shown promising results for three ovarian cancer-specific promoters—hTC, Brms1, and −279/+5—as drivers of p53-Bad/112,136 (unpublished data in review). hTC, a fusion promoter of a section of hTERT and a CMV enhancer element, shows high transfection levels of p53-Bad/112,136, potent apoptotic activity as measured by the TMRE assay, and some cancer specificity (unpublished data). Brms1, the breast cancer metastasis suppressor 1 promoter, shows somewhat lower transfection levels of p53-Bad/112,136 but maintains high apoptotic activity as well as cancer specificity (unpublished data). −279/+5, a section of the hTERT promoter, displays lower transfection levels of p53-Bad/112,136, but at least 2 fold greater cancer-specificity while maintaining high apoptotic activity (unpublished data). Each of these promoters has promise for in vivo p53-Bad/112,136 studies, as fine-tuning the balance between transfection rates and cancer specificity will lead to an effective anti-cancer construct with low toxic side effects.

In addition to a cancer specific promoter, the delivery vector for future in vivo studies can also be tagged or modified with a cancer targeting moiety such as folate or RGD peptides, which have high affinity for integrin receptors. Folate receptor alpha and integrin receptors have been known to be overexpressed in many types of cancer including ovarian carcinoma. One feature of ovarian cancer that can make p53-Bad gene therapy more feasible is intraperitoneal metastases. Ovarian cancer has been known to be localized inside the intraperitoneal cavity. The p53-Bad/112, 136 gene construct to be delivered into the intraperitoneal cavity using a cationic biodegradable polymer or viral vector. Local delivery of the genes can avoid some unwanted toxicity compared to systemic delivery.

As ovarian cancer continues to be the most lethal gynecological malignancy, the p53-Bad/112,136 gene therapy can represent a first step to solve the complexity of ovarian cancer treatment by targeting the key driver of high-grade serous ovarian cancer-p53 mutation- and the problem of drug resistance through mitochondrial priming.

REFERENCES

1. Burrell, R. A., et al., *The causes and consequences of genetic heterogeneity in cancer evolution*. Nature, 2013. 501(7467): p. 338-45.
2. Holohan, C., et al., *Cancer drug resistance: an evolving paradigm*. Nat Rev Cancer, 2013. 13(10): p. 714-26.
3. Turner, N.C. and J. S. Reis-Filho, *Genetic heterogeneity and cancer drug resistance*. Lancet Oncol, 2012. 13(4): p. e178-85.
4. Volm, M. and T. Efferth, *Prediction of Cancer Drug Resistance and Implications for Personalized Medicine*. Front Oncol, 2015. 5: p. 282.
5. Bai, Y. and W. C. Shen, *Improving the oral efficacy of recombinant granulocyte colony-stimulating factor and transferrin fusion protein by spacer optimization*. Pharm Res, 2006. 23(9): p. 2116-21.
6. Chen, X., J. L. Zaro, and W. C. Shen, *Fusion protein linkers: property, design and functionality*. Adv Drug Deliv Rev, 2013. 65(10): p. 1357-69.
7. Vang, R., M. Shih Ie, and R. J. Kurman, *Ovarian low-grade and high-grade serous carcinoma: pathogenesis, clinicopathologic and molecular biologic features, and diagnostic problems*. Adv Anat Pathol, 2009. 16(5): p. 267-82.
8. Luvero, D., A. Milani, and J. A. Ledermann, *Treatment options in recurrent ovarian cancer: latest evidence and clinical potential*. Ther Adv Med Oncol, 2014. 6(5): p. 229-39.
9. Bast, R. C., Jr., B. Hennessy, and G. B. Mills, *The biology of ovarian cancer: new opportunities for translation*. Nat Rev Cancer, 2009. 9(6): p. 415-28.
10. Cancer Genome Atlas Research, N., *Integrated genomic analyses of ovarian carcinoma*. Nature, 2011. 474(7353): p. 609-15.
11. Zeimet, A. G. and C. Marth, *Why did p53 gene therapy fail in ovarian cancer?* Lancet Oncol, 2003. 4(7): p. 415-22.
12. Erster, S., et al., *In vivo mitochondrial p53 translocation triggers a rapid first wave of cell death in response to DNA damage that can precede p53 target gene activation*. Mol Cell Biol, 2004. 24(15): p. 6728-41.
13. Mossalam, M., et al., *Direct induction of apoptosis using an optimal mitochondrially targeted p53*. Mol Pharm, 2012. 9(5): p. 1449-58.
14. Vaseva, A. V. and U. M. Moll, *The mitochondrial p53 pathway*. Biochim Biophys Acta, 2009. 1787(5): p. 414-20.
15. Perfettini, J. L., R. T. Kroemer, and G. Kroemer, *Fatal liaisons of p53 with Bax and Bak*. Nat Cell Biol, 2004. 6(5): p. 386-8.
16. Matissek, K. J., et al., *The DNA binding domain of p53 is sufficient to trigger a potent apoptotic response at the mitochondria*. Mol Pharm, 2013. 10(10): p. 3592-602.
17. Matissek, K. J., et al., *Delivery of a monomeric p53 subdomain with mitochondrial targeting signals from pro-apoptotic Bak or Bax*. Pharm Res, 2014. 31(9): p. 2503-15.
18. Danial, N. N., *BAD: undertaker by night, candyman by day*. Oncogene, 2008. 27 Suppl 1: p. 553-70.
19. Cong, Y. S., J. Wen, and S. Bacchetti, *The human telomerase catalytic subunit hTERT: organization of the gene and characterization of the promoter*. Hum Mol Genet, 1999. 8(1): p. 137-42.
20. Davis, J. J., et al., *Oncolysis and suppression of tumor growth by a GFP-expressing oncolytic adenovirus controlled by an hTERT and CMV hybrid promoter*. Cancer Gene Ther, 2006. 13(7): p. 720-3.
21. Horikawa, I., et al., *Cloning and characterization of the promoter region of human telomerase reverse transcriptase gene*. Cancer Res, 1999. 59(4): p. 826-30.
22. Kim, N. W., et al., *Specific association of human telomerase activity with immortal cells and cancer*. Science, 1994. 266(5193): p. 2011-5.
23. Kyo, S., et al., *Understanding and exploiting hTERT promoter regulation for diagnosis and treatment of human cancers*. Cancer Sci, 2008. 99(8): p. 1528-38.
24. Li, Y. H., et al., *Enhancing HSP70-ShRNA transfection in 22RV1 prostate cancer cells by combination of sonoporation, liposomes and HTERT/CMV chimeric promoter*. Int J Oncol, 2013. 43(1): p. 151-8.
25. Ramlee, M. K., et al., *Transcription Regulation of the Human Telomerase Reverse Transcriptase (hTERT) Gene*. Genes, 2016. 7(8).
26. Takakura, M., et al., *Cloning of human telomerase catalytic subunit (hTERT) gene promoter and identification of proximal core promoter sequences essential for transcriptional activation in immortalized and cancer cells*. Cancer Res, 1999. 59(3): p. 551-7.
27. Xie, X., et al., *A novel hTERT promoter-driven E1A therapeutic for ovarian cancer*. Mol Cancer Ther, 2009. 8(8): p. 2375-82.
28. Chen, X., et al., *Cancer-specific promoters for expression-targeted gene therapy: ran, brms1 and mcm5*. J Gene Med, 2016. 18(7): p. 89-101.
29. Kim, J., et al., *Enhancing the therapeutic efficacy of adenovirus in combination with biomaterials*. Biomaterials, 2012. 33(6): p. 1838-50.
30. Kim, J., et al., *Therapeutic efficacy of a systemically delivered oncolytic adenovirus—biodegradable polymer complex*. Biomaterials, 2013. 34(19): p. 4622-31.
31. Kim, J., et al., *Efficient lung orthotopic tumor-growth suppression of oncolytic adenovirus complexed with RGD-targeted bioreducible polymer*. Gene Ther, 2014. 21(5): p. 476-83.
32. Kim, J., et al., *Active targeting of RGD-conjugated bioreducible polymer for delivery of oncolytic adenovirus expressing shRNA against IL-8 mRNA*. Biomaterials, 2011. 32(22): p. 5158-66.
33. Kim, P. H., et al., *Bioreducible polymer-conjugated oncolytic adenovirus for hepatoma-specific therapy via systemic administration*. Biomaterials, 2011. 32(35): p. 9328-42.
34. Kim, P. H., et al., *The effect of surface modification of adenovirus with an arginine-grafted bioreducible polymer on transduction efficiency and immunogenicity in cancer gene therapy*. Biomaterials, 2010. 31(7): p. 1865-74.
35. Cho, S., et al., *Characterization and evaluation of pre-clinical suitability of a syngeneic orthotopic mouse ovarian cancer model*. Anticancer Res, 2013. 33(4): p. 1317-24.

36. Zervantonakis, I. K., et al., *Systems analysis of apoptotic priming in ovarian cancer identifies vulnerabilities and predictors of drug response*. Nat Commun, 2017. 8(1): p. 365.
37. Howlader N, N. A., Krapcho M, Garshell J, Neyman N, Altekruse S F, Kosary C L, Yu M, Ruhl J, Tatalovich Z, Cho H, Mariotto A, Lewis D R, Chen H S, Feuer E J, Cronin K A (eds). SEER Cancer Statistics Review, 1975-2010, National Cancer Institute. Bethesda, Md. 2013 [cited 2013 Oct. 7, 2013]; Available from: http://seer.cancer.gov/csr/1975 2010/.
38. Lozano, R., et al., *Global and regional mortality from 235 causes of death for 20 age groups in 1990 and 2010: a systematic analysis for the Global Burden of Disease Study* 2010. Lancet, 2012. 380(9859): p. 2095-128.
39. Mould, T., *An overview of current diagnosis and treatment in ovarian cancer*. Int J Gynecol Cancer, 2012. 22 Suppl 1: p. S2-4.
40. Kim, A., et al., *Therapeutic strategies in epithelial ovarian cancer*. J Exp Clin Cancer Res, 2012. 31: p. 14.
41. Wojnarowicz, P. M., et al., *The genomic landscape of TP53 and p53 annotated high grade ovarian serous carcinomas from a defined founder population associated with patient outcome*. PLoS One, 2012. 7(9): p. e45484.
42. Sapiezynski, J., et al., *Precision targeted therapy of ovarian cancer*. J Control Release, 2016. 243: p. 250-268.
43. Shaw, H. M. and M. Hall, *Emerging treatment options for recurrent ovarian cancer: the potential role of olaparib*. Onco Targets Ther, 2013. 6: p. 1197-206.
44. Coleman, R. L., et al., *Latest research and treatment of advanced-stage epithelial ovarian cancer*. Nat Rev Clin Oncol, 2013. 10(4): p. 211-24.
45. Ye, Q. and H. L. Chen, *Bevacizumab in the treatment of ovarian cancer: a meta-analysis from four phase III randomized controlled trials*. Arch Gynecol Obstet, 2013. 288(3): p. 655-66.
46. Romero, I. and R. C. Bast, Jr., *Minireview: human ovarian cancer: biology, current management, and paths to personalizing therapy*. Endocrinology, 2012. 153(4): p. 1593-602.
47. Chumworathayi, B., *Personalized cancer treatment for ovarian cancer*. Asian Pac J Cancer Prev, 2013. 14(3): p. 1661-4.
48. Mahner, S. and J. Pfisterer, *Towards individualised treatment in ovarian cancer*. Lancet Oncol, 2013. 14(2): p. 101-2.
49. Patch, A. M., et al., *Whole-genome characterization of chemoresistant ovarian cancer*. Nature, 2015. 521(7553): p. 489-94.
50. Marchenko, N. D., A. Zaika, and U. M. Moll, *Death signal-induced localization of p53 protein to mitochondria. A potential role in apoptotic signaling*. J Biol Chem, 2000. 275(21): p. 16202-12.
51. Mihara, M., et al., *p53 has a direct apoptogenic role at the mitochondria*. Mol Cell, 2003. 11(3): p. 577-90.
52. Palacios, G., et al., *Mitochondrially targeted wild-type p53 induces apoptosis in a solid human tumor xenograft model*. Cell Cycle, 2008. 7(16): p. 2584-90.
53. Talos, F., et al., *Mitochondrially targeted p53 has tumor suppressor activities in vivo*. Cancer Res, 2005. 65(21): p. 9971-81.
54. Delbridge, A. R. and A. Strasser, *The BCL-2 protein family, BH3-mimetics and cancer therapy*. Cell Death Differ, 2015. 22(7): p. 1071-80.
55. Shamas-Din, A., et al., *BH3-only proteins: Orchestrators of apoptosis*. Biochim Biophys Acta, 2011. 1813(4): p. 508-20.
56. Okal, A., et al., *Re-engineered p53 chimera with enhanced homo-oligomerization that maintains tumor suppressor activity*. Mol Pharm, 2014. 11(7): p. 2442-52.
57. Okal, A., et al., *Re-engineered p53 activates apoptosis in vivo and causes primary tumor regression in a dominant negative breast cancer xenograft model*. Gene Ther, 2014. 21(10): p. 903-12.
58. Okal, A., et al., *A chimeric p53 evades mutant p53 transdominant inhibition in cancer cells*. Mol Pharm, 2013. 10(10): p. 3922-33.
59. Reaz, S., et al., *A single mutant, A276S of p53, turns the switch to apoptosis*. Mol Pharm, 2013. 10(4): p. 1350-9.
60. Palacios, G. and U. M. Moll, *Mitochondrially targeted wild-type p53 suppresses growth of mutant p53 lymphomas in vivo*. Oncogene, 2006. 25(45): p. 6133-9.
61. Lee, D. H., et al., *A conserved mechanism for binding of p53 DNA-binding domain and anti-apoptotic Bcl-2 family proteins*. Mol Cells, 2014. 37(3): p. 264-9.
62. Camel, A., et al., *The cytoplasmic side of p53's oncosuppressive activities*. FEBS Lett, 2014. 588(16): p. 2600-9.
63. Liu, B., Y. Chen, and D. K. St Clair, *ROS and p53: a versatile partnership*. Free Radic Biol Med, 2008. 44(8): p. 1529-35.
64. Kim, E. M., et al., *Nuclear and cytoplasmic p53 suppress cell invasion by inhibiting respiratory complex-I activity via Bcl-2 family proteins*. Oncotarget, 2014. 5(18): p. 8452-65.
65. Sarosiek, K. A., T. Ni Chonghaile, and A. Letai, *Mitochondria: gatekeepers of response to chemotherapy*. Trends Cell Biol, 2013. 23(12): p. 612-9.
66. Cang, S., et al., *ABT-199 (venetoclax) and BCL-2 inhibitors in clinical development*. J Hematol Oncol, 2015. 8: p. 129.
67. Gibson, C. J. and M. S. Davids, *BCL-2 Antagonism to Target the Intrinsic Mitochondrial Pathway of Apoptosis*. Clin Cancer Res, 2015. 21(22): p. 5021-9.
68. Touzeau, C., et al., *The Bcl-2 specific BH3 mimetic ABT-199: a promising targeted therapy for t(11;14) multiple myeloma*. Leukemia, 2014. 28(1): p. 210-2.
69. Liu, Q. and H. G. Wang, *Anti-cancer drug discovery and development: Bcl-2 family small molecule inhibitors*. Commun Integr Biol, 2012. 5(6): p. 557-65.
70. Anderson, N. S., et al., *Bcl-2 expression is altered with ovarian tumor progression: an immunohistochemical evaluation*. J Ovarian Res, 2009. 2: p. 16.
71. Williams, J., et al., *Expression of Bcl-xL in ovarian carcinoma is associated with chemoresistance and recurrent disease*. Gynecol Oncol, 2005. 96(2): p. 287-95.
72. Shigemasa, K., et al., *Increased MCL-1 expression is associated with poor prognosis in ovarian carcinomas*. Jpn J Cancer Res, 2002. 93(5): p. 542-50.
73. Chipuk, J. E., et al., *The BCL-2 family reunion*. Mol Cell, 2010. 37(3): p. 299-310.
74. van Delft, M. F., et al., *The BH3 mimetic ABT-737 targets selective Bcl-2 proteins and efficiently induces apoptosis via Bak/Bax if Mcl-1 is neutralized*. Cancer Cell, 2006. 10(5): p. 389-99.
75. Placzek, W. J., et al., *A survey of the anti-apoptotic Bcl-2 subfamily expression in cancer types provides a platform to predict the efficacy of Bcl-2 antagonists in cancer therapy*. Cell Death Dis, 2010. 1: p. e40.
76. Montero, J. and A. Letai, *Dynamic BH3 profiling-poking cancer cells with a stick*. Mol Cell Oncol, 2016. 3(3): p. e1040144.
77. Touzeau, C., et al., *BH3 profiling identifies heterogeneous dependency on Bcl-2 family members in multiple*

77. *myeloma and predicts sensitivity to BH3 mimetics.* Leukemia, 2016. 30(3): p. 761-4.
78. Ni Chonghaile, T., et al., *Pretreatment mitochondrial priming correlates with clinical response to cytotoxic chemotherapy.* Science, 2011. 334(6059): p. 1129-33.
79. Lu, P., et al., *Delivery of drugs and macromolecules to the mitochondria for cancer therapy.* J Control Release, 2016. 240: p. 38-51.
80. Chao, D. T. and S. J. Korsmeyer, *BCL-2 family: regulators of cell death.* Annu Rev Immunol, 1998. 16: p. 395-419.
81. Czabotar, P. E., et al., *Control of apoptosis by the BCL-2 protein family: implications for physiology and therapy.* Nat Rev Mol Cell Biol, 2014. 15(1): p. 49-63.
82. O'Connor, L., et al., *Bim: a novel member of the Bcl-2 family that promotes apoptosis.* EMBO J, 1998. 17(2): p. 384-95.
83. Oda, E., et al., *Noxa, a BH3-only member of the Bcl-2 family and candidate mediator of p53-induced apoptosis.* Science, 2000. 288(5468): p. 1053-8.
84. Puthalakath, H., et al., *The proapoptotic activity of the Bcl-2 family member Bim is regulated by interaction with the dynein motor complex.* Mol Cell, 1999. 3(3): p. 287-96.
85. Weber, A., et al., *BimS-induced apoptosis requires mitochondrial localization but not interaction with anti-apoptotic Bcl-2 proteins.* J Cell Biol, 2007. 177(4): p. 625-36.
86. Ambroise, G., et al., *Subcellular localization of PUMA regulates its pro-apoptotic activity in Burkitt's lymphoma B cells.* Oncotarget, 2015. 6(35): p. 38181-94.
87. Wang, H., et al., *A feasibility study on gene therapy of pancreatic carcinoma with Ad-PUMA.* Cancer Biol Ther, 2012. 13(9): p. 712-9.
88. Shan, Z., et al., *PUMA decreases the growth of prostate cancer PC-3 cells independent of p53.* Oncol Lett, 2017. 13(3): p. 1885-1890.
89. Gu, J., et al., *hTERT promoter induces tumor-specific Bax gene expression and cell killing in syngenic mouse tumor model and prevents systemic toxicity.* Gene Ther, 2002. 9(1): p. 30-7.
90. Zang, G., et al., *Adenoviral mediated transduction of adenoid cystic carcinoma by human TRAIL gene driven with hTERT tumor specific promoter induces apoptosis.* Cancer Biol Ther, 2009. 8(10): p. 966-72.
91. Ramirez, M., et al., *Diverse drug-resistance mechanisms can emerge from drug-tolerant cancer persister cells.* Nat Commun, 2016. 7: p. 10690.
92. Zhai, B. and X. Y. Sun, *Mechanisms of resistance to sorafenib and the corresponding strategies in hepatocellular carcinoma.* World J Hepatol, 2013. 5(7): p. 345-52.
93. Datta, S. R., et al., *Survival factor-mediated BAD phosphorylation raises the mitochondrial threshold for apoptosis.* Dev Cell, 2002. 3(5): p. 631-43.
94. Fang, X., et al., *Regulation of BAD phosphorylation at serine 112 by the Ras-mitogen-activated protein kinase pathway.* Oncogene, 1999. 18(48): p. 6635-40.
95. Virdee, K., P. A. Parone, and A. M. Tolkovsky, *Phosphorylation of the pro-apoptotic protein BAD on serine 155, a novel site, contributes to cell survival.* Current biology: CB, 2000. 10(18): p. 1151-4.
96. Klumpp, S. and J. Krieglstein, *Serine/threonine protein phosphatases in apoptosis.* Curr Opin Pharmacol, 2002. 2(4): p. 458-62.
97. Hermeking, H., *The 14-3-3 cancer connection.* Nat Rev Cancer, 2003. 3(12): p. 931-43.
98. Datta, S. R., et al., *14-3-3 proteins and survival kinases cooperate to inactivate BAD by BH3 domain phosphorylation.* Mol Cell, 2000. 6(1): p. 41-51.
99. Tan, Y., et al., *BAD Ser-155 phosphorylation regulates BAD/Bcl-XL interaction and cell survival.* J Biol Chem, 2000. 275(33): p. 25865-9.
100. Roy, S. S., et al., *Bad targets the permeability transition pore independent of Bax or Bak to switch between Ca2+-dependent cell survival and death.* Mol Cell, 2009. 33(3): p. 377-88.
101. Chou, J J., et al., *Solution structure of BID, an intracellular amplifier of apoptotic signaling.* Cell, 1999. 96(5): p. 615-24.
102. Huang, K., et al., *Cleavage by Caspase 8 and Mitochondrial Membrane Association Activate the BH3-only Protein Bid during TRAIL-induced Apoptosis.* J Biol Chem, 2016. 291(22): p. 11843-51.
103. Wilfling, F., et al., *BH3-only proteins are tail-anchored in the outer mitochondrial membrane and can initiate the activation of Bax.* Cell Death Differ, 2012. 19(8): p. 1328-36.
104. Planer, C., R. Kofler, and A. Villunger, *Noxa: at the tip of the balance between life and death.* Oncogene, 2008. 27 Suppl 1: p. S84-92.
105. Lin, C., et al., *NOXA-induced alterations in the Bax/Smac axis enhance sensitivity of ovarian cancer cells to cisplatin.* PLoS One, 2012. 7(5): p. e36722.
106. Karim, C. B., et al., *Structural Mechanism for Regulation of Bcl/2 protein Noxa by phosphorylation.* Sci Rep, 2015. 5: p. 14557.
107. Barbolina, M. V., et al., *Wilms tumor gene protein 1 is associated with ovarian cancer metastasis and modulates cell invasion.* Cancer, 2008. 112(7): p. 1632-41.
108. Ferrer, P. E., et al., *Translocation of a Bak C-terminus mutant from cytosol to mitochondria to mediate cytochrome C release: implications for Bak and Bax apoptotic function.* PLoS One, 2012. 7(3): p. e31510.
109. Seo, Y. W., et al., *The cell death-inducing activity of the peptide containing Noxa mitochondrial-targeting domain is associated with calcium release.* Cancer Res, 2009. 69(21): p. 8356-65.
110. Okal, A., et al., *A Chimeric p53 Evades Mutant p53 Transdominant Inhibition in Cancer Cells.* Mol Pharm, 2013.
111. Davis, J. R., M. Mossalam, and C. S. Lim, *Controlled access of p53 to the nucleus regulates its proteasomal degradation by MDM2.* Mol Pharm, 2013. 10(4): p. 1340-9.
112. Matissek, K. J., et al., *The DNA Binding Domain of p53 Is Sufficient To Trigger a Potent Apoptotic Response at the Mitochondria.* Mol Pharm, 2013.
113. Constance, J. E., et al., *Enhanced and selective killing of chronic myelogenous leukemia cells with an engineered BCR-ABL binding protein and imatinib.* Mol Pharm, 2012. 9(11): p. 3318-29.
114. Domcke, S., et al., *Evaluating cell lines as tumour models by comparison of genomic profiles.* Nat Commun, 2013. 4: p. 2126.
115. Janat-Amsbury, M. M., et al., *Combination of local, non-viral IL12 gene therapy and systemic paclitaxel chemotherapy in a syngeneic 108 mouse model for human ovarian cancer.* Anticancer Res, 2006. 26(5A): p. 3223-8.
116. Sablina, A. A., P. M. Chumakov, and B. P. Kopnin, *Tumor suppressor p53 and its homologue p73alpha affect cell migration.* J Biol Chem, 2003. 278(30): p. 27362-71.

117. Dixon, A. S., et al., *Disruption of Bcr-Abl coiled coil oligomerization by design.* J Biol Chem, 2011. 286(31): p. 27751-60.
118. Barrett, K. L., et al., *Advances in cytochemical methods for detection of apoptosis.* J Histochem Cytochem, 2001. 49(7): p. 821-32.
119. Willingham, M. C., *Cytochemical methods for the detection of apoptosis.* J Histochem Cytochem, 1999. 47(9): p. 1101-10.
120. Chan, G. K., et al., *A simple high-content cell cycle assay reveals frequent discrepancies between cell number and ATP and MTS proliferation assays.* PLoS One, 2013. 8(5): p. e63583.
121. Hajiahmadi, S., et al., *Activation of A2b adenosine receptor regulates ovarian cancer cell growth: involvement of Bax/Bcl-2 and caspase-3.* Biochem Cell Biol, 2015. 93(4): p. 321-9.
122. Nolan, T., R. E. Hands, and S. A. Bustin, *Quantification of mRNA using real-time RT-PCR.* Nat Protoc, 2006. 1(3): p. 1559-82.
123. Acuner Ozbabacan, S. E., et al., *Transient protein-protein interactions.* Protein Eng Des Sel, 2011. 24(9): p. 635-48.
124. Kim, T. I. and S. W. Kim, *Bioreducible polymers for gene delivery.* React Funct Polym, 2011. 71(3): p. 344-349.
125. Danhier, F., A. Le Breton, and V. Preat, *RGD-based strategies to target alpha(v) beta(3) integrin in cancer therapy and diagnosis.* Mol Pharm, 2012. 9(11): p. 2961-73.
126. Fewell, J. G., et al., *Treatment of disseminated ovarian cancer using nonviral interleukin—12 gene therapy delivered intraperitoneally.* J Gene Med, 2009. 11(8): p. 718-28.
127. Kim, J., et al., *Intraperitoneal gene therapy with adenoviral-mediated p53 tumor suppressor gene for ovarian cancer model in nude mouse.* Cancer Gene Ther, 1999. 6(2): p. 172-8.
128. von Gruenigen, V. E., et al., *In vivo studies of adenovirus-based p53 gene therapy for ovarian cancer.* Gynecol Oncol, 1998. 69(3): p. 197-204.
129. Okal, A., et al., *Re-engineered p53 activates apoptosis in vivo and causes primary tumor regression in a dominant negative breast cancer xenograft model.* Gene Ther, 2014. in press.
130. Fennell, D. A., *Bcl-2 as a target for overcoming chemoresistance in small-cell lung cancer.* Clin Lung Cancer, 2003. 4(5): p. 307-13.
131. Minami, T., et al., *Overcoming chemoresistance of small-cell lung cancer through stepwise HER2-targeted antibody-dependent cell-mediated cytotoxicity and VEGF-targeted antiangiogenesis.* Sci Rep, 2013. 3: p. 2669.
1. Kim A, Ueda Y, Naka T, Enomoto T. Therapeutic strategies in epithelial ovarian cancer. J Exp Clin Cancer Res. 2012; 31:14.
2. Wojnarowicz P M, Oros K K, Quinn M C, Arcand S L, Gambaro K, Madore J, et al. The genomic landscape of TP53 and p53 annotated high grade ovarian serous carcinomas from a defined founder population associated with patient outcome. PLoS One. 2012; 7(9):e45484.
3. Romero I, Bast R C, Jr. Minireview: human ovarian cancer: biology, current management, and paths to personalizing therapy. Endocrinology. 2012; 153(4):1593-602.
4. Howlader N N A, Krapcho M, Garshell J, Neyman N, Altekruse S F, Kosary C L, Yu M, Ruhl J, Tatalovich Z, Cho H, Mariotto A, Lewis D R, Chen H S, Feuer E J, Cronin K A (eds). SEER Cancer Statistics Review, 1975-2010, National Cancer Institute. Bethesda, Md. 2013 [Available from: http://seer.cancer.Rov/csr/1975 2010/.
5. Sapiezynski J, Taratula O, Rodriguez-Rodriguez L, Minko T. Precision targeted therapy of ovarian cancer. J Control Release. 2016; 243:250-68.
6. Shaw H M, Hall M. Emerging treatment options for recurrent ovarian cancer: the potential role of olaparib. Onco Targets Ther. 2013; 6:1197-206.
7. Coleman R L, Monk B J, Sood A K, Herzog T J. Latest research and treatment of advanced-stage epithelial ovarian cancer. Nat Rev Clin Oncol. 2013; 10(4):211-24.
8. Ye Q, Chen H L. Bevacizumab in the treatment of ovarian cancer: a meta-analysis from four phase III randomized controlled trials. Arch Gynecol Obstet. 2013; 288(3):655-66.
9. Hermeking H. The 14-3-3 cancer connection. Nat Rev Cancer. 2003; 3(12):931-43.
10. Matissek K J, Mossalam M, Okal A, Lim C S. The DNA binding domain of p53 is sufficient to trigger a potent apoptotic response at the mitochondria. Mol Pharm. 2013; 10(10):3592-602.
11. Cancer Genome Atlas Research N. Integrated genomic analyses of ovarian carcinoma. Nature. 2011; 474(7353): 609-15.
12. Mossalam M, Matissek K J, Okal A, Constance J E, Lim C S. Direct induction of apoptosis using an optimal mitochondrially targeted p53. Mol Pharm. 2012; 9(5): 1449-58.
13. Patch A M, Christie E L, Etemadmoghadam D, Garsed D W, George J, Fereday S, et al. Whole-genome characterization of chemoresistant ovarian cancer. Nature. 2015; 521(7553):489-94.
14. Matissek K J, Okal A, Mossalam M, Lim C S. Delivery of a monomeric p53 subdomain with mitochondrial targeting signals from pro-apoptotic Bak or Bax. Pharm Res. 2014; 31(9):2503-15.
15. Matissek K J, Mossalam M, Okal A, Lim C S. The DNA binding domain of p53 is sufficient to trigger a potent apoptotic response at the mitochondria. Mol Pharm. 2013; 10(10):3592-602.
16. Danial N N. BAD: undertaker by night, candyman by day. Oncogene. 2008; 27 Suppl 1:S53-70.
17. Vaseva A V, Moll U M. The mitochondrial p53 pathway. Biochim Biophys Acta. 2009; 1787(5):414-20.
18. Erster S, Mihara M, Kim R H, Petrenko O, Moll U M. In vivo mitochondrial p53 translocation triggers a rapid first wave of cell death in response to DNA damage that can precede p53 target gene activation. Mol Cell Biol. 2004; 24(15):6728-41.
19. Marchenko N D, Zaika A, Moll U M. Death signal-induced localization of p53 protein to mitochondria. A potential role in apoptotic signaling. J Biol Chem. 2000; 275(21):16202-12.
20. Mihara M, Erster S, Zaika A, Petrenko O, Chittenden T, Pancoska P, et al. p53 has a direct apoptogenic role at the mitochondria. Mol Cell. 2003; 11(3):577-90.
21. Heyne K, Schmitt K, Mueller D, Armbruester V, Mestres P, Roemer K. Resistance of mitochondrial p53 to dominant inhibition. Mol Cancer. 2008; 7:54.
22. Kim E M, Park J K, Hwang S G, Kim W J, Liu Z G, Kang S W, et al. Nuclear and cytoplasmic p53 suppress cell invasion by inhibiting respiratory complex-I activity via Bcl-2 family proteins. Oncotarget. 2014; 5(18):8452-65.

23. Roy S S, Madesh M, Davies E, Antonsson B, Danial N, Hajnoczky G. Bad targets the permeability transition pore independent of Bax or Bak to switch between Ca2+-dependent cell survival and death. Mol Cell. 2009; 33(3): 377-88.
24. Okal A, Cornillie S, Matissek S J, Matissek K J, Cheatham T E, 3rd, Lim C S. Re-engineered p53 chimera with enhanced homo-oligomerization that maintains tumor suppressor activity. Mol Pharm. 2014; 11(7):2442-52.
25. Okal A, Matissek K J, Matissek S J, Price R, Salama M E, Janat-Amsbury M M, et al. Re-engineered p53 activates apoptosis in vivo and causes primary tumor regression in a dominant negative breast cancer xenograft model. Gene Ther. 2014; 21(10):903-12.
26. Okal A, Mossalam M, Matissek K J, Dixon A S, Moos P J, Lim C S. A chimeric p53 evades mutant p53 transdominant inhibition in cancer cells. Mol Pharm. 2013; 10(10):3922-33.
27. Reaz S, Mossalam M, Okal A, Lim C S. A single mutant, A276S of p53, turns the switch to apoptosis. Mol Pharm. 2013; 10(4):1350-9.
28. Cong Y S, Wen J, Bacchetti S. The human telomerase catalytic subunit hTERT: organization of the gene and characterization of the promoter. Hum Mol Genet. 1999; 8(1):137-42.
29. Costes S V, Daelemans D, Cho E H, Dobbin Z, Pavlakis G, Lockett S. Automatic and quantitative measurement of protein-protein colocalization in live cells. Biophys J. 2004; 86(6):3993-4003.
30. Bolte S, Cordelieres F P. A guided tour into subcellular colocalization analysis in light microscopy. J Microsc. 2006; 224(Pt 3):213-32.
31. Mullany L K, Wong K K, Marciano D C, Katsonis P, King-Crane E R, Ren Y A, et al. Specific TP53 Mutants Overrepresented in Ovarian Cancer Impact CNV, TP53 Activity, Responses to Nutlin-3a, and Cell Survival. Neoplasia. 2015; 17(10):789-803.
32. Son D S, Kabir S M, Dong Y L, Lee E, Adunyah S E. Inhibitory effect of tumor suppressor p53 on proinflammatory chemokine expression in ovarian cancer cells by reducing proteasomal degradation of IkappaB. PLoS One. 2012; 7(12):e51116.
33. Placzek W J, Wei J, Kitada S, Zhai D, Reed J C, Pellecchia M. A survey of the anti-apoptotic Bcl-2 subfamily expression in cancer types provides a platform to predict the efficacy of Bcl-2 antagonists in cancer therapy. Cell Death Dis. 2010; 1:e40.
34. Janat-Amsbury M M, Yockman J W, Anderson M L, Kieback D G, Kim S W. Combination of local, non-viral IL12 gene therapy and systemic paclitaxel chemotherapy in a syngeneic ID8 mouse model for human ovarian cancer. Anticancer Res. 2006; 26(5A):3223-8.
35. Janat-Amsbury M M, Yockman J W, Anderson M L, Kieback D G, Kim S W. Comparison of ID8 MOSE and VEGF-modified ID8 cell lines in an immunocompetent animal model for human ovarian cancer. Anticancer Res. 2006; 26(4B):2785-9.
36. Cho S, Sun Y, Soisson A P, Dodson M K, Peterson C M, Jarboe E A, et al. Characterization and evaluation of pre-clinical suitability of a syngeneic orthotopic mouse ovarian cancer model. Anticancer Res. 2013; 33(4):1317-24.
37. Abed M N, Abdullah M I, Richardson A. Antagonism of Bcl-XL is necessary for synergy between carboplatin and BH3 mimetics in ovarian cancer cells. J Ovarian Res. 2016; 9:25.
38. Soragni A, Janzen D M, Johnson L M, Lindgren A G, Thai-Quynh Nguyen A, Tiourin E, et al. A Designed Inhibitor of p53 Aggregation Rescues p53 Tumor Suppression in Ovarian Carcinomas. Cancer Cell. 2016; 29(1):90-103.
39. Yaginuma Y, Westphal H. Abnormal structure and expression of the p53 gene in human ovarian carcinoma cell lines. Cancer Res. 1992; 52(15):4196-9.
40. Domcke S, Sinha R, Levine D A, Sander C, Schultz N. Evaluating cell lines as tumour models by comparison of genomic profiles. Nat Commun. 2013; 4:2126.
41. Danhier F, Le Breton A, Preat V. RGD-based strategies to target alpha(v) beta(3) integrin in cancer therapy and diagnosis. Mol Pharm. 2012; 9(11):2961-73.
42. Kim J, Nam H Y, Choi J W, Yun C O, Kim S W. Efficient lung orthotopic tumor-growth suppression of oncolytic adenovirus complexed with RGD-targeted bioreducible polymer. Gene Ther. 2014; 21(5):476-83.
43. Hastie E, Cataldi M, Steuerwald N, Grdzelishvili V Z. An unexpected inhibition of antiviral signaling by virus-encoded tumor suppressor p53 in pancreatic cancer cells. Virology. 2015; 483:126-40.
44. Kim J, Nam H Y, Kim T I, Kim P H, Ryu J, Yun C O, et al. Active targeting of RGD-conjugated bioreducible polymer for delivery of oncolytic adenovirus expressing shRNA against IL-8 mRNA. Biomaterials. 2011; 32(22): 5158-66.
45. Elmore S. Apoptosis: a review of programmed cell death. Toxicol Pathol. 2007; 35(4):495-516.
46. Hao Z, Mak T W. Type I and type II pathways of Fas-mediated apoptosis are differentially controlled by XIAP. J Mol Cell Biol. 2010; 2(2):63-4.
47. Lu P, Bruno B J, Rabenau M, Lim C S. Delivery of drugs and macromolecules to the mitochondria for cancer therapy. J Control Release. 2016; 240:38-51.
48. Datta S R, Katsov A, Hu L, Petros A, Fesik S W, Yaffe M B, et al. 14-3-3 proteins and survival kinases cooperate to inactivate BAD by BH3 domain phosphorylation. Mol Cell. 2000; 6(1):41-51.
49. Czabotar P E, Lessene G, Strasser A, Adams J M. Control of apoptosis by the BCL-2 protein family: implications for physiology and therapy. Nat Rev Mol Cell Biol. 2014; 15(1):49-63.
50. Janat-Amsbury M M, Yockman J W, Lee M, Kern S, Furgeson D Y, Bikram M, et al. Combination of local, nonviral IL12 gene therapy and systemic paclitaxel treatment in a metastatic breast cancer model. Mol Ther. 2004; 9(6):829-36.
51. Yokoyama T, Kohn E, Brill E, Lee J M. Apoptosis is augmented in high-grade serous ovarian cancer by the combined inhibition of Bcl-2/Bcl-xL and PARP. Int J Oncol. 2017.
52. Luvero D, Milani A, Ledermann J A. Treatment options in recurrent ovarian cancer: latest evidence and clinical potential. Ther Adv Med Oncol. 2014; 6(5):229-39.
53. Bicaku E, Xiong Y, Marchion D C, Chon H S, Stickles X B, Chen N, et al. In vitro analysis of ovarian cancer response to cisplatin, carboplatin, and paclitaxel identifies common pathways that are also associated with overall patient survival. Br J Cancer. 2012; 106(12):1967-75.
54. Sarosiek K A, Ni Chonghaile T, Letai A. Mitochondria: gatekeepers of response to chemotherapy. Trends Cell Biol. 2013; 23(12):612-9.
55. Fulda S, Galluzzi L, Kroemer G. Targeting mitochondria for cancer therapy. Nat Rev Drug Discov. 2010; 9(6):447-64.

56. Liu B, Chen Y, St Clair D K. ROS and p53: a versatile partnership. Free Radic Biol Med. 2008; 44(8):1529-35.
57. Chipuk J E, Moldoveanu T, Llambi F, Parsons M J, Green D R. The BCL-2 family reunion. Mol Cell. 2010; 37(3):299-310.
58. Datta S R, Ranger A M, Lin M Z, Sturgill J F, Ma Y C, Cowan C W, et al. Survival factor-mediated BAD phosphorylation raises the mitochondrial threshold for apoptosis. Dev Cell. 2002; 3(5):631-43.
59. Touzeau C, Dousset C, Le Gouill S, Sampath D, Leverson J D, Souers A J, et al. The Bcl-2 specific BH3 mimetic ABT-199: a promising targeted therapy for t(11;14) multiple myeloma. Leukemia. 2014; 28(1):210-2.
60. Liu, Wang H G. Anti-cancer drug discovery and development: Bcl-2 family small molecule inhibitors. Commun Integr Biol. 2012; 5(6):557-65.
61. Vang R, Shih le M, Kurman R J. Ovarian low-grade and high-grade serous carcinoma: pathogenesis, clinicopathologic and molecular biologic features, and diagnostic problems. Adv Anat Pathol. 2009; 16(5):267-82.
62. Tan Y, Demeter M R, Ruan H, Comb M J. BAD Ser-155 phosphorylation regulates BAD/Bcl-XL interaction and cell survival. J Biol Chem. 2000; 275(33):25865-9.
63. Virdee K, Parone P A, Tolkovsky A M. Phosphorylation of the pro-apoptotic protein BAD on serine 155, a novel site, contributes to cell survival. Curr Biol. 2000; 10(18): 1151-4.
64. Yockman J W, Kastenmeier A, Erickson H M, Brumbach J G, Whitten M G, Albanil A, et al. Novel polymer carriers and gene constructs for treatment of myocardial ischemia and infarction. J Control Release. 2008; 132(3):260-6.
65. Janat-Amsbury M M, Peterson C M, Kim S W. The role of gene- and drug delivery in women's health-unmet clinical needs and future opportunities. Preface. Adv Drug Deliv Rev. 2009; 61(10):767.
66. Leu J I, Dumont P, Hafey M, Murphy M E, George D L. Mitochondrial p53 activates Bak and causes disruption of a Bak-Mcl1 complex. Nat Cell Biol. 2004; 6(5):443-50.
67. Tan Y, Demeter M R, Ruan H, Comb M J. BAD Ser-155 phosphorylation regulates BAD/Bcl-XL interaction and cell survival. J Biol Chem. 2000; 275(33):25865-9.
68. Kim P H, Kim J, Kim T I, Nam H Y, Yockman J W, Kim M, et al. Bioreducible polymer-conjugated oncolytic adenovirus for hepatoma-specific therapy via systemic administration. Biomaterials. 2011; 32(35):9328-42.
69. Kim T I, Kim S W. Bioreducible polymers for gene delivery. React Funct Polym. 2011; 71(3):344-9.
70. Choi J W, Lee J S, Kim S W, Yun C O. Evolution of oncolytic adenovirus for cancer treatment. Adv Drug Deliv Rev. 2012; 64(8):720-9.
71. Kim J, Kim P H, Kim S W, Yun C O. Enhancing the therapeutic efficacy of adenovirus in combination with biomaterials. Biomaterials. 2012; 33(6):1838-50.
72. Kim J, Li Y, Kim S W, Lee D S, Yun C O. Therapeutic efficacy of a systemically delivered oncolytic adenovirus—biodegradable polymer complex. Biomaterials. 2013; 34(19):4622-31.
73. Kasala D, Choi J W, Kim S W, Yun C O. Utilizing adenovirus vectors for gene delivery in cancer. Expert Opin Drug Deliv. 2014; 11(3):379-92.
74. Davis J J, Wang L, Dong F, Zhang L, Guo W, Teraishi F, et al. Oncolysis and suppression of tumor growth by a GFP-expressing oncolytic adenovirus controlled by an hTERT and CMV hybrid promoter. Cancer Gene Ther. 2006; 13(7):720-3.
75. Takakura M, Kyo S, Kanaya T, Hirano H, Takeda J, Yutsudo M, et al. Cloning of human telomerase catalytic subunit (hTERT) gene promoter and identification of proximal core promoter sequences essential for transcriptional activation in immortalized and cancer cells. Cancer Res. 1999; 59(3):551-7.
76. Kim N W, Piatyszek M A, Prowse K R, Harley C B, West M D, Ho P L, et al. Specific association of human telomerase activity with immortal cells and cancer. Science. 1994; 266(5193):2011-5.
77. Chen X, Scapa J E, Liu D X, Godbey W T. Cancer-specific promoters for expression-targeted gene therapy: ran, brms1 and mcm5. J Gene Med. 2016; 18(7):89-101.
78. Horikawa I, Cable P L, Afshari C, Barrett J C. Cloning and characterization of the promoter region of human telomerase reverse transcriptase gene. Cancer research. 1999; 59(4):826-30.
79. Cheung A, Bax H J, Josephs D H, Ilieva K M, Pellizzari G, Opzoomer J, et al. Targeting folate receptor alpha for cancer treatment. Oncotarget. 2016; 7(32):52553-74.

We claim:

1. A peptide comprising a p53 peptide and BAD, wherein the p53 is N-terminal to the BAD.

2. The peptide of claim 1, wherein BAD comprises the amino acid sequence of (SEQ ID NO: 1)
MFQIPEFEPSEQEDSSSAERGLGPSPAGDGPSGSGKHHRQA

PGLLWDASHQQEQPTSSSHHGGAGAVEIRSRHSSYPAGTED

DEGMGEEPSPFRGRSRSAPPNLWAAQRYGRELRRMSDEFVD

SFKKGLPRPKSAGTATQMRQSSSWTRVFQSWWDRNLGRGSS

APSQ.

3. The peptide of claim 1, wherein BAD is a mutated BAD.

4. The peptide of claim 3, wherein the mutated BAD has a serine to alanine substitution at one or more of positions 75, 99, and 118 of SEQ ID NO:1.

5. The peptide of claim 3, wherein the mutated BAD has a serine to alanine substitution at positions 75 and 99 of SEQ ID NO:1.

6. The peptide of claim 5, wherein the mutated BAD has an amino acid sequence of (SEQ ID NO: 2)
MFQIPEFEPSEQEDSSSAERGLGPSPAGDGPSGSGKHHRQA

PGLLWDASHQQEQPTSSSHHGGAGAVEIRSRHSAYPAGTED

DEGMGEEPSPFRGRSRAAPPNLWAAQRYGRELRRMSDEFVD

SFKKGLPRPKSAGTATQMRQSSSWTRVFQSWWDRNLGRGSS

APSQ.

7. The peptide of claim 1, wherein the p53 peptide is a full length p53.

8. The peptide of claim 1, wherein the p53 peptide is a partial p53 peptide, wherein the partial p53 peptide retains pro-apoptotic function.

9. The peptide of claim 1, further comprising a linker between the p53 peptide and BAD.

10. The peptide of claim 9, wherein the linker is (GGGGS)$_3$ (SEQ ID NO:9), (PAPAPA)$_3$ (SEQ ID NO:10), (EAAAK)$_3$ (SEQ ID NO:11), or [LEA(EAAAK)$_4$]$_2$LE (SEQ ID NO:12).

11. The peptide of claim 8, wherein the partial p53 peptide consists of the DNA binding domain of p53.

12. The peptide of claim 8, wherein the partial p53 peptide consists of amino acids 102-292 of SEQ ID NO:3.

13. The peptide of claim 8, wherein the partial p53 peptide comprises the DNA binding domain of p53.

14. The peptide of claim 8, wherein the partial p53 peptide further comprises a MDM2 binding domain, a proline-rich domain, a tetramerization domain, or a transactivation domain of p53.

15. A nucleic acid sequence comprising a sequence capable of encoding a p53 peptide operably linked to a nucleic acid sequence capable of encoding BAD, wherein the sequence capable of encoding a p53 peptide is 5' to the sequence capable of encoding BAD.

* * * * *